United States Patent
Colosi et al.

(10) Patent No.: US 11,821,008 B2
(45) Date of Patent: Nov. 21, 2023

(54) LIVER TARGETING ADENO-ASSOCIATED VIRAL VECTORS

(71) Applicant: BIOMARIN PHARMACEUTICAL INC., Novato, CA (US)

(72) Inventors: Peter Cameron Colosi, Novato, CA (US); Silvia Ramirez, Novato, CA (US)

(73) Assignee: BIOMARIN PHARMACEUTICAL INC., Novato, CA (US)

( * ) Notice: Subject to any disclaimer, the term of this patent is extended or adjusted under 35 U.S.C. 154(b) by 783 days.

(21) Appl. No.: 16/411,848

(22) Filed: May 14, 2019

(65) Prior Publication Data

US 2020/0024579 A1 Jan. 23, 2020

Related U.S. Application Data

(60) Provisional application No. 62/671,265, filed on May 14, 2018.

(51) Int. Cl.
| | | |
|---|---|---|
| *C12N 7/00* | (2006.01) | |
| *A61P 1/16* | (2006.01) | |
| *A61K 35/761* | (2015.01) | |
| *C07K 14/005* | (2006.01) | |
| *C12N 15/86* | (2006.01) | |

(52) U.S. Cl.
CPC ............. *C12N 7/00* (2013.01); *A61K 35/761* (2013.01); *A61P 1/16* (2018.01); *C07K 14/005* (2013.01); *C12N 15/86* (2013.01); *C12N 2750/14121* (2013.01); *C12N 2750/14132* (2013.01); *C12N 2750/14141* (2013.01); *C12N 2750/14152* (2013.01)

(58) Field of Classification Search
None
See application file for complete search history.

(56) References Cited

U.S. PATENT DOCUMENTS

| | | | |
|---|---|---|---|
| 4,745,051 A | 5/1988 | Smith et al. | |
| 4,994,371 A | 2/1991 | Davie et al. | |
| 6,204,059 B1 | 3/2001 | Samulski et al. | |
| 6,221,349 B1 | 4/2001 | Couto et al. | |
| 6,531,298 B2 | 3/2003 | Stafford et al. | |
| 7,198,951 B2 | 4/2007 | Gao et al. | |
| 7,323,324 B2 | 1/2008 | Narimatsu et al. | |
| 7,531,341 B1 | 5/2009 | Vellard et al. | |
| 7,534,595 B2 | 5/2009 | Vellard et al. | |
| 7,537,923 B2 | 5/2009 | Kakkis et al. | |
| 7,560,263 B2 | 7/2009 | Kakkis et al. | |
| 7,566,462 B2 | 7/2009 | Jungles et al. | |
| 7,732,599 B2 | 6/2010 | Moser et al. | |
| 7,790,433 B2 | 9/2010 | Kakkis et al. | |
| 7,906,111 B2 | 3/2011 | Wilson et al. | |
| 8,003,126 B2 | 8/2011 | Jungles et al. | |
| 8,178,670 B2 | 5/2012 | Henderson et al. | |
| 9,249,405 B2 | 2/2016 | Simioni | |
| 9,393,323 B2 | 7/2016 | Nathwani et al. | |
| 9,447,168 B2 | 9/2016 | Nathwani et al. | |
| 9,504,762 B2 | 11/2016 | Colosi et al. | |
| 9,557,340 B2 | 1/2017 | Foehr et al. | |
| 9,695,220 B2 | 7/2017 | Vandenberghe et al. | |
| 10,512,675 B2 | 12/2019 | Bunting et al. | |
| 10,610,606 B2 | 4/2020 | Seymour et al. | |
| 2002/0031799 A1 | 3/2002 | Stafford et al. | |
| 2003/0138772 A1 | 7/2003 | Gao et al. | |
| 2003/0148506 A1 | 8/2003 | Kotin et al. | |
| 2003/0166284 A1 | 9/2003 | Srivastava et al. | |
| 2004/0142416 A1 | 7/2004 | Laipis et al. | |
| 2007/0243526 A1 | 10/2007 | Kay et al. | |
| 2008/0249052 A1 | 10/2008 | Duan et al. | |
| 2008/0269149 A1 | 10/2008 | Bowles et al. | |
| 2010/0129405 A1* | 5/2010 | Schmidt ................ | C12N 15/86 435/235.1 |
| 2010/0216709 A1 | 8/2010 | Scheule et al. | |
| 2011/0201088 A1 | 8/2011 | Beall et al. | |
| 2011/0244550 A1 | 10/2011 | Simioni | |
| 2013/0045186 A1 | 2/2013 | Gao et al. | |
| 2015/0071883 A1 | 3/2015 | Colosi | |
| 2015/0110858 A1 | 4/2015 | DeRosa et al. | |

(Continued)

FOREIGN PATENT DOCUMENTS

| | | |
|---|---|---|
| CN | 104293835 A | 1/2015 |
| CN | 105247044 A | 1/2016 |

(Continued)

OTHER PUBLICATIONS

Li et al, Site-Directed Mutagenesis of Surface Exposed Lysine Residues Leads to Improved Transduction by AAV2, But Not AAV8, Vectors in Murine Hepatocytes in Vivo. Human Gene Therapy Methods, 2015. 26(6): 211-220.*
Mietzsch et al. Completion of the AAV Structural Atlas: Serotype Capsid Structures Reveals Clade-Specific Features. Viruses, 2021: 13, 101. 15 pages.*
Paneda et al., Effect of Adeno-Associated Virus Serotype and Genomic Structure on Liver Transduction and Biodistribution in Mice of Both Genders. Human Gene Therapy, 2009. 20:908-917.*
Quinn et al. Intranasal Administration of Adeno-associated Virus Type 12 (AAV12) Leads to Transduction of Nasal Epithelia and Can Initiate Transgene-specific Immune Response. Molecular Therapy, 2011. 19(11): 1990-1998.*
Sen et al. Improved Adeno-Associated Virus (AAV) Serotype 1 and 5 Vectors for Gene Therapy. Scientific Reports, 2013. 3:1832, 6 pages.*

(Continued)

*Primary Examiner* — Allison M Fox
*Assistant Examiner* — Kimberly A Aron
(74) *Attorney, Agent, or Firm* — JONES DAY

(57) ABSTRACT

The invention relates to novel adeno-associated virus (AAV) capsid proteins, AAV particles comprising a novel capsid protein, polynucleotides encoding these capsid proteins and AAV vectors expressing these capsid proteins. The invention also relates to methods of making the herein described AAV vectors expressing the novel capsid proteins of the invention and associated therapeutic uses of thereof.

40 Claims, 11 Drawing Sheets
(4 of 11 Drawing Sheet(s) Filed in Color)

Specification includes a Sequence Listing.

(56) References Cited

U.S. PATENT DOCUMENTS

| | | | |
|---|---|---|---|
| 2015/0158930 A1 | 6/2015 | Nathwani et al. |
| 2016/0215024 A1 | 7/2016 | Vandenberghe et al. |
| 2017/0087219 A1 | 3/2017 | Bunting et al. |
| 2017/0119906 A1 | 5/2017 | Riley |
| 2017/0216408 A1 | 8/2017 | Anguela et al. |
| 2018/0105559 A1 | 4/2018 | Srivastava et al. |
| 2019/0078119 A1 | 3/2019 | Wilson et al. |
| 2019/0231901 A1 | 8/2019 | Seymour et al. |
| 2019/0376081 A1 | 12/2019 | Berguig et al. |
| 2020/0069819 A1 | 3/2020 | Colosi et al. |
| 2020/0362368 A1 | 11/2020 | Colosi et al. |
| 2021/0228738 A1 | 7/2021 | Lacroix-Desmazes et al. |

FOREIGN PATENT DOCUMENTS

| | | | |
|---|---|---|---|
| CN | 105579465 A | 5/2016 |
| EP | 127839 A2 | 12/1984 |
| EP | 155476 A1 | 9/1985 |
| EP | 127839 B1 | 7/1992 |
| JP | 2003235562 A | 8/2003 |
| JP | 2007507223 A | 3/2007 |
| RU | 2273645 C9 | 5/1999 |
| RU | 2228202 C2 | 5/2004 |
| RU | 2273645 C2 | 11/2006 |
| RU | 2502800 C2 | 12/2013 |
| RU | 2015144234 A | 4/2017 |
| RU | 2653444 C2 | 5/2018 |
| WO | WO 1996005309 A2 | 2/1996 |
| WO | WO 1996005309 A3 | 2/1996 |
| WO | WO-98/10088 A1 | 3/1998 |
| WO | WO 1999054440 A1 | 10/1999 |
| WO | WO 1999061601 A2 | 12/1999 |
| WO | WO 1999061601 A3 | 12/1999 |
| WO | WO 2001083692 A2 | 11/2001 |
| WO | WO 2001083692 A3 | 11/2001 |
| WO | WO 2003042397 A2 | 5/2003 |
| WO | WO 2003042397 A3 | 5/2003 |
| WO | WO-03/074714 A1 | 9/2003 |
| WO | WO 2003087383 A1 | 10/2003 |
| WO | WO 2005033321 A2 | 4/2005 |
| WO | WO 2005033321 A3 | 4/2005 |
| WO | WO 2006073496 A2 | 7/2006 |
| WO | WO 2006073496 A3 | 7/2006 |
| WO | WO 2006110689 A2 | 10/2006 |
| WO | WO 2006110689 A3 | 10/2006 |
| WO | WO 2006119432 A2 | 11/2006 |
| WO | WO 2006119432 A3 | 11/2006 |
| WO | WO 2009091912 A2 | 7/2009 |
| WO | WO 2009091912 A3 | 7/2009 |
| WO | WO 2010127097 A1 | 11/2010 |
| WO | WO 2011005968 A1 | 1/2011 |
| WO | WO 2011119773 A1 | 9/2011 |
| WO | WO 2011126808 A2 | 10/2011 |
| WO | WO 2011126808 A3 | 6/2012 |
| WO | WO 2011126808 A9 | 8/2012 |
| WO | WO 2013004943 A1 | 1/2013 |
| WO | WO 2013123503 A1 | 8/2013 |
| WO | WO 2013186563 A2 | 12/2013 |
| WO | WO 2013186563 A3 | 12/2013 |
| WO | WO 2014151341 A1 | 9/2014 |
| WO | WO 2014194132 A1 | 12/2014 |
| WO | WO 2015013313 A2 | 1/2015 |
| WO | WO 2015013313 A3 | 1/2015 |
| WO | WO 2015038625 A1 | 3/2015 |
| WO | WO 2015054653 A2 | 4/2015 |
| WO | WO 2015054653 A3 | 4/2015 |
| WO | WO 2015138348 A1 | 9/2015 |
| WO | WO 2015138357 A2 | 9/2015 |
| WO | WO 2015138357 A3 | 9/2015 |
| WO | WO 2015197869 A1 | 12/2015 |
| WO | WO 2016004318 A1 | 1/2016 |
| WO | WO 2016016119 A1 | 2/2016 |
| WO | WO 2016049230 A1 | 3/2016 |
| WO | WO 2016115382 A1 | 7/2016 |
| WO | WO 2016177911 A1 | 11/2016 |
| WO | WO 2017019994 A2 | 2/2017 |
| WO | WO 2017053677 A1 | 3/2017 |
| WO | WO-2017/066764 A2 | 4/2017 |
| WO | WO-2018/022608 A2 | 2/2018 |
| WO | WO 2018035213 A1 | 2/2018 |
| WO | WO 2018126112 A1 | 7/2018 |
| WO | WO 2018128689 A1 | 7/2018 |
| WO | WO 2019152841 A1 | 8/2019 |
| WO | WO 2019217513 A2 | 11/2019 |
| WO | WO 2019217513 A3 | 11/2019 |
| WO | WO 2019222132 A1 | 11/2019 |
| WO | WO 2020023612 A1 | 1/2020 |
| WO | WO 2020214929 A1 | 10/2020 |
| WO | WO 2020232044 A1 | 11/2020 |
| WO | WO 2021202943 A1 | 10/2021 |
| WO | WO 2023034980 A1 | 3/2023 |
| WO | WO 2023034989 A1 | 3/2023 |
| WO | WO 2023034990 A1 | 3/2023 |
| WO | WO 2023034994 A1 | 3/2023 |
| WO | WO 2023034996 A1 | 3/2023 |
| WO | WO 2023034997 A1 | 3/2023 |

OTHER PUBLICATIONS

Vercauteren et al. Superior In Vivo Transduction of Human Hepatocytes Using Engineered AAV3 Capsid. Molecular Therapy, 2016. 24(6): 1042-1049.*
Wang et al. Adeno-Associated Virus Serotype 8 Efficiently Delivers Genes to Muscle and Heart. Nature Biotechnology, 2005. 23(3): 321-328.*
Andersen et al., Herpesvirus-mediated gene delivery into the rat brain: specificity and efficiency of the neuron-specific enolase promoter, Cell Mol. Neurobiol., 13(5):503-15 (1993).
Arbuthnot et al., In vitro and in vivo hepatoma cell-specific expression of a gene transferred with an adenoviral vector, Hum. Gene Ther., 7(13):1503-14 (1996).
Boshart et al., A very strong enhancer is located upstream of an immediate early gene of human cytomegalovirus, Cell, 41(2):521-30 (1985).
Chen et al., Expression of rat bone sialoprotein promoter in transgenic mice, J. Bone Miner. Res., 11(5):654-64 (1996).
Chiorini et al., Cloning and characterization of adeno-associated virus type 5, J. Virol., 73(2):1309-19 (1999).
Chiorini et al., Cloning of adeno-associated virus type 4 (AAV4) and generation of recombinant AAV4 particles, J. Virol., 71(9):6823-33 (1997).
Chu et al., SV40 DNA transfection of cells in suspension: analysis of efficiency of transcription and translation of T-antigen, Gene, 13(2):197-202 (Mar. 1981).
Donnelly et al., The cleavage activities of aphthovirus and cardiovirus 2A proteins, J. Gen. Virol., 78(Pt. 1):13-21 (1997).
Furler et al., Recombinant AAV vectors containing the foot and mouth disease virus 2A sequence confer efficient bicistronic gene expression in cultured cells and rat substantia nigra neurons, Gene Ther., 8(11):864-73 (2001).
GenBank Accession No. AF028704.1, Adeno-associated virus 6, complete genome, Jan. 12, 1998.
GenBank Accession No. AF028705.1, Adeno-associated virus 3B, complete genome, Jan. 12, 1998.
GenBank Accession No. AX753250.1, Sequence 5 from Patent EP1310571, Jun. 23, 2003.
GenBank Accession No. AY631965.1, Adeno-associated virus 10 nonstructural protein and capsid protein genes, complete cds, Nov. 30, 2004.
GenBank Accession No. AY631966.1, Adeno-associated virus 11 nonstructural protein and capsid protein genes, complete cds, Nov. 30, 2004.
GenBank Accession No. DQ813647.1, Adeno-associated virus 12 Rep78 and VP1 genes, complete cds, Feb. 20, 2008.
GenBank Accession No. EU285562.1, Adeno-associated virus 13 nonstructural protein and capsid protein genes, complete cds, Sep. 23, 2008.
GenBank Accession No. NC_001401.2, Adeno-associated virus-2, complete genome, Aug. 13, 2018.

(56) References Cited

OTHER PUBLICATIONS

Genbank Accession No. NC_001729.1, Adeno-associated virus-3, complete genome, Aug. 13, 2018.
GenBank Accession No. NC_001829.1, Adeno-associated virus-4, complete genome, Aug. 13, 2018.
GenBank Accession No. NC_002077.1, Adeno-associated virus-1, complete genome, Aug. 13, 2018.
GenBank Accession No. NC_006152.1, Adeno-associated virus 5, complete genome, Aug. 13, 2018.
GenBank Accession No. NC_006260.1, Adeno-associated virus-7, complete genome, Aug. 13, 2018.
GenBank Accession No. NC_006261.1, Adeno-associated virus-8, complete genome, Aug. 13, 2018.
GenBank Accession No. AF043303.1 Adeno-associated virus 2, complete genome (May 2010).
GenBank Accession No. AF085716.1, Adeno-associated virus 5 DNA binding trs helicase (Rep22) and capsid protein (VP1) genes, complete cds (Feb. 1999).
GenBank Accession No. J01901.1, Adeno-associated virus 2, complete genome (Apr. 1993).
GenBank Accession No. U89790.1, Adeno-associated virus 4, complete genome (Aug. 1997).
Gossen et al., Tight control of gene expression in mammalian cells by tetracycline-responsive promoters, Proc. Natl. Acad. Sci. USA, 89(12):5547-51 (1992).
Gossen et al., Transcriptional activation by tetracyclines in mammalian cells, Science, 268(5218):1766-9 (1995).
Graham et al., A new technique for the assay of infectivity of human adenovirus 5 DNA, Virology, 5292):456-67 (Apr. 1973).
Hansal et al., Induction of Antigen-Specific Hyporesponsiveness by Transplantation of Hemopoietic Cells COntaining an MHC class I transgene regulated by a lymphocyte-specific promoter, J. Immunol., 161(3):1063-8 (Aug. 1998).
Harvey et al., Inducible control of gene expression: prospects for gene therapy, Curr. Opin. Chem. Biol., 2(4):512-8 (1998).
International Application No. PCT/US2019/032097, International Search Report and Written Opinion, dated Jan. 22, 2020.
Jacobs et al., Adeno-associated viral vectors for correction of inborn errors of metabolism: progressing towards clinical application, Curr. Pharm. Des., 17(24):2500-15 (2011).
Kirnbauer et al., Virus-like particles of bovine papillomavirus type 4 in prophylactic and therapeutic immunization, Virology, 219(1):37-44 (May 1996).
Klump et al., Retroviral vector-mediated expression of HoxB4 in hematopoietic cells using a novel coexpression strategy, Gene Ther., 8(10):811-7 (2001).
Kotin, Prospects for the use of adeno-associated virus as a vector for human gene therapy, Hum. Gene Ther., 5(7):793-801 (Jul. 1994).
Li et al., Synthetic muscle promoters: activities exceeding naturally occurring regulatory sequences, Nat. Biotechnol., 17(3):241-5 (1999).
Magari et al., Pharmacologic control of a humanized gene therapy system implanted into nude mice, J. Clin. Invest., 100(11):2865-72 (1997).
Miyatake et al., Transcriptional targeting of herpes simplex virus for cell-specific replication, J. Virol., 71(7):5124-32 (1997).
Muzyczka, Use of adeno-associated virus as a general transduction vector for mammalian cells, Curr. Top Microbiol. Immunol., 158:97-129 (1992).
Nathwani et al., Adenovirus-associated virus vector-mediated gene transfer in hemophilia B, N. Eng. J. Med., 365(25):2357-65 (Dec. 2011).
No et al., Ecdysone-inducible gene expression in mammalian cells and transgenic mice, Proc. Natl. Acad. Sci. USA, 93(8):3346-51 (1996).
Piccioli et al., Neuroantibodies: ectopic expression of a recombinant anti-substance P antibody in the central nervous system of transgenic mice, Neuron., 15(2):373-84 (1995).
Piccioli et al., Neuroantibodies: molecular cloning of a monoclonal antibody against substance P for expression in the central nervous system, Proc. Natl. Acad. Sci. USA, 88(13):5611-5 (1991).
Ruffing et al., Assembly of viruslike particles by recombinant structural proteins of adeno-associated virus type 2 in insect cells, J. Virol., 66(12):6922-30 (1992).
Ruffing et al., Mutations in the carboxy terminus of adeno-associated virus 2 capsid proteins affect viral infectivity: lack of an RGD integrin-binding motif, J. Gen. Virol., 75(Pt. 12):3385-92 (Dec. 1994).
Rutledge et al., Infectious clones and vectors derived from adeno-associated virus (AAV) serotypes other than AAV type 2, J. Virol., 72(1):309-19 (1998).
Sandig et al., HBV-derived promoters direct liver-specific expression of an adenovirally transduced LDL receptor gene, Gene Ther., 3(11):1002-9 (1996).
Sands, AAV-mediated liver-directed gene therapy, Methods Mol. Biol., 807:141-57 (2011).
Srivastava et al., Nucleotide sequence and organization of the adeno-associated virus 2 genome, J. Virol., 45(2):555-64 (Feb. 1983).
Stein et al., The osteocalcin gene: a model for multiple parameters of skeletal-specific transcriptional control, Mol. Biol. Rep., 24(3):185-96 (1997).
Wang et al., Ligand-inducible and liver-specific target gene expression in transgenic mice, Nat. Biotechnol., 15(3):239-43 (1997).
Wang et al., Positive and negative regulation of gene expression in eukaryotic cells with an inducible transcriptional regulator, Gene Ther., 4(5):432-41 (1997).
Wu et al., Mutational analysis of the adeno-associated virus type 2 (AAV2) capsid gene and construction of AAV2 vectors with altered tropism, J. Virol., 74(18):8635-47 (2000).
Zincarelli et al., Analysis of AAV serotypes 1-9 mediated gene expression and tropism in mice after systemic injection, Mol. Ther., 16(6):1073-80 (Jun. 2008).
Akinc et al., 2005, "Exploring polyethylenimine-mediated DNA transfection and the proton sponge hypothesis," J. Gene Med., 7(5):657-663.
Appel et al., 2014, "Nucleic acids: From A to Z," edited by S. Muller, p. 27 (in Russian with English translation).
Batts et al., 1995, "Chronic hepatitis. An update on terminology and reporting," Am. J. Surg. Pathol., 19(12):1409-1417.
Bedossa et al., 1996, "An algorithm for the grading of activity in chronic hepatitis C. The METAVIR Cooperative Study Group," Hepatology, 24(2):289-293.
Bello et al., 2014, "Novel adeno-associated viruses derived from pig tissues transduce most major organs in mice," Sci. Rep., 4:6644 (11 pages).
Berry et al., 2016, "Chemical Modulation of Endocytic Sorting Augments Adeno-associated Viral Transduction," J. Biol. Chem., 291(2):939-947 (Epub 2015).
Berry et al., 2016, "Modulation of intracellular calcium enhances AAV transduction in the CNS," Mol. Ther., 24 (Suppl 1): S14 (Abstract 30).
Bortolussi et al., 2014, "Life-long correction of hyperbilirubinemia with a neonatal liver-specific AAV-mediated gene transfer in a lethal mouse model of Crigler-Najjar Syndrome" Hum. Gene. Ther., 25(9):844-855.
Boutin et al., 2010, "Prevalence of serum IgG and neutralizing factors against adeno-associated virus (AAV) types 1, 2, 5, 6, 8, and 9 in the healthy population: implications for gene therapy using AAV vectors," Hum, Gene Ther., 21(6):704-712.
Bowles et al., 2003, "Marker rescue of adeno-associated virus (AAV) capsid mutants: a novel approach for chimeric AAV production," J. Virol., 77(1):423-432.
Brimble et al., 2016, "New and improved AAVenues: current status of hemophilia B gene therapy," Expert Opin. Biol. Ther., 16(1):79-92 (Epub 2015).
Burton et al., 2015, "A randomized, placebo-controlled, double-blind study of sapropterin to treat ADHD symptoms and executive function impairment in children and adults with sapropterin-responsive phenylketonuria," Mol. Genet. Metab., 114(3):415-424.
Calcedo et al., 2009, "Worldwide epidemiology of neutralizing antibodies to adeno-associated viruses," J. Infect. Dis., 199(3):381-390.

(56) References Cited

OTHER PUBLICATIONS

Calcedo et al., 2011, "Adeno-associated virus antibody profiles in newborns, children, and adolescents," Clin. Vaccine Immunol., 18(9):1586-1588.
Carbonell et al., 1988, "Synthesis of a gene coding for an insect-specific scorpion neurotoxin and attempts to express it using baculovirus vectors," Gene, 73(2):409-418.
Chahal et al., 2014, "Production of adeno-associated virus (AAV) serotypes by transient transfection of HEK293 cell suspension cultures for gene delivery," J. Virol. Methods, 196:163-173 (Epub 2013).
Chicoine et al., 2014, "Plasmapheresis eliminates the negative impact of AAV antibodies on microdystrophin gene expression following vascular delivery," Mol. Ther., 22(2):338-347 (Epub 2013).
Chow et al., 1991, "Characterization of a novel liver-specific enhancer in the human prothrombin gene," J. Biol. Chem., 266(28):18927-18933.
ClinicalTrials.gov Identifier NCT03952156, "Gene Therapy Clinical Study in Adult PKU (pheNIX)," last updated Mar. 26, 2021 (9 pages).
Colella et al., 2017, "Emerging Issues in AAV-Mediated In Vivo Gene Therapy," Mol. Ther. Methods Clin. Dev., 8:87-104.
Corti et al., 2014, "B-Cell Depletion is Protective Against Anti-AAV Capsid Immune Response: A Human Subject Case Study," Mol. Ther. Methods Clin. Dev., 1:14033 (7 pages).
Costa et al., 1988, "The cell-specific enhancer of the mouse transthyretin (prealbumin) gene binds a common factor at one site and a liver-specific factor(s) at two other sites," Mol. Cell Biol., 8(1):81-90.
Cunningham et al., 2008, "Gene Delivery to the Juvenile Mouse Liver Using AAV2/8 Vectors," Mol. Ther., 16(6):1081-1088 (Epub 2016).
Dabkowska et al., 2012, "The effect of neutral helper lipids on the structure of cationic lipid monolayers," J. R. Soc. Interface, 9(68):548-561.
Dang et al., 1995, "Structure of the hepatic control region of the human apolipoprotein E/C-I gene locus," J. Biol. Chem., 270(38):22577-22585.
De Simone et al., 1987, "Cis- and trans-acting elements responsible for the cell-specific expression of the human alpha 1-antitrypsin gene," EMBO J., 6(9):2759-2766.
Deverman et al., 2016, "Cre-dependent selection yields AAV variants for widespread gene transfer to the adult brain," Nat. Biotechnol., 34(2):204-209.
EBI Accession No. UniProt A0A0K1P7V4, Capside Protein, Nov. 11, 2015 (1 page).
Eisensmith et al., 1996, "Somatic gene therapy for phenylketonuria and other hepatic deficiencies," J. Inherit Metab. Dis., 19(4):412-423.
Fagiuoli et al., 2013, "Monogenic diseases that can be cured by liver transplantation," J. Hepatol., 59(3):595-612.
Falese et al., 2017, "Strategy to detect pre-existing immunity to AAV gene therapy," Gene. Ther., 24(12):768-778.
Fang et al., 1994, "Gene therapy for phenylketonuria: phenotypic correction in a genetically deficient mouse model by adenovirus-mediated hepatic gene transfer," Gene Ther., 1(4):247-254.
Frain et al., 1990, "Binding of a liver-specific factor to the human albumin gene promoter and enhancer," Mol. Cell Biol., 10(3):991-999.
Friesen et al., 1986, "The regulation of baculovirus gene expression," Curr. Top. Microbiol. Immunol., 131:31-49.
Fu et al., 2017, "Differential Prevalence of Antibodies Against Adeno-Associated Virus in Healthy Children and Patients with Mucopolysaccharidosis III: Perspective for AAV-Mediated Gene Therapy," Hum. Gene. Ther. Clin. Dev., 28(4):187-196.
Gao et al., 2003, "Adeno-associated viruses undergo substantial evolution in primates during natural infections," Proc. Natl. Acad. Sci. USA, 100(10):6081-6086.
Gao et al., 2004, "Clades of Adeno-associated viruses are widely disseminated in human tissues," J. Virol., 78(12):6381-6388.

Gao et al., 2011, "Exploiting natural diversity of AAV for the design of vectors with novel properties," Methods Mol. Biol., 807:93-118.
GenBank Accession No. AAB95450.1, "capsid protein VP1 [Adeno-associated virus-6]," Jan. 12, 1998 (2 pages).
GenBank Accession No. AAB95452.1, "capsid protein VP1 [Adeno-associated virus 3B]," Jan. 12, 1998 (2 pages).
GenBank Accession No. AAT46337.1, "capsid protein [Adeno-associated virus 10]," Nov. 30, 2004 (2 pages).
GenBank Accession No. AAT46339.1, "capsid protein [Adeno-associated virus 11]," Nov. 30, 2004 (2 pages).
GenBank Accession No. ABI16639.1, "VP1 [Adeno-associated virus 12]," Feb. 20, 2008 (2 pages).
GenBank Accession No. ABZ10812.1, "capsid protein [Adeno-associated virus 13]," Sep. 23, 2008 (2 pages).
GenBank Accession No. HZ323618.1, "JP 2015518705-A/1411: Modified Polynucleotides for the Production of Biologies and Proteins Associated with Human Disease," Nov. 26, 2015 (2 pages).
GenBank Accession No. JC111928.1, "Sequence 573 from Patent WO2013151666," Jan. 28, 2014 (2 pages).
GenBank Accession No. NP_043941.1, "capsid protein [Adeno-associated virus-3]," Aug. 13, 2018 (2 pages).
GenBank Accession No. NP_044927.1, "capsid [Adeno-associated virus-4]," Aug. 13, 2018 (2 pages).
GenBank Accession No. YP_068409.1, "capsid protein [Adeno-associated virus-5]," Aug. 13, 2018 (2 pages).
GenBank Accession No. YP_077178.1, "capsid protein [Adeno-associated virus-7]," Aug. 13, 2018 (2 pages).
GenBank Accession No. YP_077180.1, "capsid protein [Adeno-associated virus-8]," Aug. 13, 2018 (2 pages).
GenBank Accession No. YP_680426.1, "major coat protein VP1 [Adeno-associated virus-2]," Aug. 13, 2018 (2 pages).
George et al., 2017, "Hemophilia B Gene Therapy with a High-Specific-Activity Factor IX Variant," N. Engl. J. Med., 377(23):2215-2227.
Ghosh et al., 2007, "Expanding adeno-associated viral vector capacity: a tale of two vectors," Biotechnol. Genet. Eng. Rev., 24:165-177.
Gibson et al., 2009, "Enzymatic assembly of DNA molecules up to several hundred kilobases," Nat. Methods, 6(5):343-345 and Online Methods.
Gibson et al., 2011, "Enzymatic assembly of overlapping DNA fragments," Methods Enzymol., 498:349-361.
Gnirke et al., 2009, "Solution hybrid selection with ultra-long oligonucleotides for massively parallel targeted sequencing," Nat. Biotechnol., 27(2):182-189.
Greenberg et al., 2016, "Prevalence of AAV1 neutralizing antibodies and consequences for a clinical trial of gene transfer for advanced heart failure," Gene. Ther., 23(3):313-319 (Epub 2015).
Grimm et al., 2008, "In vitro and in vivo gene therapy vector evolution via multispecies interbreeding and retargeting of adeno-associated viruses," J. Virol., 82(12):5887-5911.
Grosse et al., 2017, "Relevance of Assembly-Activating Protein for Adeno-associated Virus Vector Production and Capsid Protein Stability in Mammalian and Insect Cells," J. Virol., 91(20):e01198-17 (30 pages).
Halbert et al., 2000, "Repeat transduction in the mouse lung by using adeno-associated virus vectors with different serotypes," J. Virol., 74(3): 1524-1532.
Halbert et al., 2006, "Prevalence of neutralizing antibodies against adeno-associated virus (AAV) types 2, 5, and 6 in cystic fibrosis and normal populations: Implications for gene therapy using AAV vectors," Hum. Gene. Ther., 17(4):440-447.
Harding et al., 2006, "Complete correction of hyperphenylalaninemia following liver-directed, recombinant AAV2/8 vector-mediated gene therapy in murine phenylketonuria," Gene Ther., 13(5):457-462.
Harding, 2008, "Progress toward cell-directed therapy for phenylketonuria," Clin. Genet., 74(2):97-104.
Harris et al., 2011, "Comparison of a fluorogenic anti-FXa assay with a central laboratory chromogenic anti-FXa assay for measuring LMWH activity in patient plasmas," Thromb. Res., 128(6):e125-e129.
Hauck et al., 2003, "Characterization of tissue tropism determinants of adeno-associated virus type 1," J. Virol., 77(4):2768-2774.

(56) References Cited

OTHER PUBLICATIONS

Hill et al., 1965, "An automated procedure for blood phenylalanine," Clin. Chem., 11:541-546.
Hinderer et al., 2018, "Severe Toxicity in Nonhuman Primates and Piglets Following High-Dose Intravenous Administration of an Adeno-Associated Virus Vector Expressing Human SMN," Hum. Gene. Ther., 29(3):285-298.
H1rosue et al., 2007, "Effect of inhibition of dynein function and microtubule-altering drugs on AAV2 transduction," Virology, 367(1):10-18.
Hirsch et al., 2010, "Little vector, big gene transduction: fragmented genome reassembly of adeno-associated virus," Mol. Ther., 18(1):6-8.
Hurlbut et al., 2010, "Preexisting immunity and low expression in primates highlight translational challenges for liver-directed AAV8-mediated gene therapy," Mol. Ther., 18(11):1983-1994.
International Search Report and Written Opinion for International Patent Application No. PCT/US2017/043703 (Pub No. WO 2018022608) dated Feb. 7, 2018 (19 pages).
International Search Report and Written Opinion for International Patent Application No. PCT/US2019/031252 (Pub No. WO 2019217513) dated Nov. 20, 2019 (21 pages).
International Search Report and Written Opinion for International Patent Application No. PCT/US2019/032092 (Pub No. WO 2019222132) dated Oct. 28, 2019 (21 pages).
International Search Report and Written Opinion for International Patent Application No. PCT/US2020/032560 (Pub No. WO 2020232044) dated Sep. 22, 2020 (11 pages).
International Search Report and Written Opinion for International Patent Application No. PCT/US2021/025486 dated Sep. 10, 2021 (20 pages).
Invitation to Pay Additional Fees accompanying Partial International Search Report and Provisional Opinion for International Patent Application No. PCT/US2019/032092 (Pub No. WO 2019222132) dated Sep. 9, 2019 (13 pages).
Invitation to Pay Additional Fees accompanying Partial International Search Report and Provisional Opinion for International Patent Application No. PCT/US2021/025486 dated Jul. 20, 2021 (15 pages).
Kajigaya et al., 1991, "Self-assembled B19 parvovirus capsids, produced in a baculovirus system, are antigenicalty and immunogenicalty similar to native virions," Proc. Natl. Acad. Sci. USA, 88(11):4646-4650.
Kato et al., 2010, "Silkworm expression system as a platform technology in life science," Appl. Microbiol. Biotechnol., 85(3):459-470.
Khan et al., 2019, "The phenylketonuria-associated substitution R68S converts phenylalanine hydroxylase to a constitutively active enzyme but reduces its stability," J. Biol. Chem., 294(12):4359-4367.
Kim et al., 1997, "Codon optimization for high-level expression of human erythropoietin (EPO) in mammalian cells," Gene, 199(1-2):293-301.
Knappskog et al., 1997, "Effect of mutations at Cys237 on the activation state and activity of human phenylalanine hydroxylase," FEBS Lett., 409(1):7-11.
Kok et al., 2013, "Adeno-associated virus-mediated rescue of neonatal lethality in argininosuccinate synthetase-deficient mice," Mol. Ther., 21(10):1823-1831.
Kurachi et al., 1995, "Role of intron I in expression of the human factor IX gene," J. Biol. Chem., 270(10):5276-5281.
La Du et al., 1963, "A quantitative micromethod for the determination of phenylalanine and tyrosine in blood and its application in the diagnosis of phenylketonuria in infants," Pediatrics, 31:39-46.
Laipis et al., 2003, "Recombinant AAV-based gene therapy of phenylketonuria in the Pah (enu2) missense mutant mouse," Mol. Ther., 7:S391-S392.
Lambert et al., 1995, "Regional 5-hydroxyindoleacetic acid production in humans," Life Sci., 57(3):255-267.

Lebacq-Veheyden et al., 1988, "Posttranslational processing of endogenous and of baculovirus-expressed human gastrin-releasing peptide precursor," Mol. Cell Biol., 8(8):3129-3135.
Li et al., 2012, "Neutralizing antibodies against adeno-associated virus examined prospectively in pediatric patients with hemophilia," Gene. Ther., 19(3):288-294.
Liu et al., 2013, "A practical guide to the monitoring and management of the complications of systemic corticosteroid therapy," Allergy Asthma Clin. Immunol., 9(1):30 (25 pages).
Liu et al., 2014, "Neutralizing antibodies against AAV2, AAV5 and AAV8 in healthy and HIV-1-infected subjects in China: implications for gene therapy using AAV vectors," Gene. Ther., 21(8):732-738.
Luckow et al., 1988, "Trends in the development of baculovirus expression vectors," Nature Biotechnol., 6:47-55.
Maeda et al., 1985, "Production of human alpha-interferon in silkworm using a baculovirus vector," Nature, 315(6020):592-594.
Majowicz et al., 2017, "Successful Repeated Hepatic Gene Delivery in Mice and Non-human Primates Achieved by Sequential Administration of AAV5 ch and AAV1," Mol. Ther., 25(8):1831-1842.
Manno et al., 2006, "Successful transduction of liver in hemophilia by AAV-Factor IX and limitations imposed by the host immune response," Nat. Med., 12(3):342-347 with Erratum and Corrigendum.
Marsic et al., 2014, "Vector design Tour de Force: integrating combinatorial and rational approaches to derive novel adeno-associated virus variants," Mol. Ther., 22(11): 1900-1909.
Martin et al., 1988, "Glycosylation and processing of high levels of active human glucocerebrosidase in invertebrate cells using a baculovirus expression vector," DNA, 7(2):99-106.
Mas At et al., 2013, "Humoral immunity to AAV vectors in gene therapy: challenges and potential solutions," Discov. Med., 15(85):379-389.
Mays et al., 2013, "Mapping the stiuctural determinants responsible for enhanced T cell activation to the immunogenic adeno-associated virus capsid from isolate rhesus 32.33," J. Virol., 87(17):9473-9485.
Mccaman et al., 1962, "Fluorimetric method for the determination of phenylalanine in serum," J. Lab. Clin. Med., 59(5):885-890.
Mcintosh et al., 2012, "Successful attenuation of humoral immunity to viral capsid and transgenic protein following AAV-mediated gene transfer with a non-depleting CD4 antibody and cyclosporine," Gene. Ther., 19(1):78-85 (Epub 2011).
McIntosh et al., 2013, "Therapeutic levels of FVIII following a single peripheral vein administration of rAAV vector encoding a novel human factor VIII variant," Blood, 121(17):3335-3344.
McKenna et al., 1998, "Establishment of NewTrichoplusia niCell Lines in Serum-Free Medium for Baculovirus and Recombinant Protein Production," J. Invertebrate Pathology, 71(1):82-90.
Meadows et al., 2019, "Threshold for Pre-existing Antibody Levels Limiting Transduction Efficiency of Systemic rAAV9 Gene Delivery: Relevance for Translation," Mol. Ther. Methods Clin. Dev., 13:453-462.
Meliani et al., 2015, "Determination of anti-adeno-associated virus vector neutralizing antibody titer with an in vitro reporter system," Hum. Gene. Ther. Methods, 26(2):45-53.
Mendell et al., 2017, "Single-Dose Gene-Replacement Therapy for Spinal Muscular Atrophy" N. Engl. J. Med., 377:1713-1722.
Merrifield, 1963, "Solid Phase Peptide Synthesis. I. The Synthesis of a Tetrapeptide," J. Am. Chem. Soc., 85(14):2149-2154.
Miao et al., 2000, "Inclusion of the hepatic locus control region, an intron, and untranslated region increases and stabilizes hepatic factor IX gene expression in vivo but not in vitro," Mol. Ther., 1(6):522-532.
Miesbach et al., 2018, "Gene therapy with adeno-associated virus vector 5-human factor IX in adults with hemophilia B," Blood, 131(9):1022-1031 (Epub 2017).
Mietzsch et al., 2014, "OneBac: platform for scalable and high-titer production of adeno-associated virus serotype 1-12 vectors for gene therapy," Hum. Gene. Ther., 25(3):212-222.
Miller, 1988, "Baculoviruses as gene expression vectors," Annu. Rev. Microbiol., 42:177-199.
Mingozzi et al., 2007, "CD8(+) T-cell responses to adeno-associated virus capsid in humans," Nat. Med., 13(4):419-422.

(56) References Cited

OTHER PUBLICATIONS

Mingozzi et al., 2012, "Pharmacological modulation of humoral immunity in a nonhuman primate model of AAV gene transfer for hemophilia B," Mol. Ther., 20(7):1410-1416.
Mingozzi et al., 2013, "Prevalence and pharmacological modulation of humoral immunity to AAV vectors in gene transfer to synovial tissue," Gene. Ther., 20(4):417-424 (Epub 2012).
Mingozzi et al., 2017, "Overcoming the Host Immune Response to Adeno-Associated Virus Gene Delivery Vectors: The Race Between Clearance, Tolerance, Neutralization, and Escape," Annu. Rev. Virol., 4(1):511-534.
Mitchell et al., 2013, "Arsenic trioxide stabilizes accumulations of adeno-associated virus virions at the perinuclear region, increasing transduction in vitro and in vivo," J. Virol., 87(8):4571-4583.
Mitchell et al., 2013, "Mechamstic insights into the enhancement of adeno-associated virus transduction by proteasome inhibitors," J. Virol., 87(23):13035-13041.
Miyajima et al., 1987, "Use of the silkworm, Bombyx mori, and an insect baculovirus vector for high-level expression and secretion of biologically active mouse interleukin-3," Gene, 58(2-3):273-281.
Miyamoto et al., 1957, "Competitive inhibition of mammalian tyrosinase by phenylalanine and its relationship to hair pigmentation in phenylketonuria," Nature, 179(4552): 199-200.
Mochizuki et al., 2004, "Adeno-associated virus (AAV) vector-mediated liver- and muscle-directed transgene expression using various kinds of promoters and serotypes," Gene. Ther. Mol. Biol., 8:9-18.
Mochizuki et al., 2004, "Long-term correction of hyperphenylalaninemia by AAV-mediated gene transfer leads to behavioral recovery in phenylketonuria mice," Gene. Ther., 11(13):1081-1086.
Moskalenko et al., 2000, "Epitope mapping of human anti-adeno-associated virus type 2 neutralizing antibodies: implications for gene therapy and virus structure," J. Virol., 74(4):1761-1766.
Muyldermans et al., 2001, "Single domain camel antibodies: current status," J. Biotechnol., 74(4):277-302.
Nagasaki et al., 1999, "Reversal of hypopigmentation in phenylketonuria mice by adenovirus-mediated gene transfer," Pediatr. Res., 45:465-473.
Nathwani et al., 2006, "Self-complementary adeno-associated virus vectors containing a novel liver-specific human factor IX expression cassette enable highly efficient transduction of murine and nonhuman primate liver," Blood, 107(7):2653-2661.
Nathwani et al., 2007, "Safe and efficient transduction of the liver after peripheral vein infusion of self-complementary AAV vector results in stable therapeutic expression of human FIX in nonhuman primates," Blood, 109(4):1414-1421.
Nathwani et al., 2014, "Long-term safety and efficacy of factor IX gene therapy in hemophilia B," N. Engl. J. Med., 371(21):1994-2004.
Nonnenmacher et al., 2012, "Intracellular transport of recombinant adeno-associated virus vectors," Gene. Ther., 19(6):649-658.
Oh et al., 2004, "Long-term enzymatic and phenotypic correction in the phenylketonuria mouse model by adeno-associated virus vector-mediated gene transfer," Pediatr. Res., 56(2):278-284.
Ojala et al., 2018, "In Vivo Selection of a Computationally Designed SCHEMA AAV Library Yields a Novel Variant for Infection of Adult Neural Stem Cells in the SVZ," Mol. Ther., 26(1):304-319 (Epub 2017).
Okuyama et al., 1996, "Liver-directed gene therapy: a retroviral vector with a complete LTR and the ApoE enhancer-alpha 1-antitrypsin promoter dramatically increases expression of human alpha 1-antitrypsin in vivo," Hum. Gene Ther., 7(5):637-645.
Olson et al., 1998, "College of American Pathologists Conference XXXI on laboratory monitoring of anticoagulant therapy: laboratory monitoring of unfractionated heparin therapy," Arch. Pathol. Lab. Med., 122(9):782-798.
Peden et al., 2009, "Striatal readministration of rAAV vectors reveals an immune response against AAV2 capsids that can be circumvented," Mol. Ther., 17(3):524-537.

Peterson et al., 1988, "Blood phenylalanine estimation for the patient with phenylketonuria using a portable device," Biochem. Med. Metab. Biol., 39(1):98-104.
Pey et al., 2008, "Identification of pharmacological chaperones as potential therapeutic agents to treat phenylketonuria," J. Clin. Invest., 118(8):2858-2867.
Rangarajan et al., 2017, "AAV5-Factor VIII Gene Transfer in Severe Hemophilia A," N. Engl. J. Med., 377(26):2519-2530.
Rodrigues et al., 2018, "Pharmaceutical Development of AAV-Based Gene Therapy Products for the Eye," Pharm. Res., 36(2):29 (20 pages).
Ronzitti et al., 2016, "A translationally optimized AAV-UGT1A1 vector drives safe and long-lasting correction of Crigler-Najjar syndrome," Mol. Ther. Methods Clin. Dev., 3:16049 (10 pages).
Rouet et al., 1992, "A potent enhancer made of clustered liver-specific elements in the transcription control sequences of human alpha 1-microglobulin/bikunin gene," J. Biol. Chem., 267(29):20765-20773.
Rouet et al., 1995, "Hierarchy and positive/negative interplays of the hepatocyte nuclear factors HNF-1, -3 and -4 in the liver-specific enhancer for the human alpha-1-microglobulin/bikunin precursor," Nucleic Acids Res., 23(3):395-404.
Rouet et al., 1998, "An array of binding sites for hepatocyte nuclear factor 4 of high and low affinities modulates the liver-specific enhancer for the human alphal-microglobulin/bikunin precursor," Biochem. J., 334 (Pt 3):577-584.
Ruddell et al., 2008, "The function of serotonin within the liver," J. Hepatol., 48(4):666-675.
Rudy et al., 1987, "Phenylalanine and tyrosine in serum and eluates from dried blood spots as determined by reversed-phase liquid chromatography," Clin. Chem., 33(7):1152-1154.
Russell et al., 2017, "Efficacy and safety of voretigene neparvovec (AAV2-hRPE65v2) in patients withRPE65-mediated inherited retinal dystrophy: a randomised, controlled, open-label, phase 3 trial," Lancet, 390(10097):849-860.
Samulski et al., 1989, "Helper-free stocks of recombinant adeno-associated viruses: normal integration does not require viral gene expression," J. Virol., 63(9):3822-3828.
Sandberg et al., 2001, "Structural and functional characteristics of the B-domain-deleted recombinant factor VIII protein, r-VIII SQ," Thromb. Haemost., 85(1):93-100.
Santos-Sierra et al., 2012, "Novel pharmacological chaperones that correct phenylketonuria in mice," Hum. Mol. Genet., 21(8):1877-1887.
Sawin et al., 2014, "Differential effects of low-phenylalanine protein sources on brain neurotransmitters and behavior in C57B1/6-Pah(enu2) mice," Mol. Genet. Metab., 111(4):452-461.
Scallan et al., 2006, "Human immunoglobulin inhibits liver transduction by AAV vectors at low AAV2 neutralizing titers in SCID mice," Blood, 107(5):1810-1817 (Epub 2005).
Schnepp et al., 2005, "Characterization of adeno-associated virus genomes isolated from human tissues," J. Virol., 79(23):14793-14803.
Schuck et al., 2015, "Phenylketonuria Pathophysiology: on the Role of Metabolic Alterations," Agind Dis., 6(5):390-399.
Shachter et al., 1993, "Localization of a liver-specific enhancer in the apolipoprotein E/C-I/C-II gene locus," J. Lipid Res., 34(10):1699-1707.
Sharp et al., 1987, "The codon Adaptation Index—a measure of directional synonymous codon usage bias, and its potential applications," Nucleic Acids Res., 15(3):1281-1295.
Shedlovsky et al., 1993, "Mouse models of human phenylketonuria," Genetics, 134(4):1205-1210.
Shen et al., 2007, "Characterization of the relationship of AAV capsid domain swapping to liver transduction efficiency," Mol. Ther., 15(11):1955-1962.
Smith et al., 1985, "Modification and secretion of human interleukin 2 produced in insect cells by a baculovirus expression vector," Proc. Natl. Acad. Sci. USA, 82(24):8404-8408.
Soriano et al., 2002, "Gene therapy and pediatric liver disease," J. Pediatr. Gastroenterol. Nutr., 35 Suppl 1:S51-S54.
Sun et al., 2013, "Assessment of a passive immunity mouse model to quantitatively analyze the impact of neutralizing antibodies on

(56) References Cited

OTHER PUBLICATIONS adeno-associated virus-mediated gene transfer," J. Immunol. Methods, 387(1-2):114-120 (Epub 2012).

Svyatchenko et al., 2012, "Oncolytic Adenoviruses in Anti-Cancer Therapy: Current Status and Perspectives," Molekuliamaia Biologiia, 46(4):556-569 (in Russian with English abstract).

Thomas et al., 2018, "Pegvaliase for the treatment of phenylketonuria: Results of a long-term phase 3 clinical trial program (PRISM)," Mol. Genet. Metab., 124(1):27-38.

Tsukerman, 1985, "Simple method of mass screening for phenylketonuria," Lab. Delo., 6:326-327 (in Russian with English abstract).

Viecelli et al., 2014, "Treatment of phenylketonuria using minicircle-based naked-DNA gene transfer to murine liver," Hepatology, 60(3):1035-1043.

Viecelli et al., 2016, "Minicircles show improved hepatic expression of their transgene from a natural endogenous promoter and are lost upon partial hepatectomy due to the episomal nature of the vector," Mol. Ther., 24(1):S142.

Virella-Lowell et al., 2000, "Inhibition of recombinant adeno-associated virus (rAAV) transduction by bronchial secretions from cystic fibrosis patients," Gene. Ther., 7(20):1783-1789.

Vlak et al., 1988, "Functional studies on the p10 gene of Autographa californica nuclear polyhedrosis virus using a recombinant expressing a p10-beta-galactosidase fusion gene," J. Gen. Virol., 69:765-776.

Wang et al., 1999, "Sustained correction of bleeding disorder in hemophilia B mice by gene therapy," Proc. Natl. Acad. Sci. USA, 96(7):3906-3910.

Wang et al., 2001, "Mutagenesis of the regulatory domain of phenylalanine hydroxylase," Proc. Natl. Acad. Sci. USA, 98(4):1537-1542.

Wang et al., 2010, "The pleiotropic effects of natural AAV infections on liver-directed gene transfer in macaques," Mol. Ther., 18(1):126-134 (Epub 2009).

Wang et al., 2012, "Hepatic gene transfer in neonatal mice by adeno-associated virus serotype 8 vector," Hum. Gene. Ther., 23(5):533-539.

Ward et al., 2011, "Codon optimization of human factor VIII cDNAs leads to high-level expression," Blood, 117(3):798-807 (Epub 2010).

Weinberg et al., 2014, "Recombinant adeno-associated virus utilizes cell-specific infectious entry mechanisms," J. Virol., 88(21):12472-12484.

Winn et al., 2018, "Blood phenylalanine reduction corrects CNS dopamine and serotonin deficiencies and partially improves behavioral performance in adult phenylketonuric mice," Mol. Genet. Metab., 123(1):6-20.

Wong et al., 2016, "Benzoyl chloride derivatization with liquid chromatography-mass spectrometry for targeted metabolomics of neurochemicals in biological samples," J. Chromatogr. A., 1446:78-90.

Yan et al., 2005, "Inverted terminal repeat sequences are important for intermolecular recombination and circularization of adeno-associated virus genomes," J. Virol., 79(1):364-379.

Yan et al., 2012, "Human thyroxine binding globulin (TBG) promoter directs efficient and sustaining transgene expression in liver-specific pattern," Gene, 506(2):289-294.

Yano et al., 2016, "Evaluation of Tetrahydrobiopterin Therapy with Large Neutral Amino Acid Supplementation in Phenylketonuria: Effects on Potential Peripheral Biomarkers, Melatonin and Dopamine, for Brain Monoamine Neurotransmitters," PLoS One, 11(8):e0160892 (14 pages).

Zhao et al., 2000, "BPV1 E2 protein enhances packaging of full-length plasmid DNA in BPV1 pseudovirions," Virology, 272(2):382-393.

Zinn et al., 2015, "In Silico Reconstruction of the Viral Evolutionary Lineage Yields a Potent Gene Therapy Vector," Cell Rep., 12(6):1056-1068.

Zur Megede et al., 2000, "Increased expression and immunogenicity of sequence-modified human immunodeficiency virus type 1 gag gene," J. Virol., 74(6):2628-263 5.

Hafid et al., 2015, "Phenylketonuria: a review of current and future treatments," Transl. Pediatr., 4(4):304-317.

GenBank Accession No. AAS99254.1, "capsid protein VP1 [Adeno-associated virus]," Jun. 24, 2004 (2 pages).

GenBank Accession No. ACB55317.1, "capsid protein VP1, partial (endogenous virus) [Adeno-associated virus]," Jul. 31, 2008 (2 pages).

Govindasamy et al., 2013, "Structural insights into adeno-associated virus serotype 5," J. Virol., 87(20):11187-11199.

Hildebrandt et al., 2020, "Evolution of dependoparvoviruses across geological timescales-implications for design of AAV-based gene therapy vectors," Virus Evol., 6(2):veaa043 (14 pages).

Drouin et al., 2013, "Adeno-associated virus structural biology as a tool in vector development," Future Virol., 8(12):1183-1199.

\* cited by examiner

| Capsid | Brain | Eyes | Lung | Heart | Liver | Pancreas | Spleen | Kidney | Front Limb |
|---|---|---|---|---|---|---|---|---|---|
| Bba 45 | 1.14E+05 | 5.62E+04 | 8.18E+06 | 2.65E+05 | 3.50E+07 | 2.46E+05 | 2.40E+05 | 1.54E+05 | 1.64E+04 |
|  | 6.38E+04 | 3.15E+04 | 7.27E+05 | 1.25E+05 | 1.81E+07 | 1.69E+05 | 1.43E+05 | 9.09E+04 | 1.49E+04 |
| Bba 46 | 2.01E+05 | 9.29E+04 | 8.73E+06 | 4.18E+05 | 1.90E+08 | 8.64E+05 | 3.94E+05 | 3.85E+05 | 4.14E+04 |
|  | 8.32E+04 | 8.42E+04 | 4.80E+06 | 2.07E+05 | 2.30E+08 | 9.18E+05 | 3.50E+05 | 3.46E+05 | 1.16E+04 |
| Bba 47 | 1.51E+05 | 7.63E+04 | 7.05E+06 | 2.97E+05 | 6.87E+07 | 4.79E+05 | 5.14E+05 | 2.62E+05 | 3.11E+04 |
|  | 5.43E+04 | 2.72E+04 | 1.90E+06 | 1.37E+05 | 5.62E+07 | 1.62E+05 | 8.02E+04 | 1.07E+05 | 2.11E+04 |
| Bba 49 | 2.93E+05 | 9.94E+04 | 9.33E+06 | 3.79E+05 | 1.73E+08 | 9.37E+05 | 3.14E+04 | 4.76E+05 | 1.63E+05 |
|  | 3.09E+05 | 1.06E+05 | 3.11E+06 | 1.61E+05 | 2.64E+08 | 1.19E+06 | 8.33E+05 | 6.08E+05 | 1.26E+05 |
| Bba 50 | 7.14E+04 | 4.63E+04 | 1.43E+06 | 1.15E+05 | 2.23E+07 | 1.27E+05 | 1.04E+05 | 8.85E+04 | 2.01E+04 |
|  | 5.18E+04 | 4.49E+04 | 5.57E+05 | 3.30E+04 | 8.36E+06 | 4.32E+04 | 1.33E+04 | 5.76E+04 | 2.42E+04 |
| Bba 51 | 1.65E+05 | 7.31E+04 | 1.33E+07 | 2.86E+05 | 4.15E+07 | 3.97E+05 | 2.19E+05 | 2.04E+05 | 5.97E+04 |
|  | 5.67E+04 | 3.54E+04 | 4.31E+06 | 1.07E+05 | 2.03E+07 | 1.02E+05 | 9.78E+04 | 5.68E+04 | 5.30E+04 |

| Capsid | Quadriceps | Gastrocnemius | Tibialis Anterior | Diaphragm | Tongue | Skin | Masseter MS | Lymph Nodes | Soleus |
|---|---|---|---|---|---|---|---|---|---|
| Bba 45 | 8.99E+04 | 2.16E+05 | 5.43E+04 | 3.02E+05 | 8.17E+04 | 6.34E+04 | 3.73E+04 | 5.51E+05 | 1.91E+04 |
|  | 5.25E+04 | 1.53E+05 | 4.61E+04 | 1.82E+05 | 5.69E+04 | 3.72E+04 | 2.24E+04 | 3.63E+05 | 1.12E+04 |
| Bba 46 | 2.01E+06 | 2.06E+06 | 1.66E+05 | 5.36E+05 | 7.97E+04 | 1.30E+05 | 4.57E+05 | 4.80E+05 | 6.68E+04 |
|  | 1.59E+06 | 1.45E+06 | 1.57E+05 | 3.35E+05 | 5.13E+05 | 9.52E+04 | 1.73E+05 | 2.49E+05 | 6.88E+04 |
| Bba 47 | 1.49E+06 | 3.41E+06 | 1.88E+05 | 6.09E+05 | 1.49E+05 | 1.43E+05 | 5.88E+05 | 7.64E+05 | 8.99E+04 |
|  | 1.52E+06 | 3.24E+06 | 1.88E+05 | 4.00E+05 | 1.09E+05 | 1.14E+05 | 2.69E+05 | 2.20E+05 | 8.91E+04 |
| Bba 49 | 1.13E+07 | 6.32E+06 | 8.79E+05 | 1.35E+06 | 1.52E+05 | 2.43E+05 | 1.28E+06 | 1.09E+06 | 1.68E+05 |
|  | 6.06E+06 | 2.70E+06 | 9.40E+05 | 7.73E+05 | 5.83E+04 | 5.40E+04 | 4.00E+05 | 6.45E+05 | 1.42E+05 |
| Bba 50 | 1.92E+06 | 2.44E+06 | 7.94E+04 | 1.37E+05 | 1.88E+05 | 7.42E+04 | 2.34E+04 | 1.18E+05 | 2.42E+04 |
|  | 3.00E+06 | 8.57E+05 | 5.74E+04 | 4.95E+04 | 9.97E+04 | 1.88E+04 | 1.69E+04 | 4.21E+04 | 1.17E+04 |
| Bba 51 | 2.72E+06 | 3.15E+06 | 1.23E+05 | 2.85E+05 | 1.30E+05 | 1.46E+05 | 7.69E+04 | 5.13E+05 | 5.32E+04 |
|  | 1.67E+06 | 3.22E+06 | 7.77E+04 | 1.40E+05 | 5.05E+04 | 1.06E+05 | 3.79E+04 | 2.63E+05 | 3.70E+04 |

Figure 1

SEQUENCE LISTING

```
<160> NUMBER OF SEQ ID NOS: 14

<210> SEQ ID NO 1
<211> LENGTH: 742
<212> TYPE: PRT
<213> ORGANISM: Papio
<220> FEATURE:
<221> NAME/KEY: MISC_FEATURE
<223> OTHER INFORMATION: Bba.45
<220> FEATURE:
<221> NAME/KEY: MISC_FEATURE
<222> LOCATION: (1)..(742)
<223> OTHER INFORMATION: VP1 Caspid Protein
<220> FEATURE:
<221> NAME/KEY: MISC_FEATURE
<222> LOCATION: (138)..(742)
<223> OTHER INFORMATION: VP2 Caspid Protein
<220> FEATURE:
<221> NAME/KEY: MISC_FEATURE
<222> LOCATION: (206)..(742)
<223> OTHER INFORMATION: VP3 Caspid Protein

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Arg Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Gln Gln Leu Lys Ser Gly Asp Asn Pro Tyr Leu Lys Tyr Asn His Ala
                85                  90                  95

Asp Ala Glu Phe Gln Gln Arg Leu Ala Thr Asp Thr Ser Phe Gly Gly
            100                 105                 110

Asn Leu Gly Lys Ala Val Phe Gln Ala Lys Lys Arg Ile Leu Glu Pro
        115                 120                 125

Leu Gly Leu Val Glu Glu Gly Val Lys Thr Ala Pro Gly Lys Lys Arg
```

-continued

```
            130                 135                 140
Pro Leu Glu Lys Thr Pro Asn Arg Pro Thr Asn Pro Asp Ser Gly Lys
145                 150                 155                 160

Ala Pro Ala Lys Lys Lys Gln Lys Asp Gly Glu Thr Ala Asp Ser Ala
                165                 170                 175

Arg Arg Ala Leu Asp Phe Glu Asp Ser Gly Ala Gly Asp Gly Pro Pro
            180                 185                 190

Glu Gly Ser Ser Ser Gly Glu Met Ser His Asp Ala Glu Met Arg Ala
                195                 200                 205

Ala Pro Gly Gly Asn Ala Val Glu Ala Gly Gln Gly Ala Asp Gly Val
            210                 215                 220

Gly Asn Ala Ser Gly Asp Trp His Cys Asp Ser Thr Trp Ser Glu Gly
225                 230                 235                 240

Arg Val Thr Thr Thr Ser Thr Arg Thr Trp Val Leu Pro Thr Tyr Asn
                245                 250                 255

Asn His Leu Tyr Leu Arg Ile Gly Thr Thr Ala Asn Ser Asn Thr Tyr
                260                 265                 270

Asn Gly Phe Ser Thr Pro Trp Gly Tyr Phe Asp Phe Asn Arg Phe His
                275                 280                 285

Cys His Phe Ser Pro Arg Asp Trp Gln Arg Leu Ile Asn Asn Asn Trp
            290                 295                 300

Gly Leu Arg Pro Lys Ser Met Arg Val Lys Ile Phe Asn Ile Gln Val
305                 310                 315                 320

Arg Glu Val Thr Thr Ser Asn Gly Glu Thr Thr Val Ala Asn Asn Leu
                325                 330                 335

Thr Ser Thr Val Gln Ile Phe Ala Asp Ser Thr Tyr Glu Leu Pro Tyr
                340                 345                 350

Val Met Asp Ala Gly Gln Glu Gly Ser Leu Pro Pro Phe Pro Asn Asp
            355                 360                 365

Val Phe Met Val Pro Gln Tyr Gly Tyr Cys Gly Val Val Thr Gly Glu
            370                 375                 380

Asn Gln Asn Gln Thr Asp Arg Asn Ala Phe Tyr Cys Leu Glu Tyr Phe
385                 390                 395                 400

Pro Ser Gln Met Leu Arg Thr Gly Asn Asn Phe Glu Ile Ser Tyr Gln
                405                 410                 415

Phe Glu Lys Val Pro Phe His Ser Met Tyr Ala His Ser Gln Ser Leu
                420                 425                 430

Asp Arg Met Met Asn Pro Leu Leu Asp Gln Tyr Leu Trp His Leu Gln
            435                 440                 445

Ser Thr Thr Thr Gly Asn Ser Leu Asn Gln Gly Thr Ala Thr Thr Thr
450                 455                 460

Tyr Gly Lys Ile Thr Thr Gly Asp Phe Ala Tyr Tyr Arg Lys Asn Trp
465                 470                 475                 480

Leu Pro Gly Ala Cys Ile Lys Gln Gln Lys Phe Ser Lys Asn Ala Ser
                485                 490                 495

Gln Asn Tyr Lys Ile Pro Ala Ser Gly Gly Asp Ala Leu Leu Lys Tyr
                500                 505                 510

Asp Thr His Thr Thr Leu Asn Gly Arg Trp Ser Asn Met Ala Pro Gly
            515                 520                 525

Pro Pro Met Ala Thr Ala Gly Ala Gly Asp Ser Asp Phe Ser Asn Ser
            530                 535                 540

Gln Leu Ile Phe Ala Gly Pro Asn Gln Ser Gly Asn Thr Thr Thr Ser
545                 550                 555                 560
```

```
Ser Asn Asn Leu Leu Phe Thr Ser Glu Glu Ile Ala Thr Thr Asn
                565                 570                 575

Pro Arg Asp Thr Asp Met Phe Gly Gln Ile Ala Asp Asn Asn Gln Asn
            580                 585                 590

Ala Thr Thr Ala Pro His Ile Ala Asn Leu Asp Ala Met Gly Ile Val
                595                 600                 605

Pro Gly Met Val Trp Gln Asn Arg Asp Ile Tyr Tyr Gln Gly Pro Ile
            610                 615                 620

Trp Ala Lys Val Pro His Thr Asp Gly His Phe His Pro Ser Pro Leu
625                 630                 635                 640

Met Gly Gly Phe Gly Leu Lys His Pro Pro Gln Ile Phe Ile Lys
                645                 650                 655

Asn Thr Pro Val Pro Ala Asn Pro Asn Thr Thr Phe Ser Ala Ala Arg
                660                 665                 670

Ile Asn Ser Phe Leu Thr Gln Tyr Ser Thr Gly Gln Val Ala Val Gln
                675                 680                 685

Ile Asp Trp Glu Ile Gln Lys Glu His Ser Lys Arg Trp Asn Pro Glu
            690                 695                 700

Val Gln Phe Thr Ser Asn Tyr Gly Thr Gln Asn Ser Met Leu Trp Ala
705                 710                 715                 720

Pro Asp Asn Ala Gly Asn Tyr His Glu Pro Arg Ala Ile Gly Ser Arg
                725                 730                 735

Phe Leu Thr His His Leu
                740

<210> SEQ ID NO 2
<211> LENGTH: 742
<212> TYPE: PRT
<213> ORGANISM: Papio
<220> FEATURE:
<221> NAME/KEY: MISC_FEATURE
<223> OTHER INFORMATION: Bba.46
<220> FEATURE:
<221> NAME/KEY: MISC_FEATURE
<222> LOCATION: (1)..(742)
<223> OTHER INFORMATION: VP1 Caspid Protein
<220> FEATURE:
<221> NAME/KEY: MISC_FEATURE
<222> LOCATION: (138)..(742)
<223> OTHER INFORMATION: VP2 Caspid Protein
<220> FEATURE:
<221> NAME/KEY: MISC_FEATURE
<222> LOCATION: (206)..(742)
<223> OTHER INFORMATION: VP3 Caspid Protein

<400> SEQUENCE: 2

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Gln Gln Leu Lys Ser Gly Asp Asn Pro Tyr Leu Lys Tyr Asn His Ala
                85                  90                  95

Asp Ala Glu Phe Gln Gln Arg Leu Ala Thr Asp Thr Ser Phe Gly Gly
```

```
            100                 105                 110
Asn Leu Gly Lys Ala Val Phe Gln Ala Lys Lys Arg Ile Leu Glu Pro
            115                 120                 125

Leu Gly Leu Val Glu Glu Gly Val Lys Thr Ala Pro Gly Lys Lys Arg
            130                 135                 140

Pro Leu Glu Lys Thr Pro Asn Arg Pro Thr Asn Pro Asp Ser Gly Lys
145                 150                 155                 160

Ala Pro Ala Lys Lys Lys Gln Lys Asp Gly Glu Thr Ala Asp Ser Ala
                165                 170                 175

Arg Arg Thr Leu Asp Phe Glu Asp Ser Gly Ala Gly Asp Gly Pro Pro
            180                 185                 190

Glu Gly Ser Ser Ser Gly Glu Met Ser His Asp Ala Glu Met Arg Ala
            195                 200                 205

Ala Pro Gly Gly Asn Ala Val Glu Ala Gly Gln Gly Ala Asp Gly Val
            210                 215                 220

Gly Asn Ala Ser Gly Asp Trp His Cys Asp Ser Thr Trp Ser Glu Gly
225                 230                 235                 240

Arg Val Thr Thr Thr Ser Thr Arg Thr Trp Val Leu Pro Thr Tyr Asn
                245                 250                 255

Asn His Leu Tyr Leu Arg Ile Gly Thr Thr Ala Asn Ser Asn Thr Tyr
            260                 265                 270

Asn Gly Phe Ser Thr Pro Trp Gly Cys Phe Asp Phe Asn Arg Phe His
            275                 280                 285

Cys His Phe Ser Pro Arg Asp Trp Gln Arg Leu Ile Asn Asn Asn Trp
            290                 295                 300

Gly Leu Arg Pro Lys Ser Met Arg Val Lys Ile Phe Asn Ile Gln Val
305                 310                 315                 320

Lys Glu Val Thr Thr Ser Asn Gly Glu Thr Thr Val Ala Asn Asn Leu
                325                 330                 335

Thr Ser Thr Val Gln Ile Phe Ala Asp Ser Thr Tyr Glu Leu Pro Tyr
            340                 345                 350

Val Met Asp Ala Gly Gln Glu Gly Ser Leu Pro Pro Phe Pro Asn Asp
            355                 360                 365

Val Phe Met Val Pro Gln Tyr Gly Tyr Cys Gly Val Val Thr Gly Glu
            370                 375                 380

Asn Gln Asn Gln Thr Asp Arg Asn Ala Phe Tyr Cys Leu Glu Tyr Phe
385                 390                 395                 400

Pro Ser Gln Met Leu Arg Thr Gly Asn Asn Phe Glu Ile Ser Tyr Gln
            405                 410                 415

Phe Glu Lys Val Pro Phe His Ser Met Tyr Ala His Ser Gln Ser Leu
            420                 425                 430

Asp Arg Met Met Asn Pro Leu Leu Asp Gln Tyr Leu Trp His Leu Gln
            435                 440                 445

Ser Thr Thr Thr Gly Asn Ser Leu Asn Gln Gly Ala Ala Thr Thr Thr
            450                 455                 460

Tyr Gly Lys Ile Thr Thr Gly Asp Phe Ala Tyr Tyr Arg Lys Asn Trp
465                 470                 475                 480

Leu Pro Gly Ala Cys Ile Lys Gln Gln Lys Phe Ser Lys Asn Ala Ser
                485                 490                 495

Gln Asn Tyr Lys Ile Pro Ala Ser Gly Gly Asp Ala Leu Leu Lys Tyr
            500                 505                 510

Asp Thr His Thr Thr Leu Asn Gly Arg Trp Ser Asn Met Ala Pro Gly
            515                 520                 525
```

```
Pro Pro Met Ala Thr Ala Gly Ala Gly Asp Ser Asp Phe Ser Asn Ser
    530                 535                 540

Gln Leu Ile Phe Ala Gly Pro Asn Gln Ser Gly Asn Thr Thr Thr Ser
545                 550                 555                 560

Ser Asn Asn Leu Leu Phe Thr Ser Glu Glu Ile Ala Thr Thr Asn
                565                 570                 575

Pro Arg Asp Thr Asp Met Phe Gly Gln Ile Ala Asp Asn Asn Gln Asn
                580                 585                 590

Ala Thr Thr Ala Pro His Ile Ala Asn Leu Asp Ala Met Gly Ile Val
                595                 600                 605

Pro Gly Met Val Trp Gln Asn Arg Asp Ile Tyr Tyr Gln Gly Pro Ile
    610                 615                 620

Trp Ala Lys Val Pro His Thr Asp Gly His Phe His Pro Ser Pro Leu
625                 630                 635                 640

Met Gly Gly Phe Gly Leu Lys His Pro Pro Gln Ile Phe Ile Lys
                645                 650                 655

Asn Thr Pro Val Pro Ala Asn Pro Asn Thr Thr Phe Ser Ala Ala Arg
                660                 665                 670

Ile Asn Ser Phe Leu Thr Gln Tyr Ser Thr Gly Gln Val Ala Val Gln
                675                 680                 685

Ile Asp Trp Glu Ile Gln Lys Glu His Ser Lys Arg Trp Asn Pro Glu
    690                 695                 700

Val Gln Phe Thr Ser Asn Tyr Gly Thr Gln Asn Ser Met Leu Trp Ala
705                 710                 715                 720

Pro Asp Asn Ala Gly Asn Tyr His Glu Pro Arg Ala Ile Gly Ser Arg
                725                 730                 735

Phe Leu Thr His His Leu
                740

<210> SEQ ID NO 3
<211> LENGTH: 742
<212> TYPE: PRT
<213> ORGANISM: Papio
<220> FEATURE:
<221> NAME/KEY: MISC_FEATURE
<223> OTHER INFORMATION: Bba.47
<220> FEATURE:
<221> NAME/KEY: MISC_FEATURE
<222> LOCATION: (1)..(742)
<223> OTHER INFORMATION: VP1 Caspid Protein
<220> FEATURE:
<221> NAME/KEY: MISC_FEATURE
<222> LOCATION: (138)..(742)
<223> OTHER INFORMATION: VP2 Caspid Protein
<220> FEATURE:
<221> NAME/KEY: MISC_FEATURE
<222> LOCATION: (206)..(742)
<223> OTHER INFORMATION: VP3 Caspid Protein

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Ala Leu Glu His Asp Lys Ala Tyr Asp
```

```
                65                  70                  75                  80
            Gln Gln Leu Lys Ser Gly Asp Asn Pro Tyr Leu Lys Tyr Asn His Ala
                            85                  90                  95
            Asp Ala Glu Phe Gln Gln Arg Leu Ala Thr Asp Thr Ser Phe Gly Gly
                        100                 105                 110
            Asn Leu Gly Lys Ala Val Phe Gln Ala Lys Lys Arg Ile Leu Glu Pro
                        115                 120                 125
            Leu Gly Leu Val Glu Glu Gly Val Lys Thr Ala Pro Gly Lys Lys Arg
                        130                 135                 140
            Pro Leu Glu Lys Thr Pro Asn Arg Pro Thr Asn Pro Asp Ser Gly Lys
            145                 150                 155                 160
            Ala Pro Ala Lys Lys Lys Gln Lys Asp Gly Glu Thr Ala Asp Ser Ala
                            165                 170                 175
            Arg Arg Thr Leu Asp Phe Glu Asp Ser Gly Ala Gly Asp Gly Pro Pro
                        180                 185                 190
            Glu Gly Ser Ser Ser Gly Glu Met Ser His Asp Ala Glu Met Arg Ala
                        195                 200                 205
            Ala Pro Gly Gly Asn Ala Val Glu Ala Gly Gln Gly Ala Asp Gly Val
                        210                 215                 220
            Gly Asn Ala Ser Gly Asp Trp His Cys Asp Ser Thr Trp Ser Glu Gly
            225                 230                 235                 240
            Arg Val Thr Thr Thr Ser Thr Arg Thr Trp Val Leu Pro Thr Tyr Asn
                            245                 250                 255
            Asn His Leu Tyr Leu Arg Ile Gly Thr Thr Ala Asn Ser Asn Thr Tyr
                            260                 265                 270
            Asn Gly Phe Ser Thr Pro Trp Gly Tyr Phe Asp Phe Asn Arg Phe His
                        275                 280                 285
            Cys His Phe Ser Pro Arg Asp Trp Gln Arg Leu Ile Asn Asn Asn Trp
                        290                 295                 300
            Gly Leu Arg Pro Lys Ser Met Arg Val Lys Ile Phe Asn Ile Gln Val
            305                 310                 315                 320
            Lys Glu Val Thr Thr Ser Asn Gly Glu Thr Thr Val Ala Asn Asn Leu
                            325                 330                 335
            Thr Ser Thr Val Gln Ile Phe Ala Asp Ser Thr Tyr Glu Leu Pro Tyr
                        340                 345                 350
            Val Met Asp Ala Gly Gln Glu Gly Ser Leu Pro Pro Phe Pro Asn Asp
                        355                 360                 365
            Val Phe Met Val Pro Gln Tyr Gly Tyr Cys Gly Val Val Thr Gly Glu
                        370                 375                 380
            Asn Gln Asn Gln Thr Asp Arg Asn Ala Phe Tyr Cys Leu Glu Tyr Phe
            385                 390                 395                 400
            Pro Ser Gln Met Leu Arg Thr Gly Asn Asn Phe Glu Ile Ser Tyr Gln
                            405                 410                 415
            Phe Glu Lys Val Pro Phe His Ser Met Tyr Ala His Ser Gln Ser Leu
                        420                 425                 430
            Asp Arg Met Met Asn Pro Leu Leu Asp Gln Tyr Leu Trp His Leu Gln
                        435                 440                 445
            Ser Thr Thr Thr Gly Asn Ser Leu Asn Gln Gly Thr Ala Thr Thr Thr
                        450                 455                 460
            Tyr Gly Lys Ile Thr Thr Gly Asp Phe Ala Tyr Tyr Arg Lys Asn Trp
            465                 470                 475                 480
            Leu Pro Gly Ala Cys Ile Lys Gln Gln Lys Phe Ser Lys Asn Ala Ser
                            485                 490                 495
```

Gln Asn Tyr Lys Ile Pro Ala Ser Gly Gly Asp Ala Leu Leu Lys Tyr
                500                 505                 510

Asp Thr His Thr Thr Leu Asn Gly Arg Trp Ser Asn Met Ala Pro Gly
            515                 520                 525

Pro Pro Met Ala Thr Ala Gly Ala Gly Asp Ser Asp Phe Ser Asn Ser
        530                 535                 540

Gln Leu Ile Phe Ala Gly Pro Asn Gln Ser Gly Asn Thr Thr Thr Ser
545                 550                 555                 560

Ser Asn Asn Leu Leu Phe Thr Ser Glu Glu Ile Ala Thr Thr Asn
                565                 570                 575

Pro Arg Asp Thr Asp Met Phe Gly Gln Ile Ala Asp Asn Gln Asn
                580                 585                 590

Ala Thr Thr Ala Pro His Ile Ala Asn Leu Asp Ala Met Gly Ile Val
            595                 600                 605

Pro Gly Met Val Trp Gln Asn Arg Asp Ile Tyr Tyr Gln Gly Pro Ile
        610                 615                 620

Trp Ala Lys Val Pro His Thr Asp Gly His Phe His Pro Ser Pro Leu
625                 630                 635                 640

Met Gly Gly Phe Gly Leu Lys His Pro Pro Gln Ile Phe Ile Lys
                645                 650                 655

Asn Thr Pro Val Pro Ala Asn Pro Asn Thr Thr Phe Ser Ala Ala Arg
                660                 665                 670

Ile Asn Ser Phe Leu Thr Gln Tyr Ser Thr Gly Gln Val Ala Val Gln
            675                 680                 685

Ile Asp Trp Glu Ile Gln Lys Glu His Ser Lys Arg Trp Asn Pro Glu
        690                 695                 700

Val Gln Phe Thr Ser Asn Tyr Gly Thr Gln Asn Ser Met Leu Trp Ala
705                 710                 715                 720

Pro Asp Asn Ala Gly Asn Tyr His Glu Pro Arg Ala Ile Gly Ser Arg
                725                 730                 735

Phe Leu Thr His His Leu
                740

<210> SEQ ID NO 4
<211> LENGTH: 742
<212> TYPE: PRT
<213> ORGANISM: Papio
<220> FEATURE:
<221> NAME/KEY: MISC_FEATURE
<223> OTHER INFORMATION: Bba.48
<220> FEATURE:
<221> NAME/KEY: MISC_FEATURE
<222> LOCATION: (1)..(742)
<223> OTHER INFORMATION: VP1 Caspid Protein
<220> FEATURE:
<221> NAME/KEY: MISC_FEATURE
<222> LOCATION: (138)..(742)
<223> OTHER INFORMATION: VP2 Caspid Protein
<220> FEATURE:
<221> NAME/KEY: MISC_FEATURE
<222> LOCATION: (206)..(742)
<223> OTHER INFORMATION: VP3 Caspid Protein

<400> SEQUENCE: 4

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro

```
            35                  40                  45
Gly Tyr Lys Tyr Leu Gly Pro Gly Asn Gly Leu Asp Lys Gly Glu Pro
 50                  55                  60

Val Asn Glu Ala Asp Ala Ala Leu Glu His Asp Lys Ala Tyr Asp
 65                  70                  75                  80

Gln Gln Leu Lys Ser Gly Asp Asn Pro Tyr Leu Lys Tyr Asn His Ala
                 85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Ile Leu Glu Pro
             115                 120                 125

Leu Gly Leu Val Glu Glu Gly Val Lys Thr Ala Pro Gly Lys Lys Arg
130                 135                 140

Pro Leu Glu Lys Thr Pro Asn Arg Pro Thr Asn Pro Asp Ser Gly Lys
145                 150                 155                 160

Ala Pro Ala Lys Lys Lys Gln Lys Asp Gly Glu Thr Ala Asp Ser Ala
                165                 170                 175

Arg Arg Thr Leu Asp Phe Glu Asp Ser Gly Ala Gly Asp Gly Pro Pro
            180                 185                 190

Glu Gly Ser Ser Ser Gly Glu Met Ser His Asp Ala Glu Met Arg Ala
            195                 200                 205

Ala Pro Gly Gly Asn Ala Val Glu Ala Gly Gln Gly Ala Asp Gly Val
210                 215                 220

Gly Asn Ala Ser Gly Asp Trp His Cys Asp Ser Thr Trp Ser Glu Gly
225                 230                 235                 240

Arg Val Thr Thr Thr Ser Thr Arg Thr Trp Val Leu Pro Thr Tyr Asn
                245                 250                 255

Asn His Leu Tyr Leu Arg Ile Gly Thr Thr Ala Asn Ser Asn Thr Tyr
            260                 265                 270

Asn Gly Phe Ser Thr Pro Trp Gly Tyr Phe Asp Phe Asn Arg Phe His
            275                 280                 285

Cys Arg Phe Ser Pro Arg Asp Trp Gln Arg Leu Ile Asn Asn Asn Trp
290                 295                 300

Gly Leu Arg Pro Lys Ser Met Arg Val Lys Ile Phe Asn Ile Gln Val
305                 310                 315                 320

Lys Glu Val Thr Thr Ser Asn Gly Glu Thr Thr Val Ala Asn Asn Leu
                325                 330                 335

Thr Ser Thr Val Gln Ile Phe Ala Asp Ser Thr Tyr Glu Leu Pro Tyr
            340                 345                 350

Val Met Asp Ala Gly Gln Glu Gly Ser Leu Pro Pro Phe Pro Asn Asp
            355                 360                 365

Val Phe Met Val Pro Gln Tyr Gly Tyr Cys Gly Val Val Thr Gly Glu
            370                 375                 380

Asn Gln Asn Gln Thr Asp Arg Asn Ala Phe Tyr Cys Leu Glu Tyr Phe
385                 390                 395                 400

Pro Ser Gln Met Leu Arg Thr Gly Asn Asn Phe Glu Ile Ser Tyr Gln
                405                 410                 415

Phe Glu Lys Val Pro Phe His Ser Met Tyr Ala His Ser Gln Ser Leu
            420                 425                 430

Asp Arg Met Met Asn Pro Leu Leu Asp Gln Tyr Leu Trp His Leu Gln
            435                 440                 445

Ser Thr Thr Thr Gly Asn Ser Leu Asn Gln Gly Thr Ala Ile Thr Thr
450                 455                 460
```

```
Tyr Gly Lys Ile Thr Thr Gly Asp Phe Ala Tyr Tyr Arg Lys Asn Trp
465                 470                 475                 480

Leu Pro Gly Ala Cys Ile Lys Gln Gln Lys Phe Ser Lys Asn Ala Ser
                485                 490                 495

Gln Asn Tyr Lys Ile Pro Ala Ser Gly Gly Asp Ala Leu Leu Lys Tyr
            500                 505                 510

Asp Thr His Thr Thr Leu Asn Gly Arg Trp Ser Asn Met Ala Pro Gly
        515                 520                 525

Pro Pro Met Ala Thr Ala Gly Ala Gly Asp Ser Asp Phe Ser Asn Ser
530                 535                 540

Gln Leu Ile Phe Ala Gly Pro Asn Gln Ser Gly Asn Thr Thr Thr Ser
545                 550                 555                 560

Ser Asn Asn Leu Leu Phe Thr Ser Glu Glu Glu Ile Ala Thr Thr Asn
                565                 570                 575

Pro Arg Asp Thr Asp Met Phe Gly Gln Ile Ala Asp Asn Asn Gln Asn
            580                 585                 590

Ala Ala Thr Ala Pro His Ile Ala Asn Leu Asp Ala Met Gly Ile Val
        595                 600                 605

Pro Gly Met Val Trp Gln Asn Arg Asp Ile Tyr Tyr Gln Gly Pro Ile
610                 615                 620

Trp Ala Lys Val Pro His Thr Asp Gly His Phe His Pro Ser Pro Leu
625                 630                 635                 640

Met Gly Gly Phe Gly Leu Lys His Pro Pro Gln Ile Phe Ile Lys
                645                 650                 655

Asn Thr Pro Val Pro Ala Asn Pro Thr Thr Phe Ser Ala Ala Arg
            660                 665                 670

Ile Asn Ser Phe Leu Thr Gln Tyr Ser Thr Gly Gln Val Ala Val Gln
        675                 680                 685

Ile Asp Trp Glu Ile Gln Lys Glu His Ser Lys Arg Trp Asn Pro Glu
690                 695                 700

Val Gln Phe Thr Ser Asn Tyr Gly Thr Gln Asn Ser Met Leu Trp Ala
705                 710                 715                 720

Pro Asp Asn Ala Gly Asn Tyr His Glu Pro Arg Ala Ile Gly Ser Arg
                725                 730                 735

Phe Leu Thr His His Leu
            740

<210> SEQ ID NO 5
<211> LENGTH: 742
<212> TYPE: PRT
<213> ORGANISM: Papio
<220> FEATURE:
<221> NAME/KEY: MISC_FEATURE
<223> OTHER INFORMATION: Bba.49
<220> FEATURE:
<221> NAME/KEY: MISC_FEATURE
<222> LOCATION: (1)..(742)
<223> OTHER INFORMATION: VP1 Caspid Protein
<220> FEATURE:
<221> NAME/KEY: MISC_FEATURE
<222> LOCATION: (138)..(742)
<223> OTHER INFORMATION: VP2 Caspid Protein
<220> FEATURE:
<221> NAME/KEY: MISC_FEATURE
<222> LOCATION: (206)..(742)
<223> OTHER INFORMATION: VP3 Caspid Protein

<400> SEQUENCE: 5

Met Ala Ala Asp Gly Tyr Leu Pro Asp Trp Leu Glu Asp Asn Leu Ser
```

```
1               5                   10                  15
Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
                35                  40                  45

Gly Tyr Lys Tyr Leu Gly Pro Gly Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Gln Gln Leu Lys Ser Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Ile Leu Glu Pro
                115                 120                 125

Leu Gly Leu Val Glu Glu Gly Val Lys Thr Ala Pro Gly Lys Lys Arg
                130                 135                 140

Pro Leu Glu Lys Thr Pro Asn Arg Pro Thr Asn Pro Asp Ser Gly Lys
145                 150                 155                 160

Ala Pro Ala Lys Lys Lys Gln Lys Asp Gly Glu Thr Ala Asp Ser Ala
                165                 170                 175

Arg Arg Thr Leu Asp Phe Glu Asp Ser Gly Ala Gly Asp Gly Pro Pro
                180                 185                 190

Glu Gly Ser Ser Ser Gly Glu Met Ser His Asp Ala Glu Met Arg Ala
                195                 200                 205

Ala Pro Gly Gly Asn Ala Val Glu Ala Gly Gln Gly Ala Asp Gly Val
                210                 215                 220

Gly Asn Ala Ser Gly Asp Trp His Cys Asp Ser Thr Trp Ser Glu Gly
225                 230                 235                 240

Arg Val Thr Thr Thr Ser Thr Arg Thr Trp Val Leu Pro Thr Tyr Asn
                245                 250                 255

Asn His Leu Tyr Leu Arg Ile Gly Thr Thr Ala Asn Ser Asn Thr Tyr
                260                 265                 270

Asn Gly Phe Ser Thr Pro Trp Gly Tyr Phe Asp Phe Asn Arg Phe His
                275                 280                 285

Cys His Phe Ser Pro Arg Asp Trp Gln Arg Leu Ile Asn Asn Asn Trp
                290                 295                 300

Gly Leu Arg Pro Lys Ser Met Arg Val Lys Ile Phe Asn Ile Gln Val
305                 310                 315                 320

Lys Glu Val Thr Thr Ser Asn Gly Glu Thr Thr Val Ala Asn Asn Leu
                325                 330                 335

Thr Ser Thr Val Gln Ile Phe Ala Asp Ser Thr Tyr Glu Leu Pro Tyr
                340                 345                 350

Val Met Asp Ala Gly Gln Glu Gly Ser Leu Pro Pro Phe Pro Asn Asp
                355                 360                 365

Val Phe Met Val Pro Gln Tyr Gly Tyr Cys Gly Val Val Thr Gly Glu
                370                 375                 380

Asn Gln Asn Gln Thr Asp Arg Asn Ala Phe Tyr Cys Leu Glu Tyr Phe
385                 390                 395                 400

Pro Ser Gln Met Leu Arg Thr Gly Asn Asn Phe Glu Ile Ser Tyr Gln
                405                 410                 415

Phe Glu Lys Val Pro Phe His Ser Met Tyr Ala His Ser Gln Ser Leu
                420                 425                 430
```

```
Asp Arg Met Met Asn Pro Leu Leu Asp Gln Tyr Leu Trp His Leu Gln
        435                 440                 445

Ser Thr Thr Thr Gly Asn Ser Leu Asn Gln Gly Thr Ala Ile Thr Thr
    450                 455                 460

Tyr Gly Lys Ile Thr Thr Gly Asp Phe Ala Tyr Tyr Arg Lys Asn Trp
465                 470                 475                 480

Leu Pro Gly Ala Gly Ile Lys Gln Gln Lys Phe Ser Lys Asn Ala Ser
                485                 490                 495

Gln Asn Tyr Lys Ile Pro Ala Ser Gly Gly Asp Ala Leu Leu Lys Tyr
            500                 505                 510

Asp Thr His Thr Thr Leu Asn Gly Arg Trp Ser Asn Met Ala Pro Gly
        515                 520                 525

Pro Pro Met Ala Thr Ala Gly Ala Gly Asp Ser Asp Phe Ser Asn Ser
    530                 535                 540

Gln Leu Ile Phe Ala Gly Pro Asn Gln Ser Gly Asn Thr Thr Thr Ser
545                 550                 555                 560

Ser Asn Asn Leu Leu Phe Thr Ser Glu Glu Glu Ile Ala Thr Thr Asn
                565                 570                 575

Pro Arg Asp Thr Asp Met Phe Gly Gln Ile Ala Asp Asn Asn Gln Asn
            580                 585                 590

Ala Thr Thr Ala Pro His Ile Ala Asn Leu Asp Ala Met Gly Ile Val
        595                 600                 605

Pro Gly Met Val Trp Gln Asn Arg Asp Ile Tyr Tyr Gln Gly Pro Ile
    610                 615                 620

Trp Ala Lys Val Pro His Thr Asp Gly His Phe His Pro Ser Pro Leu
625                 630                 635                 640

Met Gly Gly Phe Gly Leu Lys His Pro Pro Pro Gln Ile Phe Ile Lys
                645                 650                 655

Asn Thr Pro Val Pro Ala Asn Pro Asn Thr Thr Phe Ser Ala Ala Arg
            660                 665                 670

Ile Asn Ser Phe Leu Thr Gln Tyr Ser Thr Gly Gln Val Ala Val Gln
        675                 680                 685

Ile Asp Trp Glu Ile Gln Lys Glu His Ser Lys Arg Trp Asn Pro Glu
    690                 695                 700

Val Gln Phe Thr Ser Asn Tyr Gly Thr Gln Asn Ser Met Leu Trp Ala
705                 710                 715                 720

Pro Asp Asn Ala Gly Asn Tyr His Glu Pro Arg Ala Ile Gly Ser Arg
                725                 730                 735

Phe Leu Thr His His Leu
            740

<210> SEQ ID NO 6
<211> LENGTH: 742
<212> TYPE: PRT
<213> ORGANISM: Papio
<220> FEATURE:
<221> NAME/KEY: MISC_FEATURE
<223> OTHER INFORMATION: Bba.50
<220> FEATURE:
<221> NAME/KEY: MISC_FEATURE
<222> LOCATION: (1)..(742)
<223> OTHER INFORMATION: VP1 Caspid Protein
<220> FEATURE:
<221> NAME/KEY: MISC_FEATURE
<222> LOCATION: (138)..(742)
<223> OTHER INFORMATION: VP2 Caspid Protein
<220> FEATURE:
<221> NAME/KEY: MISC_FEATURE
```

<222> LOCATION: (206)..(742)
<223> OTHER INFORMATION: VP3 Caspid Protein

<400> SEQUENCE: 6

```
Met Ala Ala Asp Gly Tyr Leu Pro Asp Trp Leu Glu Asp Asn Leu Ser
1               5                   10                  15

Glu Ser Ile Arg Glu Trp Trp Ala Leu Lys Pro Gly Ala Pro Arg Pro
            20                  25                  30

Lys Ala Asn Gln Gln His Gln Asp Asp Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Gln Gln Leu Lys Ser Gly Asp Asn Pro Tyr Leu Lys Tyr Asn His Ala
                85                  90                  95

Asp Ala Glu Phe Gln Gln Arg Leu Ala Thr Asp Thr Ser Phe Gly Gly
            100                 105                 110

Asn Leu Gly Lys Ala Val Phe Gln Ala Lys Lys Arg Ile Leu Glu Pro
        115                 120                 125

Leu Gly Leu Val Glu Glu Gly Val Lys Thr Ala Pro Gly Arg Lys Arg
    130                 135                 140

Pro Leu Glu Lys Thr Pro Asn Arg Pro Thr Asn Pro Asp Ser Gly Lys
145                 150                 155                 160

Ala Pro Ala Lys Lys Lys Gln Lys Asp Gly Glu Thr Ala Asp Ser Ala
                165                 170                 175

Arg Arg Thr Leu Asp Phe Glu Asp Ser Gly Ala Gly Asp Gly Pro Pro
            180                 185                 190

Glu Gly Ser Ser Ser Gly Glu Met Ser His Asp Ala Glu Met Arg Ala
        195                 200                 205

Ala Pro Gly Gly Asn Ala Val Glu Ala Gly Gln Gly Ala Asp Gly Val
    210                 215                 220

Gly Asn Ala Ser Gly Asp Trp His Cys Asp Ser Thr Trp Ser Glu Gly
225                 230                 235                 240

Arg Val Thr Thr Thr Ser Thr Arg Thr Trp Val Leu Pro Thr Tyr Asn
                245                 250                 255

Asn His Leu Tyr Leu Arg Ile Gly Thr Thr Ala Asn Ser Asn Thr Tyr
            260                 265                 270

Asn Gly Phe Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Leu Arg Pro Lys Ser Met Arg Val Lys Ile Phe Asn Ile Gln Val
305                 310                 315                 320

Lys Glu Val Thr Thr Ser Asn Gly Glu Thr Thr Val Ala Asn Asn Leu
                325                 330                 335

Thr Ser Thr Val Gln Ile Phe Ala Asp Ser Thr Tyr Glu Leu Pro Tyr
            340                 345                 350

Val Met Asp Ala Gly Gln Glu Gly Ser Leu Pro Pro Phe Pro Asn Asp
        355                 360                 365

Val Phe Met Val Pro Gln Tyr Gly Tyr Cys Gly Val Val Thr Gly Glu
    370                 375                 380

Asn Gln Asn Gln Thr Asp Arg Asn Ala Phe Tyr Cys Leu Glu Tyr Phe
385                 390                 395                 400
```

```
Pro Ser Gln Met Leu Arg Thr Gly Asn Asn Phe Glu Ile Ser Tyr Gln
                405                 410                 415
Phe Glu Lys Val Pro Leu His Ser Met Tyr Ala His Ser Gln Ser Leu
            420                 425                 430
Asp Arg Met Met Asn Pro Leu Leu Asp Gln Tyr Leu Trp His Leu Gln
        435                 440                 445
Ser Thr Thr Thr Gly Asn Ser Leu Asn Gln Gly Thr Ala Thr Thr Thr
    450                 455                 460
Tyr Gly Lys Ile Thr Thr Gly Asp Phe Ala Tyr Tyr Arg Lys Asn Trp
465                 470                 475                 480
Leu Pro Gly Ala Cys Ile Lys Gln Gln Lys Phe Ser Lys Asn Ala Ser
                485                 490                 495
Gln Asn Tyr Lys Ile Pro Ala Ser Gly Glu Asp Ala Leu Leu Lys Tyr
            500                 505                 510
Asp Thr His Thr Thr Leu Asn Gly Arg Trp Ser Asn Met Ala Pro Gly
        515                 520                 525
Pro Pro Met Ala Thr Ala Gly Ala Gly Asp Ser Asp Phe Ser Asn Ser
    530                 535                 540
Gln Leu Ile Phe Ala Gly Pro Asn Gln Ser Gly Asn Thr Thr Thr Ser
545                 550                 555                 560
Ser Asn Asn Leu Leu Phe Thr Ser Glu Glu Ile Ala Thr Thr Asn
                565                 570                 575
Pro Arg Asp Thr Asp Met Phe Gly Gln Ile Ala Asp Asn Asn Gln Asn
            580                 585                 590
Ala Thr Thr Ala Pro His Ile Ala Asn Leu Asp Ala Met Gly Ile Val
        595                 600                 605
Pro Gly Met Val Trp Gln Asn Arg Asp Ile Tyr Tyr Gln Gly Pro Ile
    610                 615                 620
Trp Ala Lys Val Pro His Thr Asp Gly His Phe His Pro Ser Pro Leu
625                 630                 635                 640
Met Gly Gly Phe Gly Leu Lys His Pro Pro Pro Gln Ile Phe Ile Lys
                645                 650                 655
Asn Thr Pro Val Pro Ala Asn Pro Asn Thr Thr Phe Ser Ala Ala Arg
            660                 665                 670
Ile Asn Ser Phe Leu Thr Gln Tyr Ser Thr Gly Gln Val Ala Val Gln
        675                 680                 685
Ile Asp Trp Glu Ile Gln Lys Glu His Ser Lys Arg Trp Asn Pro Glu
    690                 695                 700
Val Gln Phe Thr Ser Asn Tyr Gly Thr Gln Asn Ser Met Leu Trp Ala
705                 710                 715                 720
Pro Asp Asn Ala Gly Asn Tyr His Glu Pro Arg Ala Ile Gly Ser Arg
                725                 730                 735
Phe Leu Thr His His Leu
            740

<210> SEQ ID NO 7
<211> LENGTH: 742
<212> TYPE: PRT
<213> ORGANISM: Papio
<220> FEATURE:
<221> NAME/KEY: MISC_FEATURE
<223> OTHER INFORMATION: Bba.51
<220> FEATURE:
<221> NAME/KEY: MISC_FEATURE
<222> LOCATION: (1)..(742)
<223> OTHER INFORMATION: VP1 Caspid Protein
```

```
<220> FEATURE:
<221> NAME/KEY: MISC_FEATURE
<222> LOCATION: (138)..(742)
<223> OTHER INFORMATION: VP2 Caspid Protein
<220> FEATURE:
<221> NAME/KEY: MISC_FEATURE
<222> LOCATION: (206)..(742)
<223> OTHER INFORMATION: VP3 Caspid Protein

<400> SEQUENCE: 7
```

| | | | | | | | | | | | | | | |
|---|---|---|---|---|---|---|---|---|---|---|---|---|---|---|
| Met | Ala | Ala | Asp | Gly | Tyr | Leu | Pro | Asp | Trp | Leu | Glu | Asp | Asn | Leu | Ser |
| 1 | | | | 5 | | | | | 10 | | | | | 15 | |
| Glu | Gly | Ile | Arg | Glu | Trp | Trp | Ala | Leu | Lys | Pro | Gly | Ala | Pro | Gln | Pro |
| | | | 20 | | | | | 25 | | | | | 30 | | |
| Lys | Ala | Asn | Gln | Gln | His | Gln | Asp | Asn | Ala | Arg | Gly | Leu | Val | Leu | Pro |
| | | | | 35 | | | | | 40 | | | | | 45 | |
| Gly | Tyr | Lys | Tyr | Leu | Gly | Pro | Gly | Asn | Gly | Leu | Asp | Lys | Gly | Glu | Pro |
| | 50 | | | | | 55 | | | | | 60 | | | | |
| Val | Asn | Glu | Ala | Asp | Ala | Ala | Ala | Leu | Glu | His | Asp | Lys | Ala | Tyr | Asp |
| 65 | | | | | 70 | | | | | 75 | | | | | 80 |
| Gln | Gln | Leu | Lys | Ser | Gly | Asp | Asn | Pro | Tyr | Leu | Lys | Tyr | Asn | His | Ala |
| | | | | 85 | | | | | 90 | | | | | 95 | |
| Asp | Ala | Glu | Phe | Gln | Gln | Arg | Leu | Ala | Thr | Asp | Thr | Ser | Phe | Gly | Gly |
| | | | | 100 | | | | | 105 | | | | | 110 | |
| Asn | Leu | Gly | Lys | Ala | Val | Phe | Gln | Ala | Lys | Lys | Arg | Ile | Leu | Glu | Pro |
| | | | 115 | | | | | 120 | | | | | 125 | | |
| Leu | Gly | Leu | Val | Glu | Glu | Gly | Val | Lys | Thr | Ala | Pro | Gly | Lys | Lys | Arg |
| | 130 | | | | | 135 | | | | | 140 | | | | |
| Pro | Leu | Glu | Lys | Thr | Pro | Asn | Arg | Pro | Thr | Asn | Pro | Asp | Ser | Gly | Lys |
| 145 | | | | | 150 | | | | | 155 | | | | | 160 |
| Ala | Pro | Ala | Lys | Lys | Lys | Gln | Lys | Asp | Gly | Glu | Thr | Ala | Asp | Ser | Ala |
| | | | | 165 | | | | | 170 | | | | | 175 | |
| Arg | Arg | Thr | Leu | Asp | Phe | Glu | Asp | Ser | Gly | Ala | Gly | Asp | Gly | Pro | Pro |
| | | | 180 | | | | | 185 | | | | | 190 | | |
| Glu | Gly | Ser | Ser | Ser | Gly | Glu | Met | Ser | His | Asp | Ala | Glu | Met | Arg | Ala |
| | | | | 195 | | | | | 200 | | | | | 205 | |
| Ala | Pro | Gly | Gly | Asn | Ala | Val | Glu | Ala | Gly | Gln | Gly | Ala | Asp | Gly | Val |
| | 210 | | | | | 215 | | | | | 220 | | | | |
| Gly | Asn | Ala | Ser | Gly | Asp | Trp | His | Cys | Asp | Ser | Thr | Trp | Ser | Glu | Gly |
| 225 | | | | | 230 | | | | | 235 | | | | | 240 |
| Arg | Val | Thr | Thr | Thr | Ser | Thr | Arg | Thr | Trp | Val | Leu | Pro | Thr | Tyr | Asn |
| | | | | 245 | | | | | 250 | | | | | 255 | |
| Asn | His | Leu | Tyr | Leu | Arg | Ile | Gly | Thr | Thr | Ala | Asn | Ser | Asn | Thr | Tyr |
| | | | | 260 | | | | | 265 | | | | | 270 | |
| Asn | Gly | Phe | Ser | Thr | Pro | Trp | Gly | Tyr | Phe | Asp | Phe | Asn | Arg | Phe | His |
| | | | 275 | | | | | 280 | | | | | 285 | | |
| Cys | His | Phe | Ser | Pro | Arg | Asp | Trp | Gln | Arg | Leu | Ile | Asn | Asn | Asn | Trp |
| | | | | 290 | | | | | 295 | | | | | 300 | |
| Gly | Leu | Arg | Pro | Lys | Ser | Met | Arg | Val | Lys | Ile | Phe | Asn | Ile | Gln | Val |
| 305 | | | | | 310 | | | | | 315 | | | | | 320 |
| Lys | Glu | Val | Thr | Thr | Ser | Asn | Gly | Glu | Thr | Thr | Val | Ala | Asn | Asn | Leu |
| | | | | 325 | | | | | 330 | | | | | 335 | |
| Thr | Ser | Thr | Val | Gln | Ile | Phe | Ala | Asp | Ser | Thr | Tyr | Glu | Leu | Pro | Tyr |
| | | | | 340 | | | | | 345 | | | | | 350 | |
| Val | Met | Asp | Ala | Gly | Gln | Glu | Gly | Ser | Leu | Pro | Pro | Phe | Pro | Asn | Asp |
| | | | 355 | | | | | 360 | | | | | 365 | | |

Val Phe Met Val Pro Gln Tyr Gly Tyr Cys Gly Val Thr Gly Glu
    370                 375                 380

Asn Gln Asn Gln Thr Asp Arg Asn Ala Phe Tyr Cys Leu Glu Tyr Phe
385                 390                 395                 400

Pro Ser Gln Met Leu Arg Thr Gly Asn Asn Phe Glu Ile Ser Tyr Gln
                405                 410                 415

Phe Glu Lys Val Pro Phe His Ser Met Tyr Ala His Ser Gln Ser Leu
            420                 425                 430

Asp Arg Met Met Asn Pro Leu Leu Asp Gln Tyr Leu Trp His Leu Gln
        435                 440                 445

Ser Thr Thr Thr Gly Asn Ser Leu Asn Gln Gly Thr Ala Thr Thr Thr
    450                 455                 460

Tyr Gly Lys Ile Thr Thr Gly Asp Phe Ala Tyr Tyr Arg Lys Asn Trp
465                 470                 475                 480

Leu Pro Gly Ala Cys Ile Lys Gln Gln Lys Phe Ser Lys Asn Ala Ser
                485                 490                 495

Gln Asn Tyr Lys Ile Pro Ala Ser Gly Gly Asp Ala Leu Leu Lys Tyr
            500                 505                 510

Asp Thr His Thr Thr Leu Asn Gly Arg Trp Ser Asn Met Ala Pro Gly
        515                 520                 525

Pro Pro Met Ala Thr Ala Gly Ala Gly Asp Ser Asp Phe Ser Asn Ser
    530                 535                 540

Gln Leu Ile Phe Ala Gly Pro Asn Gln Ser Gly Asn Thr Thr Thr Ser
545                 550                 555                 560

Ser Asn Asn Leu Leu Phe Thr Ser Glu Glu Ile Ala Thr Thr Asn
                565                 570                 575

Pro Arg Asp Thr Asp Met Phe Gly Gln Ile Ala Asp Asn Gln Asn
            580                 585                 590

Ala Thr Thr Ala Pro His Ile Ala Asn Leu Asp Ala Met Gly Ile Val
        595                 600                 605

Pro Gly Met Val Trp Gln Asn Arg Asp Ile Tyr Tyr Gln Gly Pro Ile
    610                 615                 620

Trp Ala Lys Val Pro His Thr Asp Gly His Phe His Pro Ser Pro Leu
625                 630                 635                 640

Met Gly Gly Phe Gly Leu Lys His Pro Pro Gln Ile Phe Ile Lys
                645                 650                 655

Asn Thr Pro Val Pro Ala Asn Pro Asn Thr Thr Phe Ser Ala Ala Arg
            660                 665                 670

Ile Asn Ser Phe Leu Thr Gln Tyr Ser Thr Gly Gln Val Ala Val Gln
        675                 680                 685

Ile Asp Trp Glu Ile Gln Lys Glu His Ser Lys Arg Trp Asn Pro Glu
    690                 695                 700

Val Gln Phe Thr Ser Asn Tyr Gly Thr Gln Asn Ser Met Leu Trp Ala
705                 710                 715                 720

Pro Asp Asn Ala Gly Asn Tyr His Glu Pro Arg Ala Ile Gly Ser Arg
                725                 730                 735

Phe Leu Thr His His Leu
            740

<210> SEQ ID NO 8
<211> LENGTH: 2229
<212> TYPE: DNA
<213> ORGANISM: Papio
<220> FEATURE:

<221> NAME/KEY: misc_feature
<223> OTHER INFORMATION: Bba.45

<400> SEQUENCE: 8

```
atggctgctg acggttatct tccagattgg ctcgaggaca acctctctga aggcattcgc      60
gagtggtggg cgctgaaacc tggagcccca cagcccaagg caaatcgaca acatcaagac     120
aacgctcggg gtcttgtgct tccgggttac aaatacttgg gacccggtaa cggactcgac     180
aagggagagc cggtcaacga ggcagacgcc gcggccctcg agcacgacaa ggcctacgac     240
cagcagctca agtcgggaga caacccgtac ctcaagtaca accacgcgga cgccgagttc     300
cagcagcgct ggcgaccgga cacctctttt gggggcaacc tcggcaaggc agtcttccag     360
gccaaaaaga ggattctcga gcctctgggt ctggttgaag agggcgttaa acggctcct      420
ggaaagaaac gcccattaga aaagactcca atcggccga ccaacccgga ctctgggaag      480
gccccggcca agaaaaagca aaagacggc gagacagccg actctgctag aagggcactc      540
gactttgaag actctggagc aggagacgga ccccctgagg gatcatcttc cggagaaatg     600
tctcatgatg ctgagatgcg tgcggcgcca ggcggaaatg ctgtcgaggc gggacaaggt     660
gccgatggag tgggtaatgc ctccggtgat tggcattgcg attccacctg gtcagagggc     720
cgagtcacca ccaccagcac ccgaacctgg gtcctgccca cctacaacaa ccacctgtac     780
ctgcgaatcg gaacaacggc caacagcaac acctacaatg gattctccac ccctggggga    840
tactttgact ttaaccgctt ccactgccac ttttccccac gcgactggca gcgactcatc     900
aacaacaact ggggactcag gccgaaatcg atgcgtgtta aaatcttcaa catccaggtc     960
agggaggtca ctacgtcaaa cggcgagact acggtcgcta taaccttac cagcacggtt    1020
cagatctttg cggattcaac gtatgaactc ccatacgtga tggacgccgg tcaggagggg    1080
agccttcctc cgttccccaa cgacgtgttt atggttcccc aatacgggta ctgcggagtc    1140
gtcactggag aaaaccagaa ccaaacagac agaaatgcct tttactgtct ggagtacttt    1200
ccatcccaaa tgctaagaac tggcaacaac tttgaaatca gttaccaatt tgaaaaagtt    1260
cctttccatt caatgtacgc gcacagccag agcctggaca gaatgatgaa tcctttgctg    1320
gatcagtacc tgtggcatct gcaatcgacc actaccggaa attccttaa tcaaggaaca     1380
gctaccacca cgtacgggaa aattaccact ggggactttg cctactacag gaaaaactgg    1440
ttacctggag cctgcattaa acaacaaaaa ttttcaaaga atgccagtca aaactacaag    1500
attcccgcca gcggggaga cgccctttta aagtatgaca cgcataccac tttaaatggg    1560
cgatggagta acatggctcc tggtcctcca atggccaccg caggtgccgg ggactcggat    1620
tttagcaaca gccagctgat ctttgccgga cccaatcaga gcggtaacac gaccacgtct    1680
tcaaacaatt tgttgtttac ctcagaagag gagattgcca caacaaaccc acgagacacg    1740
gacatgtttg acagattgc agataataat caaaatgcca ccaccgcccc tcacatcgct    1800
aacctggacg ctatgggaat tgttcccgga atggtcggc aaaacagaga catctactac    1860
cagggcccta tttgggccaa ggtccctcac acggacggac actttcaccc ttcgccgctg    1920
atgggaggat ttggactgaa acacccgcct ccgcagattt tcatcaaaaa caccccccgta  1980
cccgccaatc ccaatactac ctttagcgct gcaaggatca attctttttt gacgcagtac    2040
agcaccggac aagtcgccgt tcagatcgac tgggaaattc agaaggagca ctccaaacgc    2100
tggaatcccg aagtccaatt tacttcaaac tacggcactc aaaattctat gctgtgggct    2160
cccgacaacg ccggcaacta ccacgaaccc cgggctattg gtcccgtttt cctcacccac    2220
``` cacttgtaa    2229

<210> SEQ ID NO 9
<211> LENGTH: 2229
<212> TYPE: DNA
<213> ORGANISM: Papio
<220> FEATURE:
<221> NAME/KEY: misc_feature
<223> OTHER INFORMATION: Bba.46

<400> SEQUENCE: 9

| | | | | | |
|---|---|---|---|---|---|
| atggctgctg | acggttatct | tccagattgg | ctcgaggaca | acctctctga | aggcattcgc | 60 |
| gagtggtggg | cgctgaaacc | tggagcccca | cagcccaagg | caaatcaaca | acatcaagac | 120 |
| aacgctcggg | gtcttgtgct | tccgggttac | aaatacttgg | gacccggtaa | cggactcgac | 180 |
| aagggagagc | cggtcaacga | ggcagacgcc | gcggccctcg | agcacgacaa | ggcctacgac | 240 |
| cagcagctca | agtcgggaga | caacccgtac | ctcaagtaca | accacgcgga | cgccgagttc | 300 |
| cagcagcgct | tggcgaccga | cacctctttt | gggggcaacc | tcggcaaggc | agtcttccag | 360 |
| gccaaaaaga | ggattctcga | gcctctgggt | ctggttgaag | agggcgttaa | acggctcct | 420 |
| ggaaagaaac | gcccattaga | aaagactcca | aatcggccga | ccaacccgga | ctctgggaag | 480 |
| gccccggcca | agaaaaagca | aaaagacggc | gagacagccg | actctgctag | aaggacactc | 540 |
| gactttgaag | actctggagc | aggagacgga | cccctgagg | gatcatcttc | cggagaaatg | 600 |
| tctcatgacg | ctgagatgcg | tgcggcgcca | ggcggaaatg | ctgtcgaggc | gggacaaggt | 660 |
| gccgatggag | tgggtaatgc | ctccggtgat | tggcattgcg | attccacctg | gtcagagggc | 720 |
| cgagtcacca | ccaccagcac | ccgaacctgg | gtcctgccca | cctacaacaa | ccacctgtac | 780 |
| ctgcgaatcg | gaacaacggc | caacagcaac | acctacaatg | gattctccac | ccctgggga | 840 |
| tgctttgact | ttaaccgctt | ccactgccac | ttttccccac | gcgactggca | gcgactcatc | 900 |
| aacaacaact | ggggactcag | gccgaaatcg | atgcgtgtta | aaatcttcaa | catccaggtc | 960 |
| aaggaggtca | ctacgtcaaa | cggcgagact | acggtcgcta | ataaccttac | cagcacggtt | 1020 |
| cagatctttg | cggattcaac | gtatgaactc | ccatacgtga | tggacgccgg | tcaggagggg | 1080 |
| agccttcctc | cgttccccaa | cgacgtgttt | atggttcccc | aatacgggta | ctgcggagtc | 1140 |
| gtcactggag | aaaaccagaa | ccaaacagag | agaaatgcct | tttactgtct | ggagtacttt | 1200 |
| ccatcccaaa | tgctaagaac | tggcaacaac | tttgaaatca | gttaccaatt | tgaaaaagtt | 1260 |
| cctttccatt | caatgtacgc | gcacagccag | agcctggaca | gaatgatgaa | tcctttgctg | 1320 |
| gatcagtacc | tgtggcatct | gcaatcgacc | actaccggaa | attcccttaa | tcaaggagca | 1380 |
| gctaccacca | cgtacgggaa | aattaccact | ggggactttg | cctactacag | gaaaaactgg | 1440 |
| ttgcctggag | cctgcattaa | acaacaaaaa | ttttcaaaga | atgccagtca | aaactacaag | 1500 |
| atccccgcca | gcggggggaga | cgcccttttta | aagtatgaca | cgcataccac | tttaaatggg | 1560 |
| cgatggagta | acatggctcc | tggtcctcca | atggccaccg | caggtgccgg | ggactcggat | 1620 |
| tttagcaaca | gccagctgat | cttttgccgga | cccaatcaga | gcggtaacac | gaccacgtct | 1680 |
| tcaaacaatt | tgttgtttac | ctcagaagag | gagattgcca | caacaaaccc | acgagacacg | 1740 |
| gacatgtttg | acagattgc | agataataat | caaaatgcca | ccaccgcccc | tcacatcgct | 1800 |
| aacctggacg | ctatgggaat | tgttcccgga | atggtctggc | aaaacagaga | catctactac | 1860 |
| cagggcccta | tttgggccaa | ggtccctcac | acggacggaa | actttcaccc | ttcgccgctg | 1920 |
| atgggaggat | ttggactgaa | acacccgcct | ccgcagattt | tcatcaaaaa | cacccccgta | 1980 |

| | | | | |
|---|---|---|---|---|
| cccgccaatc | ccaatactac | ctttagcgct | gcaaggatca | attctttttt | gacgcagtac | 2040 |
| agcaccggac | aagtcgccgt | tcagatcgac | tgggaaattc | agaaggagca | ctccaaacgc | 2100 |
| tggaatcccg | aagtccaatt | tacttcaaac | tacggcactc | aaaattctat | gctgtgggct | 2160 |
| cccgacaacg | ccggcaacta | ccacgaaccc | cgggctattg | ggtcccgttt | cctcacccac | 2220 |
| cacttgtaa | | | | | 2229 |

```
<210> SEQ ID NO 10
<211> LENGTH: 2229
<212> TYPE: DNA
<213> ORGANISM: Papio
<220> FEATURE:
<221> NAME/KEY: misc_feature
<223> OTHER INFORMATION: Bba.47
```

<400> SEQUENCE: 10

| | | | | | | |
|---|---|---|---|---|---|---|
| atggctgctg | acggttatct | tccagattgg | ctcgaggaca | acctctctga | aggcattcgc | 60 |
| gagtggtggg | cgctgaaacc | tggagcccca | cagcccaagg | caaatcaaca | acatcaagac | 120 |
| aacgctcggg | gtcttgtgct | tccgggttac | aaatacttgg | acccggtaa | cggactcgac | 180 |
| aagggagagc | cggtcaacga | ggcagacgcc | gcggccctcg | agcacgacaa | ggcctacgac | 240 |
| cagcagctca | agtcgggaga | caacccgtac | ctcaagtaca | ccacgcgga | cgccgagttc | 300 |
| cagcagcgct | tggcgaccga | cacctctttt | gggggcaacc | tcggcaaggc | agtcttccag | 360 |
| gccaaaaaga | ggattctcga | gcctctgggt | ctggttgaag | agggcgttaa | acggctcct | 420 |
| ggaaagaaac | gcccattaga | aaagactcca | aatcggccga | ccaacccgga | ctctgggaag | 480 |
| gccccggcca | agaaaaagca | aaaagacggc | gagacagccg | actctgctag | aaggacactc | 540 |
| gactttgaag | actctggagc | aggagacgga | cctcctgagg | gatcatcttc | cggagaaatg | 600 |
| tctcatgatg | ctgagatgcg | tgcggcgcca | ggcggaaatg | ctgtcgaggc | gggacaaggt | 660 |
| gccgatggag | tgggtaatgc | ctccggtgat | tggcattgcg | attccacctg | gtcagagggc | 720 |
| cgagtcacca | ccaccagcac | ccgaacctgg | gtcctgccca | cctacaacaa | ccacctgtac | 780 |
| ctgcgaatcg | gaacaacggc | caacagcaac | acctacaatg | gattctccac | cccctgggga | 840 |
| tactttgact | ttaaccgctt | ccactgccac | ttttccccac | gcgactggca | gcgactcatc | 900 |
| aacaacaact | ggggactcag | gccgaaatcg | atgcgtgtta | aaatcttcaa | catccaggtc | 960 |
| aaggaggtca | ctacgtcaaa | cggcgagact | acggtcgcta | taaccttac | cagcacggtt | 1020 |
| cagatctttg | cggattcaac | gtatgaactc | ccatacgtga | tggacgccgg | tcaggagggg | 1080 |
| agccttcctc | cgttccccaa | cgacgtgttt | atggttcccc | aatacgggta | ctgcggagtc | 1140 |
| gtcactggag | aaaaccagaa | ccaaacagac | agaaatgcct | tttactgtct | ggagtacttt | 1200 |
| ccatcccaaa | tgctaagaac | tggcaacaac | tttgaaatca | gttaccaatt | tgaaaaagtt | 1260 |
| cctttccatt | caatgtacgc | gcacagccag | agcctggaca | gaatgatgaa | tcctttgctg | 1320 |
| gatcagtacc | tgtggcatct | gcaatcgacc | actaccggaa | attcccttaa | tcaaggaaca | 1380 |
| gctaccacca | cgtacgggaa | aattaccact | ggggactttg | cctactacag | gaaaaactgg | 1440 |
| ttgcctggag | cctgcattaa | caacaaaaa | ttttcaaaga | atgccagtca | aaactacaag | 1500 |
| attcccgcca | gcgggggaga | cgcccttta | aagtatgaca | cgcataccac | tttaaatggg | 1560 |
| cgatggagta | acatggctcc | tggtcctcca | atggccaccg | caggtgccgg | ggactcggat | 1620 |
| tttagcaaca | gccagctgat | cttttgccgga | cccaatcaga | gcggtaacac | gaccacgtct | 1680 |
| tcaaacaatt | tgttgtttac | ctcagaagag | gagattgcca | caacaaaccc | acgagacacg | 1740 |

```
gacatgtttg ggcagattgc agataataat caaaatgcca ccaccgcccc tcacatcgct    1800
aacctggacg ctatgggaat tgttcccgga atggtctggc aaaacagaga catctactac    1860
cagggcccta tttgggccaa ggtccctcac acggacggac actttcaccc ttcgccgctg    1920
atgggaggat ttggactgaa acacccgcct ccgcagattt tcatcaaaaa caccccccgta   1980 cccgccaatc ccaatactac ctttagcgct gcaaggatca attctttttt gacgcagtac    2040
agcaccggac aagtcgccgt tcagatcgac tgggaaattc agaaggagca ctccaaacgc    2100
tggaatcccg aagtccaatt tacttcaaac tacggcactc aaaattctat gctgtgggct    2160
cccgacaacg ccggcaacta ccacgaaccc cgggctattg ggtcccgttt cctcacccac    2220
cacttgtaa                                                             2229

<210> SEQ ID NO 11
<211> LENGTH: 2229
<212> TYPE: DNA
<213> ORGANISM: Papio
<220> FEATURE:
<221> NAME/KEY: misc_feature
<223> OTHER INFORMATION: Bba.48

<400> SEQUENCE: 11
atggctgctg acggttatct tccagattgg ctcgaggaca acctctctga aggcattcgc     60
gagtggtggg cgctgaaacc tggagcccca cagcccaagg caaatcaaca acatcaagac    120
aacgctcggg gtcttgtgct tccgggttac aaatacttgg acccggtaa cggactcgac     180 aagggagagc cggtcaacga ggcagacgcc gcggccctcg agcacgacaa ggcctacgac    240
cagcagctca gtcgggaga caacccgtac ctcaagtaca accacgcgga cgccgagttt    300
caggagcgtc ttcaagaaga tacgtctttt gggggcaacc tcgggcgagc agtcttccag    360
gccaaaaaga ggattctcga gcctctgggt ctggttgaag agggcgttaa aacggctcct    420
ggaaagaaac gcccattaga aaagactcca aatcggccga ccaacccgga ctctgggaag    480
gccccggcca agaaaaagca aaaagacggc gagacagccg actctgctag aaggacactc    540
gactttgaag actctggagc aggagacgga ccccctgagg gatcatcttc cggagaaatg    600
tctcatgatg ctgagatgcg tgcggcgcca ggcgaaatg ctgtcgaggc gggacaaggt    660
gccgatggag tgggtaatgc ctccggtgat tggcattgcg attccacctg gtcagagggc    720
cgagtcacca ccaccagcac ccgaacctgg gtcctgccca cctacaacaa ccacctgtac    780
ctgcgaatcg gacaacggc caacagcaac acctacaatg gattctccac cccctgggga    840
tactttgact ttaaccgctt ccactgccgc ttttccccgc gcgactggca gcgactcatc    900
aacaacaact ggggactcag gccgaaatcg atgcgtgtta aaatcttcaa catccaggtc    960
aaggaggtca ctacgtcaaa cggcgagact acggtcgcta taaccttac cagcacggtt   1020 cagatctttg cggattcaac gtatgaactc ccatacgtga tggacgccgg tcaggagggg   1080
agccttcctc cgttccccaa cgacgtgttt atggttcccc aatacgggta ctgcggagtc   1140
gtcactggag aaaaccagaa ccaaacagac agaaatgcct ttactgtct ggagtacttt   1200 ccatcccaaa tgctaagaac tggcaacaac tttgaaatca gttaccaatt tgaaaaagtt   1260
cctttccatt caatgtacgc gcacagccag agcctggaca gaatgatgaa tcctttgctg   1320
gatcagtacc tgtggcatct gcaatcgacc actaccggaa attcccttaa tcaaggaaca   1380
gctatcacca cgtacgggaa aattaccact ggggactttg cctactacag gaaaaactgg   1440
ttgcctggag cctgcattaa acaacaaaaa ttttcaaaga atgccagtca aaactacaag   1500
```

| | | |
|---|---|---|
| attcccgcca gcgggggaga cgcccttttta aagtatgaca cgcataccac tttaaatggg | 1560 | |
| cgatggagta acatggctcc tggtcctcca atggccaccg caggtgccgg ggactcggat | 1620 | |
| tttagcaaca gccagctgat cttttgccgga cccaatcaga gcggtaacac gaccacgtct | 1680 | |
| tcaaacaatt tgttgtttac ctcagaagag gagattgcca caacaaaccc acgagacacg | 1740 | |
| gacatgtttg gacagattgc agataataat caaaatgccg ccaccgcccc tcacatcgct | 1800 | |
| aacctggacg ctatgggaat tgttcccgga atggtctggc aaaacagaga catctactac | 1860 | |
| cagggcccta tttgggccaa ggtccctcac acggacggac actttcaccc ttcgccgctg | 1920 | |
| atgggaggat ttggactgaa acaccccgcct ccgcagattt tcatcaaaaa cacccccgta | 1980 | |
| cccgccaatc ccaatactac ctttagcgct gcaaggatca attcttttt gacgcagtac | 2040 | |
| agcaccggac aagtcgccgt tcagatcgac tgggaaattc agaaggagca ctccaaacgc | 2100 | |
| tggaatcccg aagtccaatt tacttcaaac tacggcactc aaaattctat gctgtgggct | 2160 | |
| cccgacaacg ccggcaacta ccacgaaccc cgggctattg ggtcccgttt cctcacccac | 2220 | |
| cacttgtaa | 2229 | |

<210> SEQ ID NO 12
<211> LENGTH: 2229
<212> TYPE: DNA
<213> ORGANISM: Papio
<220> FEATURE:
<221> NAME/KEY: misc_feature
<223> OTHER INFORMATION: Bba. 49

<400> SEQUENCE: 12

| | | |
|---|---|---|
| atggctgctg acggttatct tccagattgg ctcgaggaca acctctctga aggcattcgc | 60 | |
| gagtggtggg cgctgaaacc tggagcccca cagcccaagg caaatcaaca acatcaagac | 120 | |
| aacgctcggg gtcttgtgct tccgggttac aaatacttgg acccggtaa cggactcgac | 180 | |
| aagggagagc cggtcaacga ggcagacgcc gcggccctcg agcacgacaa ggcctacgac | 240 | |
| cagcagctca agtcgggaga caacccgtac ctcaagtaca accacgcgga cgccgagttt | 300 | |
| caggagcgtc ttcaagaaga tacgtctttt ggggcaacc tcgggcgagc agtcttccag | 360 | |
| gccaaaaaga ggattctcga gcctctgggt ctggttgaag agggcgttaa aacggctcct | 420 | |
| ggaaagaaac gcccattaga aaagactcca atcggccga ccaacccgga ctctgggaag | 480 | |
| gccccggcca agaaaaagca aaaagacggc gagacagccg actctgctag aaggacactc | 540 | |
| gactttgaag actctggagc aggagacgga ccccctgagg gatcatcttc cggagaaatg | 600 | |
| tctcatgatg ctgagatgcg tgcggcgcca ggcgaaatg ctgtcgaggc gggacaaggt | 660 | |
| gccgatggag tgggtaatgc ctccggtgat tggcattgcg attccacctg gtcagagggc | 720 | |
| cgagtcacca ccaccagcac ccgaacctgg gtcctgccca cctacaacaa ccacctgtac | 780 | |
| ctgcgaatcg gaacaacggc caacagcaac acctacaatg gattctccac cccctgggga | 840 | |
| tactttgact ttaaccgctt ccactgccac ttttccccac gcgactggca gcgactcatc | 900 | |
| aacaacaact ggggactcag gccgaaatcg atgcgtgtta aaatcttcaa catccaggtc | 960 | |
| aaggaggtca ctacgtcaaa cggcgagact acggtcgcta ataaccttac cagcacggtt | 1020 | |
| cagatctttg cggattcaac gtatgaactc ccatacgtga tggacgccgg tcaggagggg | 1080 | |
| agccttcctc cgttccccaa cgacgtgttt atggttcccc aatacgggta ctgcggagtc | 1140 | |
| gtcactggag aaaaccagaa ccaaacagac agaaatgcct tttactgtct ggagtacttt | 1200 | |
| ccatcccaaa tgctaagaac tggcaacaac tttgaaatca gttaccaatt tgaaaaagtt | 1260 | |

| | |
|---|---|
| cctttccatt caatgtacgc gcacagccag agcctggaca gaatgatgaa tcctttgctg | 1320 |
| gatcagtacc tgtggcatct gcaatcgacc actaccggaa attcccttaa tcaaggaaca | 1380 |
| gctatcacca cgtacgggaa aattaccact ggggactttg cctactacag gaaaaactgg | 1440 |
| ttgcctggag ccggcattaa acaacaaaaa ttttcaaaga atgccagtca aaactacaag | 1500 |
| attcccgcca gcgggggaga cgccctttta agtatgaca cgcataccac tttaaatggg | 1560 |
| cgatggagta acatggctcc tggtcctcca atggccaccg caggtgccgg ggactcggat | 1620 |
| tttagcaaca gccagctgat cttttgccgga cccaatcaga gcggtaacac gaccacgtct | 1680 |
| tcaaacaatt tgttgtttac ctcagaagag gagattgcca caacaaaccc acgagacacg | 1740 |
| gacatgtttg gacagattgc agataataat caaaatgcca ccaccgcccc tcacatcgct | 1800 |
| aacctggacg ctatgggaat tgttcccgga atggtctggc aaaacagaga catctactac | 1860 |
| cagggcccta tttgggccaa ggtccctcac acggacggac actttcaccc ttcgccgctg | 1920 |
| atgggaggat ttggactgaa acacccgcct ccgcagattt tcatcaaaaa cacccccgta | 1980 |
| cccgccaatc ccaatactac ctttagcgct gcaaggatca attcttttt gacgcagtac | 2040 |
| agcaccggac aagtcgccgt tcagatcgac tgggaaattc agaaggagca ctccaaacgc | 2100 |
| tggaatcccg aagtccaatt tacttcaaac tacggcactc aaaattctat gctgtgggct | 2160 |
| cccgacaacg ccggcaacta ccacgaaccc cgggctattg ggtcccgttt cctcacccac | 2220 |
| cacttgtaa | 2229 |

<210> SEQ ID NO 13
<211> LENGTH: 2229
<212> TYPE: DNA
<213> ORGANISM: Papio
<220> FEATURE:
<221> NAME/KEY: misc_feature
<223> OTHER INFORMATION: Bba.50

<400> SEQUENCE: 13

| | |
|---|---|
| atggctgctg acggttatct tccagattgg ctcgaggaca acctctctga aagcattcgc | 60 |
| gagtggtggg cgctgaaacc tggagcccca cggcccaagg caaatcaaca acatcaagac | 120 |
| gacgctcggg gtcttgtgct tccgggttac aaatacttgg acccggtaa cggactcgac | 180 |
| aagggagagc cggtcaacga ggcagacgcc gcggccctcg agcacgacaa ggcctacgac | 240 |
| cagcagctca agtcgggaga caacccgtac ctcaagtaca accacgcgga cgccgagttc | 300 |
| cagcagcgct ggcgaccgca cacctctttt ggggcaacc tcggcaaggc agtcttccag | 360 |
| gccaaaaaga ggattctcga gcctctgggt ctggttgaag agggcgttaa aacggctcct | 420 |
| ggaaggaaac gcccattaga aaagactcca atcggccga ccaacccgga ctctgggaag | 480 |
| gccccggcca agaaaaagca aaagacggc gagacagccg actctgctag aaggacactc | 540 |
| gactttgaag actctggagc aggagacgga ccccctgagg gatcatcttc cggagaaatg | 600 |
| tctcatgatg ctgagatgcg tgcggcgcca ggcggaaatg ctgtcgaggc gggacaaggt | 660 |
| gccgatggag tgggtaatgc ctccggtgat tggcattgcg attccacctg gtcagagggc | 720 |
| cgagtcacca ccaccagcac ccgaacctgg gtcctgccca cctacaacaa ccacctgtac | 780 |
| ctgcgaatcg gaacaacggc caacagcaac acctacaatg gattctccac ccctgggga | 840 |
| tactttgact ttaaccgctt ccactgccac tttttcccac gcgactggca gcgactcatc | 900 |
| aacaacaact ggggactcag gccgaaatcg atgcgtgtta aaatcttcaa catccaggtc | 960 |
| aaggaggtca ctacgtcaaa cggcgagact acggtcgcta ataaccttac cagcacggtt | 1020 |

```
cagatctttg cggattcaac gtatgaactc ccatacgtga tggacgccgg tcaggagggg    1080
agccttcctc cgttccccaa cgacgtgttt atggttcccc aatacgggta ctgcggagtc    1140
gtcactggag aaaaccagaa ccaaacagac agaaatgcct tttactgtct ggagtacttt    1200
ccatcccaaa tgctaagaac tggcaacaac tttgaaatca gttaccaatt tgaaaaagtt    1260
cctctccatt caatgtacgc gcacagccag agcctggaca gaatgatgaa tcctttgctg    1320
gatcagtacc tgtggcatct gcaatcgacc actaccggaa attcccttaa tcaaggaaca    1380
gctaccacca cgtacgggaa aattaccact ggggactttg cctactacag gaaaaactgg    1440
ttgcctggag cctgcattaa acaacaaaaa ttttcaaaga atgccagtca aaactacaag    1500
attcccgcca gcggggaaga cgcccttttta aagtatgaca cgcataccac tttaaatggg    1560
cgatggagta acatggctcc tggtcctcca atggccaccg caggtgccgg ggactcggat    1620
tttagcaaca gccagctgat cttttgccgga cccaatcaga gcggtaacac gaccacgtct    1680
tcaaacaatt tgttgtttac ctcagaagag gagattgcca caacaaaccc acgagacacg    1740
gacatgtttg gacagattgc agataataat caaaatgcca ccaccgcccc tcacatcgct    1800
aacctggacg ctatgggaat tgttcccgga atggtctggc aaaacagaga catctactac    1860
cagggcccta tctgggccaa ggtccctcac acggacggac acttcacccc ttcgccgctg    1920
atgggaggat ttggactgaa acacccgcct ccgcagattt tcatcaaaaa cacccccgta    1980
cccgccaatc ccaatactac ctttagcgct gcaaggatca attcttttttt gacgcagtac    2040 agcaccggac aagtcgccgt tcagatcgac tgggaaattc agaaggagca ctccaaacgc    2100
tggaatcccg aagtccaatt tacttcaaac tacggcactc aaaattctat gctgtgggct    2160
cccgacaacg ccggcaacta ccacgaaccc cgggctattg ggtcccgttt cctcacccac    2220
cacttgtaa                                                             2229
```

<210> SEQ ID NO 14
<211> LENGTH: 2229
<212> TYPE: DNA
<213> ORGANISM: Papio
<220> FEATURE:
<221> NAME/KEY: misc_feature
<223> OTHER INFORMATION: Bba.51

<400> SEQUENCE: 14

```
atggctgctg acggttatct tccagattgg ctcgaggaca acctctctga aggcattcgc     60
gagtggtggg cgctgaaacc tggagcccca cagcccaagg caaatcaaca acatcaagac    120
aacgctcggg tcttgtgct tccgggttac aaatacttgg acccggtaa cggactcgac      180 aagggagagc cggtcaacga ggcagacgcc gcggccctcg agcacgacaa ggcctacgac    240
cagcagctca gtcgggaga caacccgtac ctcaagtaca accacgcgga cgccgagttc    300
cagcagcgct tggcgaccga cacctctttt gggggcaacc tcggcaaggc agtcttccag    360
gccaaaaaga ggattctcga gcctctgggt ctggttgaag agggcgttaa aacggctcct    420
ggaaagaaac gcccattaga aaagactcca atcggccga ccaacccgga ctctgggaag    480
gccccggcca gaaaaagca aaagacggc gagacagccg actctgctag aaggacactc     540
gactttgaag actctggagc aggagacgga ccccctgagg atcatcttc cggagaaatg    600 tctcatgatg ctgagatgcg tgcggcgcca ggcggaaatg ctgtcgaggc gggacaaggt    660
gccgatggag tgggtaatgc ctccggtgat tggcattgcg attccacctg gtcagagggc    720
cgagtcacca ccaccagcac ccgaacctgg gtcctgccca cctacaacaa ccacctgtac    780
```

-continued

```
ctgcgaatcg gaacaacggc caacagcaac acctacaatg gattctccac cccctgggga    840
tactttgact ttaaccgctt ccactgccac ttttccccac gcgactggca gcgactcatc    900
aacaacaact ggggactcag gccgaaatcg atgcgtgtta aaatcttcaa catccaggtc    960
aaggaggtca ctacgtcaaa cggcgagact acggtcgcta ataaccttac cagcacggtt   1020
cagatctttg cggattcaac gtatgaactc ccatacgtga tggacgccgg tcaggagggg   1080
agccttcctc cgttcccaa cgacgtgttt atggttcccc aatacgggta ctgcggagtc    1140
gtcactggag aaaaccagaa ccaaacagac agaaatgcct tttactgtct ggagtacttt   1200
ccatcccaaa tgctaagaac tggcaacaac tttgaaatca gttaccaatt tgaaaaagtt   1260
cctttccatt caatgtacgc gcacagccag agcctggaca gaatgatgaa tcctttgctg   1320
gatcagtacc tgtggcatct gcaatcgacc actaccggaa attcccttaa tcaaggaaca   1380
gctaccacca cgtacgggaa aattaccact ggggactttg cctactacag gaaaaactgg   1440
ttgcctggag cctgcattaa acaacaaaaa ttttcaaaga atgccagtca aaactacaag   1500
attcccgcca gcggggaga cgccttttta aagtatgaca cgcataccac tttaaatggg    1560
cgatggagta acatggctcc tggtcctcca atggccaccg caggtgccgg ggactcggat   1620
tttagcaaca gccagctgat ctttgccgga cccaatcaga gcggtaacac gaccacgtct   1680
tcaaacaatt tgttgtttac ctcagaagag gagattgcca caacaaaccc acgagacacg   1740
gacatgtttg gacagattgc agataataat caaaatgcca ccaccgcccc tcacatcgct   1800
aacctggacg ctatgggaat tgttcccgga atggtctggc aaaacagaga catctactac   1860
cagggcccta tttgggccaa ggtccctcac acggacggac actttcaccc ttcgccgctg   1920
atgggaggat ttggactgaa acacccgcct ccgcagattt tcatcaaaaa cacccccgta   1980
cccgccaatc ccaatactac ctttagcgct gcaaggatca attctttttt gacgcagtac   2040
agcaccggac aagtcgccgt tcagatcgac tgggaaattc agaaggagca ctccaaacgc   2100
tggaatcccg aagtccaatt tacttcaaac tacggcactc aaaattctat gctgtgggct   2160
cccgacaacg ccggcaacta ccacgaaccc cgggctattg ggtcccgttt cctcacccac   2220
cacttgtaa                                                           2229
```

LIVER TARGETING ADENO-ASSOCIATED VIRAL VECTORS

This application claims priority to U.S. Provisional Application No. 62/671,265, filed May 14, 2018, which is incorporated by reference herein in its entirety.

INCORPORATION BY REFERENCE OF MATERIAL SUBMITTED ELECTRONICALLY

This application contains, as a separate part of the disclosure, a Sequence Listing in computer-readable form which is incorporated by reference in its entirety and identified as follows: Filename: 53120_Seqlisting.txt; Size: 68,361 bytes; Created: May 10, 2019.

FIELD OF INVENTION

The invention relates to novel adeno-associated virus (AAV) capsid proteins, AAV particles comprising a novel capsid protein, polynucleotides encoding these capsid proteins and AAV vectors expressing these capsid proteins. The invention also relates to methods of making the herein described AAV vectors containing the novel capsid proteins of the invention and associated therapeutic uses thereof.

BACKGROUND

AAV is a replication-deficient parvovirus, the single-stranded DNA genome of which is about 4.7 kb in length including two separate 145 nucleotide inverted terminal repeat (ITRs). The nucleotide sequence of the AAV serotype 2 (AAV2) genome is presented in Srivastava et al., *J. Virol.*, 45: 555-564 (1983) as corrected by Ruffing et al., *J. Gen. Virol.*, 75: 3385-3392 (1994). Cis-acting sequences directing viral DNA replication (rep), encapsidation/packaging and host cell chromosome integration are contained within the ITRs. Three AAV promoters, p5, p19, and p40 (named for their relative map locations), drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties which are ultimately responsible for replicating the viral genome. The cap gene is expressed from the p40 promoter and it encodes the three capsid proteins VP1, VP2, and VP3. Alternative splicing and a non-consensus translational start site are responsible for the production of the three related capsid proteins. A single consensus polyadenylation site is located at map position 95 of the AAV genome. The life cycle and genetics of AAV are reviewed in Muzyczka, *Current Topics in Microbiology and Immunology*, 158: 97-129 (1992).

When AAV infects a human cell, the viral genome can integrate into chromosome 19 resulting in latent infection of the cell. Production of infectious virus does not occur unless the cell is infected with a helper virus (for example, adenovirus or herpesvirus). In the case of adenovirus, genes E1A, E1B, E2A, E4 and VA provide helper functions. Upon infection with a helper virus, the AAV provirus is rescued and amplified, and both AAV and adenovirus are produced.

AAV possesses unique features that make it attractive as a vaccine vector for expressing immunogenic peptides/polypeptides and as a vector for delivering foreign DNA to cells, for example, in gene therapy. AAV infection of cells in culture is non-cytopathic, and natural infection of humans and other animals is silent and asymptomatic. Moreover, AAV infects many mammalian cells allowing the possibility of targeting many different tissues in vivo. The AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA such as a gene cassette containing a promoter, a DNA of interest and a polyadenylation signal. The rep and cap proteins may be provided in trans. Another significant feature of AAV is that it is an extremely stable and hearty virus. It easily withstands the conditions used to inactivate adenovirus (56° to 65° C. for several hours), making cold preservation of rAAV-vectors less critical. AAV may even be lyophilized. Finally, AAV-infected cells are not resistant to superinfection.

AAV vectors find use in numerous mammalian gene therapy applications and there is a need for new and/or modified AAV vectors and associated virus that find use in gene therapy applications. The present invention provides for novel AAV vectors expressing the novel AAV capsid proteins of the present invention, and novel, non-naturally occurring AAV virions comprising those vectors or capsid proteins.

SUMMARY OF INVENTION

The invention provides for novel AAV capsid proteins, which may be novel VP1, VP2 or VP3 capsid proteins, non-naturally occurring AAV virus comprising any of these capsid proteins, and use of such AAV virus for gene therapy applications and for use in the preparation of medicaments for gene therapy applications. In some embodiments, the AAV capsid proteins were isolated and identified from various mammalian tissues. The amino acid sequences of certain novel mammalian-derived AAV capsid VP1 proteins are set out as SEQ ID NOS:1-7, and the associated locations of the respective VP2 and VP3 sequences are also herein described. Collectively, the novel capsid proteins are referred to herein as "AAV capsid proteins of the invention."

In one embodiment, the invention provides an adeno-associated virus (AAV) having a capsid protein having an amino acid sequence that is at least 95% identical to (i) any one of SEQ ID NOS:1-7, (ii) the VP2 region of any one of SEQ ID NOS:1-7, or (iii) the VP3 region of any one of SEQ ID NOS:1-7, and further having a transgene where the transgene is composed of a heterologous gene operably linked to regulatory sequences that control expression of the heterologous gene in a host cell. In another embodiment the capsid protein has the amino acid sequence of (i) any one of SEQ ID NOS:1-7, (ii) the VP2 region of any one of SEQ ID NOS:1-7, or (iii) the VP3 region of any one of SEQ ID NOS:1-7. In yet another embodiment, the AAV has an AAV inverted terminal repeat sequence. In further embodiments, the AAV are mixed with a physiologically compatible carrier.

In another embodiment, the invention provides a method of delivering a transgene to a cell involving the step of contacting the cell with any AAV disclosed herein. In another embodiment, the invention provides a method of treating a subject from a disorder or disease associated with abnormal activity of an endogenous protein involving the step of administering to the subject an effective amount of an AAV disclosed herein where the AAV has a transgene that encodes a biologically active copy of the protein. In yet another embodiment, the methods involve delivering a transgene to a liver cell.

In further embodiment, the invention provides for a composition comprising any of the AAV of the invention for delivering a transgene to a cell, such as a liver cell. In addition, the invention provides for use of any of the AAV of the invention for the preparation of a medicament for delivering a transgene to a cell.

In one embodiment, the invention provides for an isolated adeno-associated virus (AAV) capsid protein, wherein the capsid protein comprises (i) an amino acid sequence that is at least 95%, 96%, 97%, 98%, or 99% identical to the VP1 amino acid sequence of any one of SEQ ID NOS:1-7 or the VP2 or VP3 region of any one of SEQ ID NOS:1-7 or (ii) a VP1 amino acid sequence comprising any one of SEQ ID NOS:1-7 or the VP2 or VP3 region of any one of SEQ ID NOS:1-7. In certain embodiments, the capsid protein is linked to a heterologous amino acid sequence. The invention also provides for non-naturally occurring AAV particles having or comprising any of these capsid proteins. In certain embodiments, the non-naturally occurring AAV particle comprising any of the above described VP1, VP2 or VP3 capsid proteins comprises a nucleic acid having AAV inverted terminal repeats and a transgene comprising a heterologous gene operably linked to regulatory sequences which direct expression of the heterologous gene in a host cell. In other embodiments, the non-naturally occurring AAV particle comprising any of the VP1, VP2 or VP3 capsid sequences described herein comprises a heterologous transgene operably linked to regulatory sequences that control transgene expression in a host cell. As used herein, the terms "heterologous gene" or "heterologous regulatory sequence" means that the referenced gene or regulatory sequence is not naturally present in the AAV vector or particle and is artificially introduced therein. The term "transgene" refers to a nucleic acid that comprises both a heterologous gene and regulatory sequences that are operably linked to the heterologous gene that control expression of that gene in a host cell.

The invention also provides for a polynucleotide comprising a nucleotide sequence encoding an adeno-associated virus (AAV) capsid protein, wherein the capsid protein comprises (i) an amino acid sequence that is at least 95%, 96%, 97%, 98% or 99% identical to the VP1 amino acid sequence of any one of SEQ ID NOS:1-7 or the VP2 or VP3 region of any one of SEQ ID NOS:1-7 or (ii) a VP1 amino acid sequence comprising any one of SEQ ID NOS:1-7 or the VP2 or VP3 region of any one of SEQ ID NOS:1-7, wherein the polynucleotide is operatively linked to a heterologous regulatory control sequence. As such, it is understood that the polynucleotides of the present invention are non-naturally occurring. The invention also provides for vectors comprising any of these polynucleotide sequences operably linked to a heterologous regulatory sequence and compositions comprising these vectors, including pharmaceutical compositions.

In another embodiment, the invention provides for an isolated adeno-associated virus (AAV) vector comprising a capsid encoded by a polynucleotide sequence encoding a capsid protein and a heterologous transgene sequence, wherein the capsid protein comprises (i) an amino acid sequence that is at least 95%, 96%, 97%, 98% or 99% identical to the VP1 amino acid sequence of any one of SEQ ID NOS:1-7 or the VP2 or VP3 region of any one of SEQ ID NOS:1-7 or (ii) a VP1 amino acid sequence comprising any one of SEQ ID NOS:1-7 or the VP2 or VP3 region of any one of SEQ ID NOS:1-7. The invention also provides for compositions comprising these AAV vectors, including pharmaceutical compositions.

In another embodiment, the invention provides for an adeno-associated virus (AAV) comprising a capsid protein, wherein the capsid protein comprises a functional fragment of any one of SEQ ID NOS: 1-7, and further comprising a transgene comprising a heterologous gene operably linked to a regulatory sequence that controls expression of the heterologous gene in a host cell. For example, the functional fragment comprises one or more of the variable regions (VR), the constant regions which are located between the variable regions, the GBS domain, and the GH loop of the amino acid sequence of any one of SEQ ID NO: 1-7. The invention also provides for compositions comprising these AAV vectors, including pharmaceutical compositions.

In a further embodiment, the invention provides for an adeno-associated virus comprising a capsid protein, wherein the capsid protein comprises an amino acid sequence encoded by a nucleotide sequence that hybridizes to a nucleotide sequence encoding (i) an amino acid sequence of any one of SEQ ID NO: 1-7, (ii) the VP2 region of the amino acid sequence of any one of SEQ ID NO: 1-7, or the VP3 region of the amino acid sequence of any one of SEQ ID NO: 1-7, and further comprising a transgene comprising a heterologous gene operably linked to a regulatory sequence that controls expression of the heterologous gene in a host cell. For example, the nucleotide sequence hybridized to a nucleotide sequence encoding a capsid protein or a functional fragment of a capsid protein of the invention under stringent conditions. The invention also provides for compositions comprising these AAV vectors, including pharmaceutical compositions.

The "variable regions" refer to the nine variable regions within the VP1 sequence of an AAV capsid protein. The variable regions (VR) are referred to herein as VR I, VR II, VR III VR IV, VR V, VR VI, VR VII, VR VIII and VR IX and their respective locations in various VP1 sequences are herein described. The VR exhibit the highest sequence and structural variation within the AAV VP1 capsid sequence and may also have roles in receptor attachment, transcriptional activation of transgenes, tissue transduction and antigenicity.

The "glycan binding sequence (GBS)" or "GBS domain" or "GBS region" refer to the amino acid sequence located between VR IV and VR V that governs the glycan binding specificity of the viral capsid. The locations of the GBS regions in various AAV VP1 amino acid sequences are herein described, and those from other AAV VP1 amino acid sequences are known in the art and/or may be routine identified.

The "GH loop" refers to a loop sequence that is flanked by β-strand G and β-strand H within the internal β-barrel of the capsid protein. The "GH loop" sequence comprises variable region VR IV through VR VIII, including the encompassed GBS sequence and all interspersed conserved backbone sequence from the donor. The locations of the GH loop regions in various AAV VP1 amino acid sequences are herein described and those from other AAV VP1 amino acid sequences may be routinely identified.

In regard to the herein described locations of the VR, GBS and GH loop regions, it is noted that the location of the N-terminal and/or C-terminal ends of those regions may vary by from up to 1 amino acid, 2 amino acids, 3 amino acids, 4 amino acids or 5 amino acids from the amino acid locations of those regions as they are explicitly described herein (particularly in Table 2). Novel capsid sequence comprising substituted VR, GBS and/or GH loop region(s) that vary from up to 5 amino acids on the N-terminal and/or C-terminal end as herein defined are encompassed by the present invention.

The invention provides for methods of producing a recombinant adeno-associated virus (AAV) particle comprising the steps of: culturing a cell that has been transfected with any of the AAV vectors of the invention and recovering recombinant AAV particle from the supernatant of the transfected cell. In addition, the invention provides for viral particles comprising any of the viral vectors or capsid proteins of the invention and cells comprising these viral vectors.

One embodiment of the invention provides a method of producing any of the recombinant AAV described herein by culturing a viral production cell into which has been introduced a first nucleic acid vector having 5' and 3' AAV inverted terminal repeat sequences flanking a transgene having a heterologous gene operably linked to regulatory sequences that control expression of the heterologous gene in a host cell, and a second nucleic acid vector having AAV rep and cap nucleic acids sequences, wherein said cap nucleic acid sequence encodes an AAV capsid that is at least 95% identical to any of SEQ ID NOS:1-7; and recovering the AAV from the supernatant of the viral production cell culture. In another embodiment the viral production cell is a mammalian. In a preferred embodiment the mammalian cell is a HEK293 cell.

In another embodiment, the invention provides for methods of treating a patient suffering from a disorder or disease comprising administering to the patient an effective amount of any of the AAV vectors or virus of the invention.

In a further embodiment, the invention provides for use of any of the AAV vectors or virus of the invention for preparation of a medicament for the treatment of a disorder or disease. The invention also provides for compositions comprising any of the AAV vectors or virus of the invention for the treatment of a disease or disorder.

In yet another embodiment, the disease or disorder in a subject is associated with abnormal activity of an endogenous protein. As used herein "endogenous protein" means a protein or gene product encoded by the genome of the subject suffering from the disease or disorder.

An "AAV virion" or "AAV viral particle" or "AAV vector particle" or "AAV virus" refers to a viral particle composed of at least one AAV capsid protein and an encapsidated polynucleotide AAV vector. If the particle comprises a heterologous polynucleotide (i.e. a polynucleotide other than a wild-type AAV genome such as a transgene to be delivered to a mammalian cell), it is typically referred to as a "recombinant AAV vector particle" or simply an "AAV vector". Production of AAV vector particles necessarily includes production of AAV vector genome, as such a vector genome is contained within an AAV vector particle. It is understood that reference to the polynucleotide AAV vector construct encapsulated within the vector particle, and replication thereof, refers to the AAV vector genome.

The invention also provides for cells comprising any of the AAV vectors of the invention, and viral particles produced by these cells of the invention.

The term "inverted terminal repeat (ITR)" as used herein refers to the art-recognized regions found at the 5' and 3' termini of the AAV genome which function in cis as origins of DNA replication and as packaging signals for the viral genome. AAV ITRs, together with the AAV rep coding region, provide for efficient excision and rescue from a plasmid vector, and integration of a nucleotide sequence interposed between two flanking ITRs into a host cell genome. Sequences of certain AAV-associated ITRs are disclosed by Yan et al., *J. Virol.* 79(1):364-379 (2005) which is herein incorporated by reference in its entirety.

The phrase "helper functions for generating a productive AAV infection" as used herein refers to AAV-derived coding sequences that can be expressed to provide AAV gene products that, in turn, function in trans for productive AAV replication. Thus, AAV helper functions include the rep and cap regions. The rep expression products have been shown to possess many functions, including, among others: recognition, binding and nicking of the AAV origin of DNA replication; DNA helicase activity; and modulation of transcription from AAV (or other heterologous) promoters. The cap expression products supply necessary packaging functions. AAV helper functions are used herein to complement AAV functions in trans that are missing from AAV vectors. Helper functions for generating a productive AAV infection also may include certain helper functions from baculovirus, herpes virus, adenovirus, or vaccinia virus.

In some embodiments, the viral construct comprises a nucleotide sequence encoding AAV rep and cap genes.

The term "AAV rep gene" as used herein refers to the art-recognized region of the AAV genome which encodes the replication proteins of the virus which are required to replicate the viral genome and to insert the viral genome into a host genome during latent infection. For a further description of the AAV rep coding region, see, e.g., Muzyczka et al., *Current Topics in Microbiol. and Immunol.* 158:97-129 (1992); Kotin et al., *Human Gene Therapy* 5:793-801 (1994), the disclosures of which are incorporated herein by reference in their entireties. The rep coding region, as used herein, can be derived from any viral serotype, such as the AAV serotypes described herein. The region need not include all of the wild-type genes but may be altered, e.g., by the insertion, deletion or substitution of nucleotides, so long as the rep genes retain the desired functional characteristics when expressed in a suitable recipient cell.

The term "AAV cap gene" as used herein refers to the art-recognized region of the AAV genome which encodes the coat proteins of the virus which are required for packaging the viral genome. For a further description of the cap coding region, see, e.g., Muzyczka et al., *Current Topics in Microbiol. and Immunol.* 158:97-129 (1992); Kotin et al., *Human Gene Therapy* 5:793-801 (1994), the disclosures of which are incorporated herein by reference in their entireties. The AAV cap coding region, as used herein, can be derived from any AAV serotype, as described herein. The region need not include all of the wild-type cap genes but may be altered, e.g., by the insertion, deletion or substitution of nucleotides, so long as the genes provide for sufficient packaging functions when present in a host cell along with an AAV vector.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al., *Virology* 52:456 (1973); Sambrook et al., *Molecular Cloning: A Laboratory Manual*, Cold Spring Harbor Laboratories, New York (1989); Davis et al., Basic *Methods in Molecular Biology*, Elsevier (1986); Chu et al., *Gene* 13:197 (1981), the disclosures of which are incorporated herein by reference in their entireties. Such techniques can be used to introduce one or more exogenous DNA moieties, such as a nucleotide integration vector and other nucleic acid molecules, into suitable host cells. The term captures chemical, electrical, and viral-mediated transfection procedures.

In yet another aspect, described herein is an AAV particle produced by a method described herein. In some embodiments, the AAV particle comprises in its genome at least one nucleotide encoding a heterologous protein.

The term "heterologous proteins or peptides" refer to any protein that is not expressed by wild type AAV including tags such as hexahistidine, FLAG, myc, polyhistidine, or labels or immunogens, adjuvants, selection markers, therapeutic proteins or targeting proteins or peptides, to name a few.

Exemplary heterologous protein described herein includes, but is not limited to, β-globin, hemoglobin, tissue plasminogen activator, and coagulation factors; colony stimulating factors (CSF); interleukins, such as IL-1, IL-2, IL-3, IL-4, IL-5, IL-6, IL-7, IL-8, IL-9, etc.; growth factors, such as keratinocyte growth factor (KGF), stem cell factor (SCF), fibroblast growth factor (FGF, such as basic FGF and acidic FGF), hepatocyte growth factor (HGF), insulin-like growth factors (IGFs), bone morphogenetic protein (BMP), epidermal growth factor (EGF), growth differentiation factor-9 (GDF-9), hepatoma derived growth factor (HDGF), myostatin (GDF-8), nerve growth factor (NGF), neurotrophins, platelet-derived growth factor (PDGF), thrombopoietin (TPO), transforming growth factor alpha (TGF-α), transforming growth factor beta (TGF-β), and the like; soluble receptors, such as soluble TNF-α receptors, soluble interleukin receptors (e.g., soluble IL-1 receptors and soluble type II IL-1 receptors), soluble γ/Δ T cell receptors, ligand-binding fragments of a soluble receptor, and the like; enzymes, such as α-glucosidase, imiglucerase, β-glucocerebrosidase, and alglucerase; enzyme activators, such as tissue plasminogen activator; chemokines, such as 1P-10, monokine induced by interferon-gamma (Mig), Groα/IL-8, RANTES, MIP-1α, MIP-1β, MCP-1, PF-4, and the like; angiogenic agents, such as vascular endothelial growth factors (VEGFs, e.g., VEGF121, VEGF165, VEGF-C, VEGF-2), glioma-derived growth factor, angiogenin, angiogenin-2; and the like; anti-angiogenic agents, such as a soluble VEGF receptor; protein vaccine; neuroactive peptides, such as nerve growth factor (NGF), bradykinin, cholecystokinin, gastin, secretin, oxytocin, gonadotropin-releasing hormone, beta-endorphin, enkephalin, substance P, somatostatin, prolactin, galanin, growth hormone-releasing hormone, bombesin, dynorphin, warfarin, neurotensin, motilin, thyrotropin, neuropeptide Y, luteinizing hormone, calcitonin, insulin, glucagons, vasopressin, angiotensin II, thyrotropin-releasing hormone, vasoactive intestinal peptide, a sleep peptide, and the like; thrombolytic agents; atrial natriuretic peptide; relaxin; glial fibrillary acidic protein; follicle stimulating hormone (FSH); human alpha-1 antitrypsin; leukemia inhibitory factor (LIF); tissue factors, luteinizing hormone; macrophage activating factors; tumor necrosis factor (TNF); neutrophil chemotactic factor (NCF); tissue inhibitors of metalloproteinases; vasoactive intestinal peptide; angiogenin; angiotropin; fibrin; hirudin; IL-1 receptor antagonists; ciliary neurotrophic factor (CNTF); brain-derived neurotrophic factor (BDNF); neurotrophins 3 and 4/5 (NT-3 and 4/5); glial cell derived neurotrophic factor (GDNF); aromatic amino acid decarboxylase (AADC); Factor VIII, Factor IX, Factor X; dystrophin or nini-dystrophin; lysosomal acid lipase; phenylalanine hydroxylase (PAH); glycogen storage disease-related enzymes, such as glucose-6-phosphatase, acid maltase, glycogen debranching enzyme, muscle glycogen phosphorylase, liver glycogen phosphorylase, muscle phosphofructokinase, phosphorylase kinase, glucose transporter, aldolase A, β-enolase, glycogen synthase; and lysosomal enzymes.

DESCRIPTION OF DRAWINGS

This patent or application file contains at least one drawing executed in color. Copies of this patent or patent application publication with color drawing(s) will be provided by the United States Patent and Trademark Office upon request and payment of the necessary fee.

FIG. 1 is a set of tables showing the relative tissue specificity of infectivity of AAV having the designated novel capsid proteins. The data is presented as Total Flux in each tissue (photons/sec/cm$^2$/radian). For each tissue the top row represents the average flux and the bottom row represents the standard deviation.

DETAILED DESCRIPTION

Figure 2:
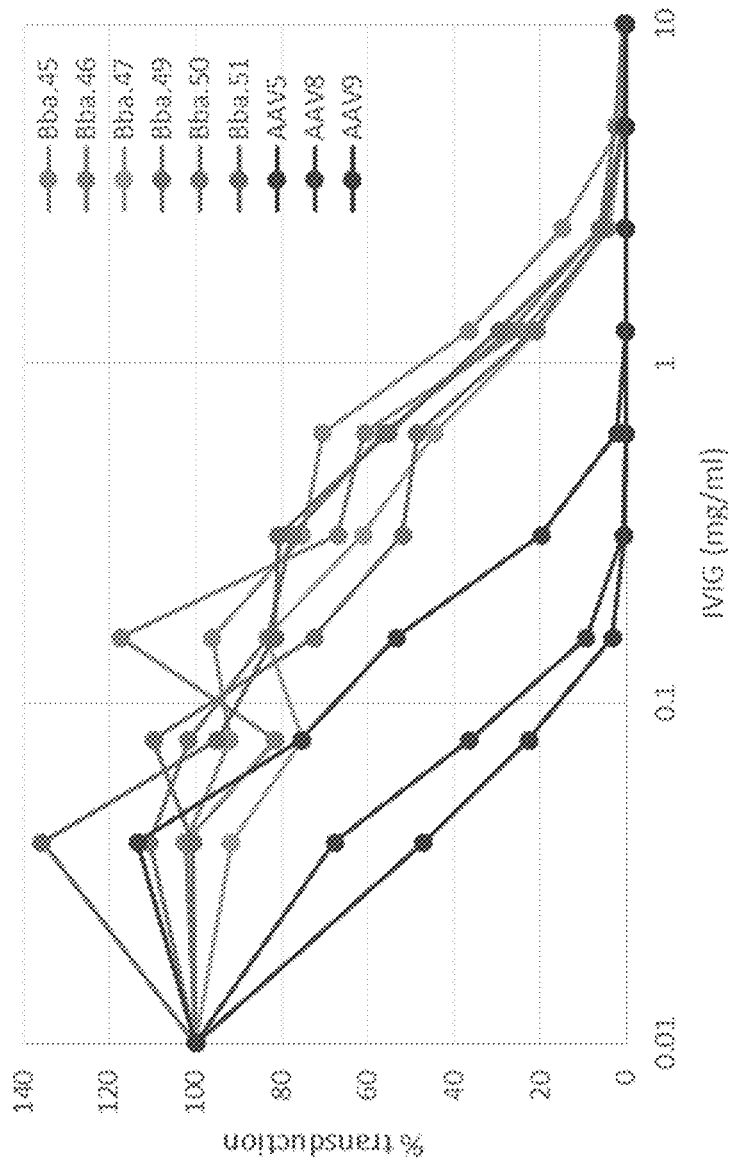
FIG. 2 provides data from an IVIG neutralization assay for the novel capsids: Bba-45, Bba-46, Bba-47, Bba-49, Bba-50 and Bba-51 and control capsids: AAV5, AAV8 and AAV9. This assay demonstrates that the novel capsids exhibited WIG resistant properties.

The invention provides for novel AAV capsid proteins, nucleic acid encoding those capsid proteins and AAV virus comprising those novel capsid proteins. In some embodiments, the AAV capsid proteins were isolated and identified from various mammalian tissues. The amino acid sequences of the novel AAV capsid VP1 proteins are set out as SEQ ID NOS:1-7, and the locations of the associated VP2 and VP3 regions are disclosed herein.

AAV Vectors

As used herein, the term "AAV" is a standard abbreviation for adeno-associated virus. Adeno-associated virus is a single-stranded DNA parvovirus that grows only in cells in which certain functions are provided by a co-infecting helper virus. There are currently at least thirteen serotypes of AAV that have been characterized, as shown below in Table 1. General information and reviews of AAV can be found in, for example, Carter, *Handbook of Parvoviruses*, Vol. 1, pp. 169-228 (1989), and Berns, *Virology*, pp. 1743-1764, Raven Press, (New York, 1990). However, it is fully expected that these same principles will be applicable to additional AAV serotypes since it is well known that the various serotypes are quite closely related, both structurally and functionally, even at the genetic level. (See, for example, Blacklowe, pp. 165-174 of *Parvoviruses and Human Disease*, J. R. Pattison, ed. (1988); and Rose, *Comprehensive Virology* 3:1-61 (1974)). For example, all AAV serotypes apparently exhibit very similar replication properties mediated by homologous rep genes; and all bear three related capsid proteins such as those expressed in AAV6. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control.

An "AAV vector" as used herein refers to a vector comprising one or more polynucleotides of interest (or transgenes) that are flanked by AAV terminal repeat sequences (ITRs). Such AAV vectors can be replicated and packaged into infectious viral particles when present in a host cell that has been transfected with a vector encoding and expressing rep and cap gene products.

AAV "rep" and "cap" genes are genes encoding replication and encapsidation proteins, respectively. AAV rep and cap genes have been found in all AAV serotypes examined to date, and are described herein and in the references cited. In wild-type AAV, the rep and cap genes are generally found adjacent to each other in the viral genome (i.e., they are "coupled" together as adjoining or overlapping transcriptional units), and they are generally conserved among AAV serotypes. AAV rep and cap genes are also individually and collectively referred to as "AAV packaging genes." The AAV cap gene in accordance with the present invention encodes a Cap protein which is capable of packaging AAV vectors in the presence of rep and adeno helper function and is capable of binding target cellular receptors. In some embodiments, the AAV cap gene encodes a capsid protein having an amino acid sequence derived from a particular AAV serotype, for example the serotypes shown in Table 1.

TABLE 1

| AAV serotypes | |
|---|---|
| AAV Serotype | Genbank Accession No. |
| AAV-1 | NC_002077.1 |
| AAV-2 | NC_001401.2 |

TABLE 1-continued

| AAV serotypes | |
|---|---|
| AAV Serotype | Genbank Accession No. |
| AAV-3 | NC_001729.1 |
| AAV-3B | AF028705.1 |
| AAV-4 | NC_001829.1 |
| AAV-5 | NC_006152.1 |
| AAV-6 | AF028704.1 |
| AAV-7 | NC_006260.1 |
| AAV-8 | NC_006261.1 |
| AAV-9 | AX753250.1 |
| AAV-10 | AY631965.1 |
| AAV-11 | AY631966.1 |
| AAV-12 | DQ813647.1 |
| AAV-13 | EU285562.1 |

The AAV sequences employed for the production of AAV can be derived from the genome of any AAV serotype. Generally, the AAV serotypes have genomic sequences of significant homology at the amino acid and the nucleic acid levels, provide a similar set of genetic functions, produce virions which are essentially physically and functionally equivalent, and replicate and assemble by practically identical mechanisms. For the genomic sequence of AAV serotypes and a discussion of the genomic similarities see, for example, GenBank Accession number U89790; GenBank Accession number J01901; GenBank Accession number AF043303; GenBank Accession number AF085716; Chiorini et al., *J. Vir.* 71:6823-33 (1997); Srivastava et al., *J. Vir.* 45:555-64 (1983); Chiorini et al., *J. Vir.* 73:1309-1319 (1999); Rutledge et al., *J. Vir.* 72:309-319 (1998); and Wu et al., *J. Vir.* 74: 8635-47 (2000).

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural capsid (Cap) proteins. There are three different viral particle (VP) proteins that form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. The Rep genes encode the Rep proteins, Rep78, Rep68, Rep52, and Rep40. Rep78 and Rep68 are transcribed from the p5 promoter, and Rep 52 and Rep40 are transcribed from the p19 promoter. The cap genes encode the VP proteins, VP1, VP2, and VP3. The cap genes are transcribed from the p40 promoter.

In some embodiments, a nucleic acid sequence encoding an AAV capsid protein is operably linked to regulatory expression control sequences for expression in a specific cell type, such as Sf9 or HEK cells. Techniques known to one skilled in the art for expressing foreign genes in insect host cells or mammalian host cells can be used to practice the invention. Methodology for molecular engineering and expression of polypeptides in insect cells is described, for example, in Summers and Smith. *A Manual of Methods for Baculovirus Vectors and Insect Culture Procedures*, Texas Agricultural Experimental Station Bull. No. 7555, College Station, Tex. (1986); Luckow. 1991. In Prokop et al., *Cloning and Expression of Heterologous Genes in Insect Cells with Baculovirus Vectors' Recombinant DNA Technology and Applications,* 97-152 (1986); King, L. A. and R. D. Possee, *The baculovirus expression system*, Chapman and Hall, United Kingdom (1992); O'Reilly, D. R., L. K. Miller, V. A. Luckow, *Baculovirus Expression Vectors: A Laboratory Manual*, New York (1992); W. H. Freeman and Richardson, C. D., *Baculovirus Expression Protocols, Methods in Molecular Biology*, volume 39 (1995); U.S. Pat. No. 4,745,051; US2003148506; and WO 03/074714. A particularly suitable promoter for transcription of a nucleotide sequence encoding an AAV capsid protein is e.g. the polyhedron promoter. However, other promoters that are active in insect cells are known in the art, e.g. the p10, p35 or IE-1 promoters and further promoters described in the above references are also contemplated.

Use of insect cells for expression of heterologous proteins is well documented, as are methods of introducing nucleic acids, such as vectors, e.g., insect-cell compatible vectors, into such cells and methods of maintaining such cells in culture. See, for example, *METHODS IN MOLECULAR BIOLOGY*, ed. Richard, Humana Press, N J (1995); O'Reilly et al., *BACULOVIRUS EXPRESSION VECTORS, A LABORATORY MANUAL*, Oxford Univ. Press (1994); Samulski et al., *J. Vir.* 63:3822-8 (1989); Kajigaya et al., *Proc. Nat'l. Acad. Sci. USA* 88:4646-50 (1991); Ruffing et al., *J. Vir.* 66:6922-30 (1992); Kirnbauer et al., *Vir.* 219:37-44 (1996); Zhao et al., *Vir.* 272:382-93 (2000); and Samulski et al., U.S. Pat. No. 6,204,059. In some embodiments, the nucleic acid construct encoding AAV in insect cells is an insect cell-compatible vector. An "insect cell-compatible vector" or "vector" as used herein refers to a nucleic acid molecule capable of productive transformation or transfection of an insect or insect cell. Exemplary biological vectors include plasmids, linear nucleic acid molecules, and recombinant viruses. Any vector can be employed as long as it is insect cell-compatible. The vector may integrate into the insect cell's genome but the presence of the vector in the insect cell need not be permanent and transient episomal vectors are also included. The vectors can be introduced by any means known, for example by chemical treatment of the cells, electroporation, or infection. In some embodiments, the vector is a baculovirus, a viral vector, or a plasmid. In a more preferred embodiment, the vector is a baculovirus, i.e. the construct is a baculoviral vector. Baculoviral vectors and methods for their use are described in the above cited references on molecular engineering of insect cells.

Baculoviruses are enveloped DNA viruses of arthropods, two members of which are well known expression vectors for producing recombinant proteins in cell cultures. Baculoviruses have circular double-stranded genomes (80-200 kbp) which can be engineered to allow the delivery of large genomic content to specific cells. The viruses used as a vector are generally *Autographa californica* multicapsid nucleopolyhedrovirus (AcMNPV) or *Bombyx mori* (Bm) NPV) (Kato et al., *Appl. Microbiol. Biotechnol.* 85(3):459-470 (2010)). Baculoviruses are commonly used for the infection of insect cells for the expression of recombinant proteins. In particular, expression of heterologous genes in insects can be accomplished as described in for instance U.S. Pat. No. 4,745,051; Friesen et al., *Curr. Top. Microbiol. Immunol.* 131:31-49. (1986); EP 127,839; EP 155,476; Miller et al., *Ann. Rev. of Microbiol.* 42: 177-199 (1988); Carbonell et al., *Gene* 73(2):409-18 (1988); Maeda et al., *Nature* 315(6020):592-4 (1985); Lebacq-Verheyden et al., *Mol. Cell Biol.* 8(8):3129-35 (1988); Smith et al., *Proc. Natl. Acad. Sci, USA*. 82(24):8404-8 (1985); Miyajima et al., *Gene* 58(2-3):273-81 (1987); and Martin et al., *DNA* 7(2): 99-106 (1988). Numerous baculovirus strains and variants and corresponding permissive insect host cells that can be used for protein production are described in Luckow et al., *Nature Biotechnology* 6:47-55 (1988), and Maeda et al., *Nature* 315(6020):592-4 (1985).

Novel AAV Capsid Protein

In a first aspect, the invention provides for novel AAV capsid proteins that were isolated from various mammalian tissues. The novel AAV VP1 capsid proteins are provided as SEQ ID NOS:1-7 and the locations of the associated VP2 and VP3 regions are described herein. The invention also provides for polynucleotides comprising a nucleotide sequence encoding these novel AAV capsid proteins. The invention provides the amino acid sequences of the novel AAV capsid proteins (referred herein collectively as the "AAV capsid proteins of the invention"), and the nucleic acid sequences encoding the AAV capsid proteins of the invention. Also provided are fragments of these AAV capsid nucleic acid and amino acid sequences of the invention. Each of these sequences may be readily utilized in a variety of vector systems and host cells. Desirable fragments of the capsid VP1 proteins include VP2, VP3 and variable regions, the GBS domain and the GH loop, and polynucleotide sequences encoding these proteins. These fragments may be readily utilized in a variety of vector systems and host cells. Such fragments may be used alone, in combination with other AAV sequences or fragments, or in combination with elements from other AAV or non-AAV viral sequences. In one particularly desirable embodiment, a vector contains the AAV capsid sequences of the invention.

The AAV capsid sequences of the invention and fragments thereof are useful in production of rAAV, and are also useful as antisense delivery vectors, gene therapy vectors, or vaccine vectors. The invention further provides nucleic acid molecules, gene delivery vectors, and host cells which contain the novel AAV capsid sequences of the invention.

Suitable fragments can be determined using the information provided herein. Alignments are performed using any of a variety of publicly or commercially available Multiple Sequence Alignment Programs, such as "Clustal W", accessible through Web Servers on the internet. Alternatively, Vector NTI utilities are also used. There are also a number of algorithms known in the art which can be used to measure nucleotide sequence identity, including those contained in the programs described above. As another example, polynucleotide sequences can be compared using FASTA, a program in GCG Version 6.1. FASTA provides alignments and percent sequence identity of the regions of the best overlap between the query and search sequences. For instance, percent sequence identity between nucleic acid sequences can be determined using FASTA with its default parameters (a word size of 6 and the NOPAM factor for the scoring matrix) as provided in GCG Version 6.1, herein incorporated by reference. Similar programs are available for amino acid sequences, e.g., the "Clustal X" program. Additional sequence alignment tools that can be used are provided by (protein sequence alignment; (EMBOSS Needle—ebi.ac.uk/Tools/psa/emboss_needle/)) and (nucleic acid alignment; EMBOSS Needle—ebi.ac.uk/Tools/psa/emboss_needle/nucleotide.html)). Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs.

The terms "substantial identity", "substantial homology" or "substantial similarity," when referring to a nucleic acid, or fragment thereof, indicates that, when optimally aligned with appropriate nucleotide insertions or deletions with another nucleic acid (or its complementary strand), there is nucleotide sequence identity in at least about 95 to 99% of the aligned sequences such as 95% identity, 96% identity, 97% identity, 98% identity and 99% identity. Preferably, the homology is over the full-length of the two sequences being compared, or an open reading frame thereof, or another suitable fragment which is at least 15 nucleotides in length. Examples of suitable fragments are described herein. Also included in the nucleic acid sequences of the invention are natural variants and engineered modifications of the nucleic acids encoding the AAV capsids of the invention and its complementary strand. Such modifications include, for example, labels which are known in the art, methylation, and substitution of one or more of the naturally occurring nucleotides with a degenerate nucleotide.

By the term "highly conserved" is meant at least 80% identity, preferably at least 90% identity, and more preferably, over 97% identity. Identity is readily determined by one of skill in the art by resort to algorithms and computer programs known by those of skill in the art.

The term "percent sequence identity" or "identical" in the context of nucleic acid sequences or amino acid sequences refers to the residues in the two sequences which are the same when aligned for maximum correspondence. The length of sequence identity comparison may be over the full-length of the two sequences being compared, the full-length of a gene coding sequence, or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length, and may be up to about 700 amino acids. Examples of suitable fragments are described herein.

The novel capsids of the invention may comprise one or more additional conservative amino acid substitutions that do not affect the biological and/or immunogenic activity of the polypeptide. The term "conservative amino acid substitution" refers to a substitution of a native amino acid residue with a nonnative residue, including naturally occurring and nonnaturally occurring amino acids, such that there is little or no effect on the polarity or charge of the amino acid residue at that position. For example, a conservative substitution results from the replacement of a non-polar residue in a polypeptide with any other non-polar residue. Further, any native residue in the polypeptide may also be substituted with alanine, according to the methods of "alanine scanning mutagenesis". Naturally occurring amino acids are characterized based on their side chains as follows: basic: arginine, lysine, histidine; acidic: glutamic acid, aspartic acid; uncharged polar: glutamine, asparagine, serine, threonine, tyrosine; and non-polar: phenylalanine, tryptophan, cysteine, glycine, alanine, valine, proline, methionine, leucine, norleucine, isoleucine. General rules for amino acid substitutions are set forth in the Table below.

Conservative Amino Acid Substitutions

| Original Residues | Exemplary Substitutions | Preferred Substitutions |
| --- | --- | --- |
| Ala | Val, Leu, Ile | Val |
| Arg | Lys, Gln, Asn | Lys |

-continued

Conservative Amino Acid Substitutions

| Original Residues | Exemplary Substitutions | Preferred Substitutions |
| --- | --- | --- |
| Asn | Gln | Gln |
| Asp | Glu | Glu |
| Cys | Ser, Ala | Ser |
| Gln | Asn | Asn |
| Glu | Asp | Asn |
| Gly | Pro, Ala | Ala |
| His | Asn, Gln, Lys, Arg | Arg |
| Ile | Leu, Val, Met, Ala, Phe, | Leu |
| Leu | Norleucine, Ile, Val, Met, | Leu |
| Lys | Arg, 1,4 Diaminobutyric | Arg |
| Met | Leu, Phe, Ile | Leu |
| Phe | Leu, Val, Ile, Ala, Tyr | Arg |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, | Leu |

The novel capsids of the invention may be encoded by polynucleotides that are substantially equivalent to the nucleic acid sequence encoding the amino acid sequence of SEQ ID NO: 1-7. Polynucleotides according to the invention can have, e.g., at least 65%, at least 70%, at least 75%, at least 80%, 81%, 82%, 83%, 84%, 85%, 86%, 87%, 88%, or 89%, more typically at least 90%, 91%, 92%, 93%, or 94% and even more typically at least 95%, 96%, 97%, 98% or 99% sequence identity to the polynucleotide sequences encoding the modified polypeptide amino acid sequences of the invention.

Included within the scope of the nucleic acid sequences of the invention are nucleic acid sequence fragments that hybridize under stringent conditions to the nucleotide sequences encoding the novel capsids of the invention, which fragment is greater than about 5 nucleotides, preferably 7 nucleotides, more preferably greater than 9 nucleotides and most preferably greater than 17 nucleotides. Fragments of, e.g., 15, 17, or 20 nucleotides or more that are selective for (i.e., specifically hybridize to any one of the polynucleotides of the invention) are contemplated. Probes capable of specifically hybridizing to a polynucleotide can differentiate polynucleotide sequences of the invention from other polynucleotide sequences in the same family of genes or can differentiate genes from other bacterial genes, and are preferably based on unique nucleotide sequences.

The term "stringent" is used to refer to conditions that are commonly understood in the art as stringent. Hybridization stringency is principally determined by temperature, ionic strength, and the concentration of denaturing agents such as formamide. Examples of stringent conditions for hybridization and washing are 0.015 M sodium chloride, 0.0015M sodium citrate at 65-68° C. or 0.015 M sodium chloride, 0.0015M sodium citrate, and 50% formamide at 42° C. See Sambrook et al., Molecular Cloning: A Laboratory Manual, 2.sup.nd Ed., Cold Spring Harbor Laboratory, (Cold Spring Harbor, N.Y. 1989). More stringent conditions (such as higher temperature, lower ionic strength, higher formamide, or other denaturing agent) may also be used, however, the rate of hybridization will be affected. In instances wherein hybridization of deoxyoligonucleotides is concerned, additional exemplary stringent hybridization conditions include washing in 6×SSC 0.05% sodium pyrophosphate at 37° C. (for 14-base oligos), 48° C. (for 17-base oligos), 55° C. (for 20-base oligos), and 60° C. (for 23-base oligos).

Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, NaDodSO4 (SDS), ficoll, Denhardt's solution, sonicated salmon sperm DNA (or other non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4, however, at typical ionic strength conditions, the rate of hybridization is nearly independent of pH. See Anderson et al., Nucleic Acid Hybridisation: A Practical Approach, Ch. 4, IRL Press Limited (Oxford, England). Hybridization conditions can be adjusted by one skilled in the art in order to accommodate these variables and allow DNAs of different sequence relatedness to form hybrids.

As described herein, the vectors of the invention containing or comprising the AAV capsid proteins of the invention are particularly well-suited for use in applications in which the neutralizing antibodies diminish the effectiveness of other AAV serotype based vectors, as well as other viral vectors. The rAAV vectors of the invention are particularly advantageous in rAAV re-administration and repeat gene therapy.

Also included within the invention are fragments of the nucleic acids encoding the AAV capsid proteins of the invention, their complementary strand, cDNA and RNA complementary thereto. Suitable fragments are at least 15 nucleotides in length, and encompass functional fragments, i.e., fragments which are of biological interest. Such fragments include the sequences encoding the three variable proteins (VP) of the capsid which are alternative splice variants: VP1, VP2 and VP3. Other suitable fragments of the nucleic acids encoding the AAV capsids of the invention include the fragment which contains the start codon for the capsid protein, and the fragments encoding the variable regions of the VP1 capsid protein, which are described herein.

The invention is not limited to the AAV capsid amino acid sequences, peptides and proteins expressed from the AAV nucleic acid sequences of the invention and encompasses amino acid sequences, peptides and proteins generated by other methods known in the art, including, e.g., by chemical synthesis, by other synthetic techniques, or by other methods. For example, the sequences of any of the capsids described herein can be readily generated using a variety of techniques.

Suitable production techniques are well known to those of skill in the art. See, e.g., Sambrook et al, *Molecular Cloning: A Laboratory Manual*, Cold Spring Harbor Press (Cold Spring Harbor, N.Y.). Alternatively, peptides can also be synthesized by the well-known solid phase peptide synthesis methods (Merrifield, *J. Am. Chem. Soc.*, 85:2149 (1962); Stewart and Young, *Solid Phase Peptide Synthesis Freeman*, (San Francisco, 1969) pp. 27-62. These and other suitable production methods are within the knowledge of those of skill in the art and are not a limitation of the present invention.

The AAV capsid is composed of three proteins, VP1, VP2 and VP3, which are alternative splice variants. The full-length capsid sequence is referred to as VP1 which encompasses the spliced variants referred to as VP2 and VP3. The invention also provides for other functional fragments of the AAV capsid proteins of the invention. Other desirable fragments of the capsid protein include the variable regions (VR), the constant regions which are located between the variable regions, the GBS domain, and the GH loop. Other desirable fragments of the capsid protein include the HPV themselves.

An algorithm has been developed to determine areas of sequence divergence in AAV2. (Chiorini et al, *J. Virol*, 73:1309-19 (1999); Rutledge et al, *J. Virol.*, 72:309-319 (1998)). Using this algorithm and/or the alignment techniques described herein, the VR of the novel AAV capsid sequences are determined. Using the alignment provided herein performed using the Clustal X program at default settings, or using other commercially or publicly available alignment programs at default settings, one of skill in the art can readily determine corresponding fragments of the novel AAV capsids of the invention.

Suitably, fragments of an AAV capsid protein are at least 8 amino acids in length, or at least 9 amino acids in length, or at least 10 amino acids in length, or least 20 amino acids in length, or 30 amino acids in length or at least 50 amino acids in length, or at least 75 amino acids in length, or at least 100 amino acids in length or 200 amino acids in length or 250 amino acids in length or 300 amino acids in length or 350 amino acids in length or 400 amino acids in length. However, fragments of other desired lengths may be readily utilized. All fragments of the invention retain biological activity of a capsid AAV protein. Such fragments may be produced recombinantly or by other suitable means, e.g., chemical synthesis.

The sequences, proteins, and fragments of the invention may be produced by any suitable means, including recombinant production, chemical synthesis, or other synthetic means. Such production methods are within the knowledge of those of skill in the art and are not a limitation of the present invention.

In addition to including the nucleic acid sequences provided in the figures and Sequence Listing, the present invention includes nucleic acid molecules and sequences which are designed to express the amino acid sequences, proteins and peptides of the AAV capsid proteins of the invention. Thus, the invention includes nucleic acid sequences which encode the following AAV capsid amino acid sequences and artificial AAV capsid proteins generated using these sequences and/or unique fragments thereof.

Production of AAV with the Capsid Proteins of the Invention

The invention encompasses AAV capsid protein sequences and the nucleic acids encoding these proteins of which are free of DNA and/or cellular material which these viruses are associated in nature. In another aspect, the present invention provides molecules which utilize the novel AAV sequences of the invention, including fragments thereof, for production of molecules useful in delivery of a heterologous gene or other nucleic acid sequences to a target cell.

In another aspect, the present invention provides molecules which utilize the AAV capsid protein sequences of the invention, including fragments thereof, for production of viral vectors useful in delivery of a heterologous gene or other nucleic acid sequences to a target cell.

The molecules of the invention which contain AAV capsid nucleic acid sequences include any genetic element (vector) which may be delivered to a host cell, e.g., naked DNA, a plasmid, phage, transposon, cosmid, episome, a protein in a non-viral delivery vehicle (e.g., a lipid-based carrier), virus, etc. which transfer the sequences carried thereon. The selected vector may be delivered by any suitable method, including transfection, electroporation, liposome delivery, membrane fusion techniques, high velocity DNA-coated pellets, viral infection and protoplast fusion. The methods used to construct any embodiment of this invention are known to those with skill in nucleic acid manipulation and include genetic engineering, recombinant engineering, and synthetic techniques. See, e.g., Sambrook et al, *Molecular Cloning: A Laboratory Manual*, Cold Spring Harbor Press, Cold Spring Harbor, N.Y.

In one embodiment, the vectors of the invention contain, at a minimum, sequences encoding the AAV capsid of the invention or a fragment thereof. In another embodiment, the vectors of the invention contain, at a minimum, sequences encoding an AAV rep protein or a fragment thereof. Optionally, such vectors may contain both AAV cap and rep proteins. In vectors in which both AAV rep and cap are provided, the AAV rep and AAV cap sequences can both be of the same AAV serotype origin. Alternatively, the present invention provides vectors in which the rep sequences are from an AAV serotype which differs from that which is providing the cap sequences. In one embodiment, the rep and cap sequences are expressed from separate sources (e.g., separate vectors, or a host cell and a vector). In another embodiment, these rep sequences are fused in frame to cap sequences of a different AAV serotype to form a chimeric AAV vector.

Thus, in one embodiment, the vectors described herein contain nucleic acid sequences encoding an intact AAV capsid protein of any one of amino acid sequences SEQ ID NO: 1-7. In another example, it may be desirable to alter the start codon of the VP3 protein to GTG. Alternatively, the rAAV may contain one or more of the variable regions of one or more of the AAV capsid proteins of the invention, or other fragments. These modifications may be to increase expression, yield, and/or to improve purification in the selected expression systems, or for another desired purpose (e.g., to change tropism or alter neutralizing antibody epitopes).

The vectors described herein, e.g., a plasmid, are useful for a variety of purposes, but are particularly well suited for use in production of a rAAV containing a capsid comprising AAV sequences or a fragment thereof. These vectors, including rAAV, their elements, construction, and uses are described in detail herein.

VP1 of Novel Capsid Proteins

Novel AAV VP1 capsid proteins were isolated from baboon liver.

The VP1 sequence of a novel AAV capsid isolated from baboon (denoted as Bba.45) is set out as SEQ ID NO:1 (amino acids 1-742) and the locations of the associated variable regions and GBS region are defined in Table 2 below. The VP2 capsid protein spans amino acids 138-742 of SEQ ID NO:1 and the VP3 capsid protein spans amino acids 206-742 of SEQ ID NO:1.

MAADGYLPDWLEDNLSEGIREWWALKPGAPQPKANRQHQDNARGLVLPGY

KYLGPGNGLDKGEPVNEADAAALEHDKAYDQQLKSGDNPYLKYNHADAEF

QQRLATDTSFGGNLGKAVFQAKKRILEPLGLVEEGVKTAPGKKRPLEKTP

NRPTNPDSGKAPAKKKQKDGETADSARRALDFEDSGAGDGPPEGSSSGEM

SHDAEMRAAPGGNAVEAGQGADGVGNASGDWHCDSTWSEGRVTTTSTRTW

VLPTYNNHLYLRIGTTANSNTYNGFSTPWGYFDFNRFHCHFSPRDWQRLI

NNNWGLRPKSMRVKIFNIQVREVTTSNGETTVANNLTSTVQIFADSTYEL

-continued

PYVMDAGQEGSLPPFPNDVFMVPQYGYCGVVTGENQNQTDRNAFYCLEYF

PSQMLRTGNNFEISYQFEKVPFHSMYAHSQSLDRMMNPLLDQYLWHLQST

TTGNSLNQGTATTTYGKITTGDFAYYRKNWLPGACIKQQKFSKNASQNYK

IPASGGDALLKYDTHTTLNGRWSNMAPGPPMATAGAGDSDFSNSQLIFAG

PNQSGNTTTSSNNLLFTSEEEIATTNPRDTDMFGQIADNNQNATTAPHIA

NLDAMGIVPGMVWQNRDIYYQGPIWAKVPHTDGHFHPSPLMGGFGLKHPP

PQIFIKNTPVPANPNTTFSAARINSFLTQYSTGQVAVQIDWEIQKEHSKR

WNPEVQFTSNYGTQNSMLWAPDNAGNYHEPRAIGSRFLTHHL

The VP1 sequence of a novel AAV capsid isolated from baboon (denoted as Bba.46) is set out as SEQ ID NO:2 (amino acids 1-742) and the locations of the associated variable regions and GBS region are defined in Table 2 below. The VP2 capsid protein spans amino acids 138-742 of SEQ ID NO:2 and the VP3 capsid protein spans amino acids 206-742 of SEQ ID NO:2.

MAADGYLPDWLEDNLSEGIREWWALKPGAPQPKANQQHQDNARGLVLPGY

KYLGPGNGLDKGEPVNEADAAALEHDKAYDQQLKSGDNPYLKYNHADAEF

QQRLATDTSFGGNLGKAVFQAKKRILEPLGLVEEGVKTAPGKKRPLEKTP

NRPTNPDSGKAPAKKKQKDGETADSARRTLDFEDSGAGDGPPEGSSSGEM

SHDAEMRAAPGGNAVEAGQGADGVGNASGDWHCDSTWSEGRVTTTSTRTW

VLPTYNNHLYLRIGTTANSNTYNGFSTPWGCFDFNRFHCHFSPRDWQRLI

NNNWGLRPKSMRVKIFNIQVKEVTTSNGETTVANNLTSTVQIFADSTYEL

PYVMDAGQEGSLPPFPNDVFMVPQYGYCGVVTGENQNQTDRNAFYCLEYF

PSQMLRTGNNFEISYQFEKVPFHSMYAHSQSLDRMMNPLLDQYLWHLQST

TTGNSLNQGAATTTYGKITTGDFAYYRKNWLPGACIKQQKFSKNASQNYK

IPASGGDALLKYDTHTTLNGRWSNMAPGPPMATAGAGDSDFSNSQLIFAG

PNQSGNTTTSSNNLLFTSEEEIATTNPRDTDMFGQIADNNQNATTAPHIA

NLDAMGIVPGMVWQNRDIYYQGPIWAKVPHTDGHFHPSPLMGGFGLKHPP

PQIFIKNTPVPANPNTTFSAARINSFLTQYSTGQVAVQIDWEIQKEHSKR

WNPEVQFTSNYGTQNSMLWAPDNAGNYHEPRAIGSRFLTHHL

The VP1 sequence of a novel AAV capsid isolated from baboon (denoted as Bba.47) is set out as SEQ ID NO:3 (amino acids 1-742) and the locations of the associated variable regions and GBS region are defined in Table 2 below. The VP2 capsid protein spans amino acids 138-742 of SEQ ID NO:3 and the VP3 capsid protein spans amino acids 206-742 of SEQ ID NO:3.

MAADGYLPDWLEDNLSEGIREWWALKPGAPQPKANQQHQDNARGLVLPGY

KYLGPGNGLDKGEPVNEADAAALEHDKAYDQQLKSGDNPYLKYNHADAEF

QQRLATDTSFGGNLGKAVFQAKKRILEPLGLVEEGVKTAPGKKRPLEKTP

NRPTNPDSGKAPAKKKQKDGETADSARRTLDFEDSGAGDGPPEGSSSGEM

SHDAEMRAAPGGNAVEAGQGADGVGNASGDWHCDSTWSEGRVTTTSTRTW

VLPTYNNHLYLRIGTTANSNTYNGFSTPWGYFDFNRFHCHFSPRDWQRLI

```
NNNWGLRPKSMRVKIFNIQVKEVTTSNGETTVANNLTSTVQIFADSTYEL

PYVMDAGQEGSLPPFPNDVFMVPQYGYCGVVTGENQNQTDRNAFYCLEYF

PSQMLRTGNNFEISYQFEKVPFHSMYAHSQSLDRMMNPLLDQYLWHLQST

TTGNSLNQGTATTTYGKITTGDFAYYRKNWLPGACIKQQKFSKNASQNYK

IPASGGDALLKYDTHTTLNGRWSNMAPGPPMATAGAGDSDFSNSQLIFAG

PNQSGNTTTSSNNLLFTSEEEIATTNPRDTDMFGQIADNNQNATTAPHIA

NLDAMGIVPGMVWQNRDIYYQGPIWAKVPHTDGHFHPSPLMGGFGLKHPP

PQIFIKNTPVPANPNTTFSAARINSFLTQYSTGQVAVQIDWEIQKEHSKR

WNPEVQFTSNYGTQNSMLWAPDNAGNYHEPRAIGSRFLTHHL
```

The VP1 sequence of a novel AAV capsid isolated from baboon (denoted as Bba.48) is set out as SEQ ID NO:4 (amino acids 1-742) and the locations of the associated variable regions and GBS region are defined in Table 2 below. The VP2 capsid protein spans amino acids 138-742 of SEQ ID NO:4 and the VP3 capsid protein spans amino acids 206-742 of SEQ ID NO:4.

```
MAADGYLPDWLEDNLSEGIREWWALKPGAPQPKANQQHQDNARGLVLPGY

KYLGPGNGLDKGEPVNEADAAALEHDKAYDQQLKSGDNPYLKYNHADAEF

QERLQEDTSFGGNLGRAVFQAKKRILEPLGLVEEGVKTAPGKKRPLEKTP

NRPTNPDSGKAPAKKKQKDGETADSARRTLDFEDSGAGDGPPEGSSSGEM

SHDAEMRAAPGGNAVEAGQGADGVGNASGDWHCDSTWSEGRVTTTSTRTW

VLPTYNNHLYLRIGTTANSNTYNGFSTPWGYFDFNRFHCRFSPRDWQRLI

NNNWGLRPKSMRVKIFNIQVKEVTTSNGETTVANNLTSTVQIFADSTYEL

PYVMDAGQEGSLPPFPNDVFMVPQYGYCGVVTGENQNQTDRNAFYCLEYF

PSQMLRTGNNFEISYQFEKVPFHSMYAHSQSLDRMMNPLLDQYLWHLQST

TTGNSLNQGTAITTYGKITTGDFAYYRKNWLPGACIKQQKFSKNASQNYK

IPASGGDALLKYDTHTTLNGRWSNMAPGPPMATAGAGDSDFSNSQLIFAG

PNQSGNTTTSSNNLLFTSEEEIATTNPRDTDMFGQIADNNQNAATAPHIA

NLDAMGIVPGMVWQNRDIYYQGPIWAKVPHTDGHFHPSPLMGGFGLKHPP

PQIFIKNTPVPANPNTTFSAARINSFLTQYSTGQVAVQIDWEIQKEHSKR

WNPEVQFTSNYGTQNSMLWAPDNAGNYHEPRAIGSRFLTHHL
```

The VP1 sequence of a novel AAV capsid isolated from baboon (denoted as Bba.49) is set out as SEQ ID NO:5 (amino acids 1-742) and the locations of the associated variable regions and GBS region are defined in Table 2 below. The VP2 capsid protein spans amino acids 138-742 of SEQ ID NO:5 and the VP3 capsid protein spans amino acids 206-742 of SEQ ID NO:5.

```
MAADGYLPDWLEDNLSEGIREWWALKPGAPQPKANQQHQDNARGLVLPGY

KYLGPGNGLDKGEPVNEADAAALEHDKAYDQQLKSGDNPYLKYNHADAEF

QERLQEDTSFGGNLGRAVFQAKKRILEPLGLVEEGVKTAPGKKRPLEKTP

NRPTNPDSGKAPAKKKQKDGETADSARRTLDFEDSGAGDGPPEGSSSGEM

SHDAEMRAAPGGNAVEAGQGADGVGNASGDWHCDSTWSEGRVTTTSTRTW

VLPTYNNHLYLRIGTTANSNTYNGFSTPWGYFDFNRFHCHFSPRDWQRLI

NNNWGLRPKSMRVKIFNIQVKEVTTSNGETTVANNLTSTVQIFADSTYEL

PYVMDAGQEGSLPPFPNDVFMVPQYGYCGVVTGENQNQTDRNAFYCLEYF

PSQMLRTGNNFEISYQFEKVPFHSMYAHSQSLDRMMNPLLDQYLWHLQST

TTGNSLNQGTAITTYGKITTGDFAYYRKNWLPGAGIKQQKFSKNASQNYK

IPASGGDALLKYDTHTTLNGRWSNMAPGPPMATAGAGDSDFSNSQLIFAG

PNQSGNTTTSSNNLLFTSEEEIATTNPRDTDMFGQIADNNQNATTAPHIA

NLDAMGIVPGMVWQNRDIYYQGPIWAKVPHTDGHFHPSPLMGGFGLKHPP

PQIFIKNTPVPANPNTTFSAARINSFLTQYSTGQVAVQIDWEIQKEHSKR

WNPEVQFTSNYGTQNSMLWAPDNAGNYHEPRAIGSRFLTHHL
```

The VP1 sequence of a novel AAV capsid isolated from baboon (denoted as Bba.50) is set out as SEQ ID NO:6 (amino acids 1-742) and the locations of the associated variable regions and GBS region are defined in Table 2 below. The VP2 capsid protein spans amino acids 138-742 of SEQ ID NO:6 and the VP3 capsid protein spans amino acids 206-742 of SEQ ID NO:6.

```
MAADGYLPDWLEDNLSESIREWWALKPGAPRPKANQQHQDDARGLVLPGY

KYLGPGNGLDKGEPVNEADAAALEHDKAYDQQLKSGDNPYLKYNHADAEF

QQRLATDTSFGGNLGKAVFQAKKRILEPLGLVEEGVKTAPGRKRPLEKTP

NRPTNPDSGKAPAKKKQKDGETADSARRTLDFEDSGAGDGPPEGSSSGEM

SHDAEMRAAPGGNAVEAGQGADGVGNASGDWHCDSTWSEGRVTTTSTRTW

VLPTYNNHLYLRIGTTANSNTYNGFSTPWGYFDFNRFHCHFSPRDWQRLI

NNNWGLRPKSMRVKIFNIQVKEVTTSNGETTVANNLTSTVQIFADSTYEL

PYVMDAGQEGSLPPFPNDVFMVPQYGYCGVVTGENQNQTDRNAFYCLEYF

PSQMLRTGNNFEISYQFEKVPLHSMYAHSQSLDRMMNPLLDQYLWHLQST

TTGNSLNQGTATTTYGKITTGDFAYYRKNWLPGACIKQQKFSKNASQNYK

IPASGEDALLKYDTHTTLNGRWSNMAPGPPMATAGAGDSDFSNSQLIFAG

PNQSGNTTTSSNNLLFTSEEEIATTNPRDTDMFGQIADNNQNATTAPHIA

NLDAMGIVPGMVWQNRDIYYQGPIWAKVPHTDGHFHPSPLMGGFGLKHPP

PQIFIKNTPVPANPNTTFSAARINSFLTQYSTGQVAVQIDWEIQKEHSKR

WNPEVQFTSNYGTQNSMLWAPDNAGNYHEPRAIGSRFLTHHL
```

The VP1 sequence of a novel AAV capsid isolated from baboon (denoted as Bba.51) is set out as SEQ ID NO:7 (amino acids 1-742) and the locations of the associated variable regions and GBS region are defined in Table 2 below. The VP2 capsid protein spans amino acids 138-742 of SEQ ID NO:7 and the VP3 capsid protein spans amino acids 206-742 of SEQ ID NO:7.

```
MAADGYLPDWLEDNLSEGIREWWALKPGAPQPKANQQHQDNARGLVLPGY

KYLGPGNGLDKGEPVNEADAAALEHDKAYDQQLKSGDNPYLKYNHADAEF

QQRLATDTSFGGNLGKAVFQAKKRILEPLGLVEEGVKTAPGKKRPLEKTP

NRPTNPDSGKAPAKKKQKDGETADSARRTLDFEDSGAGDGPPEGSSSGEM

SHDAEMRAAPGGNAVEAGQGADGVGNASGDWHCDSTWSEGRVTTTSTRTW
```

-continued

VLPTYNNHLYLRIGTTANSNTYNGFSTPWGYFDFNRFHCHFSPRDWQRLI
NNNWGLRPKSMRVKIFNIQVKEVTTSNGETTVANNLTSTVQIFADSTYEL
PYVMDAGQEGSLPPFPNDVFMVPQYGYCGVVTGENQNQTDRNAFYCLEYF
PSQMLRTGNNFEISYQFEKVPFHSMYAHSQSLDRMMNPLLDQYLWHLQST
TTGNSLNQGTATTTYGKITTGDFAYYRKNWLPGACIKQQKFSKNASQNYK
IPASGGDALLKYDTHTTLNGRWSNMAPGPPMATAGAGDSDFSNSQLIFAG
PNQSGNTTTSSNNLLFTSEEEIATTNPRDTDMFGQIADNNQNATTAPHIA
NLDAMGIVPGMVWQNRDIYYQGPIWAKVPHTDGHFHPSPLMGGFGLKHPP
PQIFIKNTPVPANPNTTFSAARINSFLTQYSTGQVAVQIDWEIQKEHSKR
WNPEVQFTSNYGTQNSMLWAPDNAGNYHEPRAIGSRFLTHHL

The corresponding nucleic acid sequences encoding the above referenced capsid proteins are SEQ ID NO:8/Bba.45; SEQ ID NO:9/Bba.46; SEQ ID NO:10/Bba.47; SEQ ID NO:11/Bba.48; SEQ ID NO:12/Bba.49; SEQ ID NO:13/Bba.50; and SEQ ID NO:14/Bba.51.

(Bba.45)
SEQ ID NO: 8
ATGGCTGCTGACGGTTATCTTCCAGATTGGCTCGAGGACAACCTCTCTGA
AGGCATTCGCGAGTGGTGGGCGCTGAAACCTGGAGCCCCACAGCCCAAGG
CAAATCGACAACATCAAGACAACGCTCGGGGTCTTGTGCTTCCGGGTTAC
AAATACTTGGGACCCGGTAACGGACTCGACAAGGGAGAGCCGGTCAACGA
GGCAGACGCCGCGCCCTCGAGCACGACAAGGCCTACGACCAGCAGCTCA
AGTCGGGAGACAACCCGTACCTCAAGTACAACCACGCGGACGCCGAGTTC
CAGCAGCGCTTGGCGACCGACACCTCTTTTGGGGGCAACCTCGGCAAGGC
AGTCTTCCAGGCCAAAAAGAGGATTCTCGAGCCTCTGGGTCTGGTTGAAG
AGGGCGTTAAAACGGCTCCTGGAAAGAAACGCCCATTAGAAAAGACTCCA
AATCGGCCGACCAACCCGGACTCTGGGAAGGCCCCGGCCAAGAAAAAGCA
AAAAGACGGCGAGACAGCCGACTCTGCTAGAAGGGCACTCGACTTTGAAG
ACTCTGGAGCAGGAGACGGACCCCCTGAGGGATCATCTTCCGGAGAAATG
TCTCATGATGCTGAGATGCGTGCGGCGCCAGGCGGAAATGCTGTCGAGGC
GGGACAAGGTGCCGATGGAGTGGGTAATGCCTCCGGTGATTGGCATTGCG
ATTCCACCTGGTCAGAGGGCCGAGTCACCACCACCAGCACCCGAACCTGG
GTCCTGCCCACCTACAACAACCACCTGTACCTGCGAATCGGAACAACGGC
CAACAGCAACACCTACAATGGATTCTCCACCCCCTGGGGATACTTTGACT
TTAACCGCTTCCACTGCCACTTTTCCCCACGCGACTGGCAGCGACTCATC
AACAACAACTGGGGACTCAGGCCGAAATCGATGCGTGTTAAAATCTTCAA
CATCCAGGTCAGGGAGGTCACTACGTCAAACGGCGAGACTACGGTCGCTA
ATAACCTTACCAGCACGGTTCAGATCTTTGCGGATTCAACGTATGAACTC
CCATACGTGATGGACGCCGGTCAGGAGGGGAGCCTTCCTCCGTTCCCCAA
CGACGTGTTTATGGTTCCCCAATACGGGTACTGCGGAGTCGTCACTGGAG
AAAACCAGAACCAAACAGACAGAAATGCCTTTTACTGTCTGGAGTACTTT
CCATCCCAAATGCTAAGAACTGGCAACAACTTTGAAATCAGTTACCAATT

TGAAAAAGTTCCTTTCCATTCAATGTACGCGCACAGCCAGAGCCTGGACA
GAATGATGAATCCTTTGCTGGATCAGTACCTGTGGCATCTGCAATCGACC
ACTACCGGAAATTCCCTTAATCAAGGAACAGCTACCACCACGTACGGGAA
AATTACCACTGGGGACTTTGCCTACTACAGGAAAAACTGGTTACCTGGAG
CCTGCATTAAACAACAAAAATTTTCAAAGAATGCCAGTCAAAACTACAAG
ATTCCCGCCAGCGGGGAGACGCCCTTTTAAAGTATGACACGCATACCAC
TTTAAATGGGCGATGGAGTAACATGGCTCCTGGTCCTCCAATGGCCACCG
CAGGTGCCGGGGACTCGGATTTTAGCAACAGCCAGCTGATCTTTGCCGGA
CCCAATCAGAGCGGTAACACGACCACGTCTTCAAACAATTTGTTGTTTAC
CTCAGAAGAGGAGATTGCCACAACAAACCCACGAGACACGGACATGTTTG
GACAGATTGCAGATAATAATCAAATGCCACCACCGCCCCTCACATCGCT
AACCTGGACGCTATGGGAATTGTTCCCGGAATGGTCTGGCAAAACAGAGA
CATCTACTACCAGGGCCCTATTTGGGCCAAGGTCCCTCACACGGACGGAC
ACTTTCACCCTTCGCCGCTGATGGGAGGATTTGGACTGAAACACCCGCCT
CCGCAGATTTTCATCAAAAACACCCCCGTACCCGCCAATCCCAATACTAC
CTTTAGCGCTGCAAGGATCAATTCTTTTTTGACGCAGTACAGCACCGGAC
AAGTCGCCGTTCAGATCGACTGGGAAATTCAGAAGGAGCACTCCAAACGC
TGGAATCCCGAAGTCCAATTTACTTCAAACTACGGCACTCAAAATTCTAT
GCTGTGGGCTCCCGACAACGCCGGCAACTACCACGAACCCCGGGCTATTG
GGTCCCGTTTCCTCACCCACCACTTGTAA (Bba.46)
SEQ ID NO: 9
ATGGCTGCTGACGGTTATCTTCCAGATTGGCTCGAGGACAACCTCTCTGA
AGGCATTCGCGAGTGGTGGGCGCTGAAACCTGGAGCCCCACAGCCCAAGG
CAAATCAACAACATCAAGACAACGCTCGGGGTCTTGTGCTTCCGGGTTAC
AAATACTTGGGACCCGGTAACGGACTCGACAAGGGAGAGCCGGTCAACGA
GGCAGACGCCGCGGCCCTCGAGCACGACAAGGCCTACGACCAGCAGCTCA
AGTCGGGAGACAACCCGTACCTCAAGTACAACCACGCGGACGCCGAGTTC
CAGCAGCGCTTGGCGACCGACACCTCTTTTGGGGGCAACCTCGGCAAGGC
AGTCTTCCAGGCCAAAAAGAGGATTCTCGAGCCTCTGGGTCTGGTTGAAG
AGGGCGTTAAAACGGCTCCTGGAAAGAAACGCCCATTAGAAAAGACTCCA
AATCGGCCGACCAACCCGGACTCTGGGAAGGCCCCGGCCAAGAAAAAGCA
AAAAGACGGCGAGACAGCCGACTCTGCTAGAAGGACACTCGACTTTGAAG
ACTCTGGAGCAGGAGACGGACCCCCTGAGGGATCATCTTCCGGAGAAATG
TCTCATGACGCTGAGATGCGTGCGGCGCCAGGCGGAAATGCTGTCGAGGC
GGGACAAGGTGCCGATGGAGTGGGTAATGCCTCCGGTGATTGGCATTGCG
ATTCCACCTGGTCAGAGGGCCGAGTCACCACCACCAGCACCCGAACCTGG
GTCCTGCCCACCTACAACAACCACCTGTACCTGCGAATCGGAACAACGGC
CAACAGCAACACCTACAATGGATTCTCCACCCCCTGGGGATGCTTTGACT
TTAACCGCTTCCACTGCCACTTTTCCCCACGCGACTGGCAGCGACTCATC
AACAACAACTGGGGACTCAGGCCGAAATCGATGCGTGTTAAAATCTTCAA
CATCCAGGTCAAGGAGGTCACTACGTCAAACGGCGAGACTACGGTCGCTA

ATAACCTTACCAGCACGGTTCAGATCTTTGCGGATTCAACGTATGAACTC
CCATACGTGATGGACGCCGGTCAGGAGGGGAGCCTTCCTCCGTTCCCCAA
CGACGTGTTTATGGTTCCCCAATACGGGTACTGCGGAGTCGTCACTGGAG
AAAACCAGAACCAAACAGACAGAAATGCCTTTTACTGTCTGGAGTACTTT
CCATCCCAAATGCTAAGAACTGGCAACAACTTTGAAATCAGTTACCAATT
TGAAAAAGTTCCTTTCCATTCAATGTACGCGCACAGCCAGAGCCTGGACA
GAATGATGAATCCTTTGCTGGATCAGTACCTGTGGCATCTGCAATCGACC
ACTACCGGAAATTCCCTTAATCAAGGAGCAGCTACCACCACGTACGGGAA
AATTACCACTGGGGACTTTGCCTACTACAGGAAAAACTGGTTGCCTGGAG
CCTGCATTAAACAACAAAAATTTTCAAAGAATGCCAGTCAAAACTACAAG
ATCCCCGCCAGCGGGGAGACGCCCTTTTAAAGTATGACACGCATACCAC
TTTAAATGGGCGATGGAGTAACATGGCTCCTGGTCCTCCAATGGCCACCG
CAGGTGCCGGGGACTCGGATTTTAGCAACAGCCAGCTGATCTTTGCCGGA
CCCAATCAGAGCGGTAACACGACCACGTCTTCAAACAATTTGTTGTTTAC
CTCAGAAGAGGAGATTGCCACAACAAACCCACGAGACACGGACATGTTTG
GACAGATTGCAGATAATAATCAAAATGCCACCACCGCCCCTCACATCGCT
AACCTGGACGCTATGGGAATTGTTCCCGGAATGGTCTGGCAAAACAGAGA
CATCTACTACCAGGGCCCTATTTGGGCCAAGGTCCCTCACACGGACGGAC
ACTTTCACCCTTCGCCGCTGATGGGAGGATTTGGACTGAAACACCCGCCT
CCGCAGATTTTCATCAAAAACACCCCCGTACCCGCCAATCCCAATACTAC
CTTTAGCGCTGCAAGGATCAATTCTTTTTTGACGCAGTACAGCACCGGAC
AAGTCGCCGTTCAGATCGACTGGGAAATTCAGAAGGAGCACTCCAAACGC
TGGAATCCCGAAGTCCAATTTACTTCAAACTACGGCACTCAAAATTCTAT
GCTGTGGGCTCCCGACAACGCCGGCAACTACCACGAACCCCGGGCTATTG
GGTCCCGTTTCCTCACCCACCACTTGTAA (Bba.47)
SEQ ID NO: 10
ATGGCTGCTGACGGTTATCTTCCAGATTGGCTCGAGGACAACCTCTCTGA
AGGCATTCGCGAGTGGTGGGCGCTGAAACCTGGAGCCCCACAGCCCAAGG
CAAATCAACAACATCAAGACAACGCTCGGGGTCTTGTGCTTCCGGGTTAC
AAATACTTGGGACCCGGTAACGGACTCGACAAGGGAGAGCCGGTCAACGA
GGCAGACGCCGCGGCCCTCGAGCACGACAAGGCCTACGACCAGCAGCTCA
AGTCGGGAGACAACCCGTACCTCAAGTACAACCACGCGGACGCCGAGTTC
CAGCAGCGCTTGGCGACCGACACCTCTTTTGGGGGCAACCTCGGCAAGGC
AGTCTTCCAGGCCAAAAAGAGGATTCTCGAGCCTCTGGGTCTGGTTGAAG
AGGGCGTTAAAACGGCTCCTGGAAAGAAACGCCCATTAGAAAAGACTCCA
AATCGGCCGACCAACCCGGACTCTGGGAAGGCCCCGGCCAAGAAAAAGCA
AAAAGACGGCGAGACAGCCGACTCTGCTAGAAGGACACTCGACTTTGAAG
ACTCTGGAGCAGGAGACGGACCTCCTGAGGGATCATCTTCCGGAGAAATG
TCTCATGATGCTGAGATGCGTGCGGCGCCAGGCGGAAATGCTGTCGAGGC
GGGACAAGGTGCCGATGGAGTGGGTAATGCCTCCGGTGATTGGCATTGCG

ATTCCACCTGGTCAGAGGGCCGAGTCACCACCACCAGCACCCGAACCTGG
GTCCTGCCCACCTACAACAACCACCTGTACCTGCGAATCGGAACAACGGC
CAACAGCAACACCTACAATGGATTCTCCACCCCCTGGGGATACTTTGACT
TTAACCGCTTCCACTGCCACTTTTCCCCACGCGACTGGCAGCGACTCATC
AACAACAACTGGGGACTCAGGCCGAAATCGATGCGTGTTAAAATCTTCAA
CATCCAGGTCAAGGAGGTCACTACGTCAAACGGCGAGACTACGGTCGCTA
ATAACCTTACCAGCACGGTTCAGATCTTTGCGGATTCAACGTATGAACTC
CCATACGTGATGGACGCCGGTCAGGAGGGGAGCCTTCCTCCGTTCCCCAA
CGACGTGTTTATGGTTCCCCAATACGGGTACTGCGGAGTCGTCACTGGAG
AAAACCAGAACCAAACAGACAGAAATGCCTTTTACTGTCTGGAGTACTTT
CCATCCCAAATGCTAAGAACTGGCAACAACTTTGAAATCAGTTACCAATT
TGAAAAAGTTCCTTTCCATTCAATGTACGCGCACAGCCAGAGCCTGGACA
GAATGATGAATCCTTTGCTGGATCAGTACCTGTGGCATCTGCAATCGACC
ACTACCGGAAATTCCCTTAATCAAGGAACAGCTACCACCACGTACGGGAA
AATTACCACTGGGGACTTTGCCTACTACAGGAAAAACTGGTTGCCTGGAG
CCTGCATTAAACAACAAAAATTTTCAAAGAATGCCAGTCAAAACTACAAG
ATTCCCGCCAGCGGGGAGACGCCCTTTTAAAGTATGACACGCATACCAC
TTTAAATGGGCGATGGAGTAACATGGCTCCTGGTCCTCCAATGGCCACCG
CAGGTGCCGGGGACTCGGATTTTAGCAACAGCCAGCTGATCTTTGCCGGA
CCCAATCAGAGCGGTAACACGACCACGTCTTCAAACAATTTGTTGTTTAC
CTCAGAAGAGGAGATTGCCACAACAAACCCACGAGACACGGACATGTTTG
GGCAGATTGCAGATAATAATCAAAATGCCACCACCGCCCCTCACATCGCT
AACCTGGACGCTATGGGAATTGTTCCCGGAATGGTCTGGCAAAACAGAGA
CATCTACTACCAGGGCCCTATTTGGGCCAAGGTCCCTCACACGGACGGAC
ACTTTCACCCTTCGCCGCTGATGGGAGGATTTGGACTGAAACACCCGCCT
CCGCAGATTTTCATCAAAAACACCCCCGTACCCGCCAATCCCAATACTAC
CTTTAGCGCTGCAAGGATCAATTCTTTTTTGACGCAGTACAGCACCGGAC
AAGTCGCCGTTCAGATCGACTGGGAAATTCAGAAGGAGCACTCCAAACGC
TGGAATCCCGAAGTCCAATTTACTTCAAACTACGGCACTCAAAATTCTAT
GCTGTGGCTCCCGACAACGCCGGCAACTACCACGAACCCCGGGCTATTG
GGTCCCGTTTCCTCACCCACCACTTGTAA (Bba.48)
SEQ ID NO: 11
ATGGCTGCTGACGGTTATCTTCCAGATTGGCTCGAGGACAACCTCTCTGA
AGGCATTCGCGAGTGGTGGGCGCTGAAACCTGGAGCCCCACAGCCCAAGG
CAAATCAACAACATCAAGACAACGCTCGGGGTCTTGTGCTTCCGGGTTAC
AAATACTTGGGACCCGGTAACGGACTCGACAAGGGAGAGCCGGTCAACGA
GGCAGACGCCGCGGCCCTCGAGCACGACAAGGCCTACGACCAGCAGCTCA
AGTCGGGAGACAACCCGTACCTCAAGTACAACCACGCGGACGCCGAGTTT
CAGGAGCGTCTTCAAGAAGATACGTCTTTTGGGGGCAACCTCGGGCGAGC
AGTCTTCCAGGCCAAAAAGAGGATTCTCGAGCCTCTGGGTCTGGTTGAAG
AGGGCGTTAAAACGGCTCCTGGAAAGAAACGCCCATTAGAAAAGACTCCA

-continued

AATCGGCCGACCAACCCGGACTCTGGGAAGGCCCCGGCCAAGAAAAAGCA

AAAAGACGGCGAGACAGCCGACTCTGCTAGAAGGACACTCGACTTTGAAG

ACTCTGGAGCAGGAGACGGACCCCCTGAGGGATCATCTTCCGGAGAAATG

TCTCATGATGCTGAGATGCGTGCGGCGCCAGGCGGAAATGCTGTCGAGGC

GGGACAAGGTGCCGATGGAGTGGGTAATGCCTCCGGTGATTGGCATTGCG

ATTCCACCTGGTCAGAGGGCCGAGTCACCACCACCAGCACCCGAACCTGG

GTCCTGCCCACCTACAACAACCACCTGTACCTGCGAATCGGAACAACGGC

CAACAGCAACACCTACAATGGATTCTCCACCCCCTGGGGATACTTTGACT

TTAACCGCTTCCACTGCCGCTTTTCCCCGCGCGACTGGCAGCGACTCATC

AACAACAACTGGGGACTCAGGCCGAAATCGATGCGTGTTAAAATCTTCAA

CATCCAGGTCAAGGAGGTCACTACGTCAAACGGCGAGACTACGGTCGCTA

ATAACCTTACCAGCACGGTTCAGATCTTTGCGGATTCAACGTATGAACTC

CCATACGTGATGGACGCCGGTCAGGAGGGGAGCCTTCCTCCGTTCCCCAA

CGACGTGTTTATGGTTCCCCAATACGGGTACTGCGGAGTCGTCACTGGAG

AAAACCAGAACCAAACAGACAGAAATGCCTTTTACTGTCTGGAGTACTTT

CCATCCCAAATGCTAAGAACTGGCAACAACTTTGAAATCAGTTACCAATT

TGAAAAAGTTCCTTTCCATTCAATGTACGCGCACAGCCAGAGCCTGGACA

GAATGATGAATCCTTTGCTGGATCAGTACCTGTGGCATCTGCAATCGACC

ACTACCGGAAATTCCCTTAATCAAGGAACAGCTATCACCACGTACGGGAA

AATTACCACTGGGGACTTTGCCTACTACAGGAAAAACTGGTTGCCTGGAG

CCTGCATTAAACAACAAAAATTTTCAAAGAATGCCAGTCAAAACTACAAG

ATTCCCGCCAGCGGGGAGACGCCCTTTTAAAGTATGACACGCATACCAC

TTTAAATGGGCGATGGAGTAACATGGCTCCTGGTCCTCCAATGGCCACCG

CAGGTGCCGGGACTCGGATTTTAGCAACAGCCAGCTGATCTTTGCCGGA

CCCAATCAGAGCGGTAACACGACCACGTCTTCAAACAATTTGTTGTTTAC

CTCAGAAGAGGAGATTGCCACAACAAACCCACGAGACACGGACATGTTTG

GACAGATTGCAGATAATAATCAAAATGCCGCCACCGCCCCTCACATCGCT

AACCTGGACGCTATGGGAATTGTTCCCGGAATGGTCTGGCAAAACAGAGA

CATCTACTACCAGGGCCCTATTTGGGCCAAGGTCCCTCACACGGACGGAC

ACTTTCACCCTTCGCCGCTGATGGGAGGATTTGGACTGAAACACCCGCCT

CCGCAGATTTTCATCAAAAACACCCCCGTACCCGCCAATCCCAATACTAC

CTTTAGCGCTGCAAGGATCAATTCTTTTTTGACGCAGTACAGCACCGGAC

AAGTCGCCGTTCAGATCGACTGGGAAATTCAGAAGGAGCACTCCAAACGC

TGGAATCCCGAAGTCCAATTTACTTCAAACTACGGCACTCAAAATTCTAT

GCTGTGGGCTCCCGACAACGCCGGCAACTACCACGAACCCCGGGCTATTG

GGTCCCGTTTCCTCACCCACCACTTGTAA (Bba.49)
SEQ ID NO: 12
ATGGCTGCTGACGGTTATCTTCCAGATTGGCTCGAGGACAACCTCTCTGA

AGGCATTCGCGAGTGGTGGGCGCTGAAACCTGGAGCCCCACAGCCCAAGG

CAAATCAACAACATCAAGACAACGCTCGGGGTCTTGTGCTTCCGGGTTAC

-continued

AAATACTTGGGACCCGGTAACGGACTCGACAAGGGAGAGCCGGTCAACGA

GGCAGACGCCGCGGCCCTCGAGCACGACAAGGCCTACGACCAGCAGCTCA

AGTCGGGAGACAACCCGTACCTCAAGTACAACCACGCGGACGCCGAGTTT

CAGGAGCGTCTTCAAGAAGATACGTCTTTTGGGGGCAACCTCGGGCGAGC

AGTCTTCCAGGCCAAAAAGAGGATTCTCGAGCCTCTGGGTCTGGTTGAAG

AGGGGCGTTAAAACGGCTCCTGGAAAGAAACGCCCATTAGAAAAGACTCCA

AATCGGCCGACCAACCCGGACTCTGGGAAGGCCCCGGCCAAGAAAAAGCA

AAAAGACGGCGAGACAGCCGACTCTGCTAGAAGGACACTCGACTTTGAAG

ACTCTGGAGCAGGAGACGGACCCCCTGAGGGATCATCTTCCGGAGAAATG

TCTCATGATGCTGAGATGCGTGCGGCGCCAGGCGGAAATGCTGTCGAGGC

GGGACAAGGTGCCGATGGAGTGGGTAATGCCTCCGGTGATTGGCATTGCG

ATTCCACCTGGTCAGAGGGCCGAGTCACCACCACCAGCACCCGAACCTGG

GTCCTGCCCACCTACAACAACCACCTGTACCTGCGAATCGGAACAACGGC

CAACAGCAACACCTACAATGGATTCTCCACCCCCTGGGGATACTTTGACT

TTAACCGCTTCCACTGCCACTTTTCCCCACGCGACTGGCAGCGACTCATC

AACAACAACTGGGGACTCAGGCCGAAATCGATGCGTGTTAAAATCTTCAA

CATCCAGGTCAAGGAGGTCACTACGTCAAACGGCGAGACTACGGTCGCTA

ATAACCTTACCAGCACGGTTCAGATCTTTGCGGATTCAACGTATGAACTC

CCATACGTGATGGACGCCGGTCAGGAGGGGAGCCTTCCTCCGTTCCCCAA

CGACGTGTTTATGGTTCCCCAATACGGGTACTGCGGAGTCGTCACTGGAG

AAAACCAGAACCAAACAGACAGAAATGCCTTTTACTGTCTGGAGTACTTT

CCATCCCAAATGCTAAGAACTGGCAACAACTTTGAAATCAGTTACCAATT

TGAAAAAGTTCCTTTCCATTCAATGTACGCGCACAGCCAGAGCCTGGACA

GAATGATGAATCCTTTGCTGGATCAGTACCTGTGGCATCTGCAATCGACC

ACTACCGGAAATTCCCTTAATCAAGGAACAGCTATCACCACGTACGGGAA

AATTACCACTGGGGACTTTGCCTACTACAGGAAAAACTGGTTGCCTGGAG

CCGGCATTAAACAACAAAAATTTTCAAAGAATGCCAGTCAAAACTACAAG

ATTCCCGCCAGCGGGGAGACGCCCTTTTAAAGTATGACACGCATACCAC

TTTAAATGGGCGATGGAGTAACATGGCTCCTGGTCCTCCAATGGCCACCG

CAGGTGCCGGGACTCGGATTTTAGCAACAGCCAGCTGATCTTTGCCGGA

CCCAATCAGAGCGGTAACACGACCACGTCTTCAAACAATTTGTTGTTTAC

CTCAGAAGAGGAGATTGCCACAACAAACCCACGAGACACGGACATGTTTG

GACAGATTGCAGATAATAATCAAAATGCCACCACCGCCCCTCACATCGCT

AACCTGGACGCTATGGGAATTGTTCCCGGAATGGTCTGGCAAAACAGAGA

CATCTACTACCAGGGCCCTATTTGGGCCAAGGTCCCTCACACGGACGGAC

ACTTTCACCCTTCGCCGCTGATGGGAGGATTTGGACTGAAACACCCGCCT

CCGCAGATTTTCATCAAAAACACCCCCGTACCCGCCAATCCCAATACTAC

CTTTAGCGCTGCAAGGATCAATTCTTTTTTGACGCAGTACAGCACCGGAC

AAGTCGCCGTTCAGATCGACTGGGAAATTCAGAAGGAGCACTCCAAACGC

TGGAATCCCGAAGTCCAATTTACTTCAAACTACGGCACTCAAAATTCTAT (Bba.50)

SEQ ID NO: 13
ATGGCTGCTGACGGTTATCTTCCAGATTGGCTCGAGGACAACCTCTCTGA
AAGCATTCGCGAGTGGTGGGCGCTGAAACCTGGAGCCCCACGGCCCAAGG
CAAATCAACAACATCAAGACGACGCTCGGGGTCTTGTGCTTCCGGGTTAC
AAATACTTGGGACCCGGTAACGGACTCGACAAGGGAGAGCCGGTCAACGA
GGCAGACGCCGCGGCCCTCGAGCACGACAAGGCCTACGACCAGCAGCTCA
AGTCGGGAGACAACCCGTACCTCAAGTACAACCACGCGGACGCCGAGTTC
CAGCAGCGCTTGGCGACCGACACCTCTTTTGGGGGCAACCTCGGCAAGGC
AGTCTTCCAGGCCAAAAAGAGGATTCTCGAGCCTCTGGGTCTGGTTGAAG
AGGGCGTTAAAACGGCTCCTGGAAGGAAACGCCCATTAGAAAAGACTCCA
AATCGGCCGACCAACCCGGACTCTGGGAAGGCCCCGGCCAAGAAAAAGCA
AAAAGACGGCGAGACAGCCGACTCTGCTAGAAGGACACTCGACTTTGAAG
ACTCTGGAGCAGGAGACGGACCCCCTGAGGGATCATCTTCCGGAGAAATG
TCTCATGATGCTGAGATGCGTGCGGCGCCAGGCGGAAATGCTGTCGAGGC
GGGACAAGGTGCCGATGGAGTGGGTAATGCCTCCGGTGATTGGCATTGCG
ATTCCACCTGGTCAGAGGGCCGAGTCACCACCACCAGCACCCGAACCTGG
GTCCTGCCCACCTACAACAACCACCTGTACCTGCGAATCGGAACAACGGC
CAACAGCAACACCTACAATGGATTCTCCACCCCCTGGGGATACTTTGACT
TTAACCGCTTCCACTGCCACTTTTCCCCACGCGACTGGCAGCGACTCATC
AACAACAACTGGGGACTCAGGCCGAAATCGATGCGTGTTAAAATCTTCAA
CATCCAGGTCAAGGAGGTCACTACGTCAAACGGCGAGACTACGGTCGCTA
ATAACCTTACCAGCACGGTTCAGATCTTTGCGGATTCAACGTATGAACTC
CCATACGTGATGGACGCCGGTCAGGAGGGGAGCCTTCCTCCGTTCCCCAA
CGACGTGTTTATGGTTCCCCAATACGGGTACTGCGGAGTCGTCACTGGAG
AAAACCAGAACCAAACAGACAGAAATGCCTTTTACTGTCTGGAGTACTTT
CCATCCCAAATGCTAAGAACTGGCAACAACTTTGAAATCAGTTACCAATT
TGAAAAAGTTCCTCTCCATTCAATGTACGCGCACAGCCAGAGCCTGGACA
GAATGATGAATCCTTTGCTGGATCAGTACCTGTGGCATCTGCAATCGACC
ACTACCGGAAATTCCCTTAATCAAGGAACAGCTACCACCACGTACGGGAA
AATTACCACTGGGGACTTTGCCTACTACAGGAAAAACTGGTTGCCTGGAG
CCTGCATTAAACAACAAAAATTTTCAAAGAATGCCAGTCAAAACTACAAG
ATTCCCGCCAGCGGGGAAGACGCCCTTTTAAAGTATGACACGCATACCAC
TTTAAATGGGCGATGGAGTAACATGGCTCCTGGTCCTCCAATGGCCACCG
CAGGTGCCGGGGACTCGGATTTTAGCAACAGCCAGCTGATCTTTGCCGGA
CCCAATCAGAGCGGTAACACGACCACGTCTTCAAACAATTTGTTGTTTAC
CTCAGAAGAGGAGATTGCCACAACAAACCCACGAGACACGGACATGTTTG
GACAGATTGCAGATAATAATCAAAATGCCACCACCGCCCCTCACATCGCT
AACCTGGACGCTATGGGAATTGTTCCCGGAATGGTCTGGCAAAACAGAGA

CATCTACTACCAGGGCCCTATCTGGGCCAAGGTCCCTCACACGGACGGAC
ACTTTCACCCTTCGCCGCTGATGGGAGGATTTGGACTGAAACACCCGCCT
CCGCAGATTTTCATCAAAAACACCCCCGTACCCGCCAATCCCAATACTAC
CTTTAGCGCTGCAAGGATCAATTCTTTTTTGACGCAGTACAGCACCGGAC
AAGTCGCCGTTCAGATCGACTGGGAAATTCAGAAGGAGCACTCCAAACGC
TGGAATCCCGAAGTCCAATTTACTTCAAACTACGGCACTCAAAATTCTAT
GCTGTGGGCTCCCGACAACGCCGGCAACTACCACGAACCCCGGGCTATTG
GGTCCCGTTTCCTCACCCACCACTTGTAA (Bba.51)

SEQ ID NO: 14
ATGGCTGCTGACGGTTATCTTCCAGATTGGCTCGAGGACAACCTCTCTGA
AGGCATTCGCGAGTGGTGGGCGCTGAAACCTGGAGCCCCACAGCCCAAGG
CAAATCAACAACATCAAGACAACGCTCGGGGTCTTGTGCTTCCGGGTTAC
AAATACTTGGGACCCGGTAACGGACTCGACAAGGGAGAGCCGGTCAACGA
GGCAGACGCCGCGGCCCTCGAGCACGACAAGGCCTACGACCAGCAGCTCA
AGTCGGGAGACAACCCGTACCTCAAGTACAACCACGCGGACGCCGAGTTC
CAGCAGCGCTTGGCGACCGACACCTCTTTTGGGGGCAACCTCGGCAAGGC
AGTCTTCCAGGCCAAAAAGAGGATTCTCGAGCCTCTGGGTCTGGTTGAAG
AGGGCGTTAAAACGGCTCCTGGAAAGAAACGCCCATTAGAAAAGACTCCA
AATCGGCCGACCAACCCGGACTCTGGGAAGGCCCCGGCCAAGAAAAAGCA
AAAAGACGGCGAGACAGCCGACTCTGCTAGAAGGACACTCGACTTTGAAG
ACTCTGGAGCAGGAGACGGACCCCCTGAGGGATCATCTTCCGGAGAAATG
TCTCATGATGCTGAGATGCGTGCGGCGCCAGGCGGAAATGCTGTCGAGGC
GGGACAAGGTGCCGATGGAGTGGGTAATGCCTCCGGTGATTGGCATTGCG
ATTCCACCTGGTCAGAGGGCCGAGTCACCACCACCAGCACCCGAACCTGG
GTCCTGCCCACCTACAACAACCACCTGTACCTGCGAATCGGAACAACGGC
CAACAGCAACACCTACAATGGATTCTCCACCCCCTGGGGATACTTTGACT
TTAACCGCTTCCACTGCCACTTTTCCCCACGCGACTGGCAGCGACTCATC
AACAACAACTGGGGACTCAGGCCGAAATCGATGCGTGTTAAAATCTTCAA
CATCCAGGTCAAGGAGGTCACTACGTCAAACGGCGAGACTACGGTCGCTA
ATAACCTTACCAGCACGGTTCAGATCTTTGCGGATTCAACGTATGAACTC
CCATACGTGATGGACGCCGGTCAGGAGGGGAGCCTTCCTCCGTTCCCCAA
CGACGTGTTTATGGTTCCCCAATACGGGTACTGCGGAGTCGTCACTGGAG
AAAACCAGAACCAAACAGACAGAAATGCCTTTTACTGTCTGGAGTACTTT
CCATCCCAAATGCTAAGAACTGGCAACAACTTTGAAATCAGTTACCAATT
TGAAAAGTTCCTTTCCATTCAATGTACGCGCACAGCCAGAGCCTGGACA
GAATGATGAATCCTTTGCTGGATCAGTACCTGTGGCATCTGCAATCGACC
ACTACCGGAAATTCCCTTAATCAAGGAACAGCTACCACCACGTACGGGAA
AATTACCACTGGGGACTTTGCCTACTACAGGAAAAACTGGTTGCCTGGAG
CCTGCATTAAACAACAAAAATTTTCAAAGAATGCCAGTCAAAACTACAAG
ATTCCCGCCAGCGGGGAGACGCCCTTTTAAAGTATGACACGCATACCAC
TTTAAATGGGCGATGGAGTAACATGGCTCCTGGTCCTCCAATGGCCACCG

```
CAGGTGCCGGGGACTCGGATTTTAGCAACAGCCAGCTGATCTTTGCCGGA

CCCAATCAGAGCGGTAACACGACCACGTCTTCAAACAATTTGTTGTTTAC

CTCAGAAGAGGAGATTGCCACAACAAACCCACGAGACACGGACATGTTTG

GACAGATTGCAGATAATAATCAAAATGCCACCACCGCCCCTCACATCGCT

AACCTGGACGCTATGGGAATTGTTCCCGGAATGGTCTGGCAAAACAGAGA

CATCTACTACCAGGGCCCTATTTGGGCCAAGGTCCCTCACACGGACGGAC

ACTTTCACCCTTCGCCGCTGATGGGAGGATTTGGACTGAAACACCCGCCT

CCGCAGATTTTCATCAAAAACACCCCCGTACCCGCCAATCCCAATACTAC

CTTTAGCGCTGCAAGGATCAATTCTTTTTTGACGCAGTACAGCACCGGAC

AAGTCGCCGTTCAGATCGACTGGGAAATTCAGAAGGAGCACTCCAAACGC

TGGAATCCCGAAGTCCAATTTACTTCAAACTACGGCACTCAAAATTCTAT

GCTGTGGGCTCCCGACAACGCCGGCAACTACCACGAACCCCGGGCTATTG

GGTCCCGTTTCCTCACCCACCACTTGTAA
```

In Table 2 immediately below, "VR" refers to the variable region and the numbers refer to the amino acid residues in each variable region or in the GBS region for the amino acid sequences.

TABLE 2

| AAV | VRI | VRII | VRIII | VRIV | GBS | VRV | VRVI | VRVII |
|---|---|---|---|---|---|---|---|---|
| AAVBba.45 | 265-269 | 325-330 | 381-386 | 452-462 | 468-478 | 490-512 | 534-544 | 550-564 |
| AAVBba.46 | 265-269 | 325-330 | 381-386 | 452-462 | 468-478 | 490-512 | 534-544 | 550-564 |
| AAVBba.47 | 265-269 | 325-330 | 381-386 | 452-462 | 468-478 | 490-512 | 534-544 | 550-564 |
| AAVBba.48 | 265-269 | 325-330 | 381-386 | 452-462 | 468-478 | 490-512 | 534-544 | 550-564 |
| AAVBba.49 | 265-269 | 325-330 | 381-386 | 452-462 | 468-478 | 490-512 | 534-544 | 550-564 |
| AAVBba.50 | 265-269 | 325-330 | 381-386 | 452-462 | 468-478 | 490-512 | 534-544 | 550-564 |
| AAVBba.51 | 265-269 | 325-330 | 381-386 | 452-462 | 468-478 | 490-512 | 534-544 | 550-564 |

Transgene

The transgene is a nucleic acid sequence, heterologous to the vector sequences flanking the transgene, which encodes a polypeptide, protein, or other product, of interest. The nucleic acid coding sequence is operatively linked to regulatory components in a manner which permits transgene transcription, translation, and/or expression in a host cell.

The composition of the transgene sequence will depend upon the use to which the resulting vector will be put. For example, one type of transgene sequence includes a reporter sequence, which upon expression produces a detectable signal. Such reporter sequences include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc.

These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for beta-galactosidase activity. Where the transgene is green fluorescent protein or luciferase, the vector carrying the signal may be measured visually by color or light production in a luminometer.

However, desirably, the transgene is a non-marker sequence encoding a product which is useful in biology and medicine, such as proteins, peptides, RNA, enzymes, dominant negative mutants, or catalytic RNAs. Desirable RNA molecules include tRNA, dsRNA, ribosomal RNA, catalytic RNAs, siRNA, small hairpin RNA, trans-splicing RNA, and antisense RNAs. One example of a useful RNA sequence is a sequence which inhibits or extinguishes expression of a targeted nucleic acid sequence in the treated animal. Typically, suitable target sequences include oncologic targets and viral diseases. See, for examples of such targets the oncologic targets and viruses identified below in the section relating to immunogens.

The transgene may be used to correct or ameliorate gene deficiencies, which may include deficiencies in which normal genes are expressed at less than normal levels or deficiencies in which the functional gene product is not expressed. A preferred type of transgene sequence encodes a therapeutic protein or polypeptide which is expressed in a host cell. The invention further includes using multiple transgenes, e.g., to correct or ameliorate a gene defect caused by a multi-subunit protein. In certain situations, a different transgene may be used to encode each subunit of a protein, or to encode different peptides or proteins. This is desirable when the size of the DNA encoding the protein subunit is large, e.g., for an immunoglobulin, the platelet-derived growth factor, or a dystrophin protein. In order for the cell to produce the multi-subunit protein, a cell is infected with the recombinant virus containing each of the different subunits. Alternatively, different subunits of a protein may be encoded by the same transgene. In this case, a single transgene includes the DNA encoding each of the subunits, with the DNA for each subunit separated by an internal ribozyme entry site (IRES). This is desirable when the size of the DNA encoding each of the subunits is small, e.g., the total size of the DNA encoding the subunits and the IRES is less than five kilobases. As an alternative to an IRES, the DNA may be separated by sequences encoding a 2A peptide, which self-cleaves in a post-translational event. See, e.g., Donnelly et al, *J. Gen. Virol.*, 78(Pt 1):13-21 (January 1997); Furler, et al, *Gene Ther.*, 8(11):864-873 (June 2001); Klump et al., *Gene Ther* 8(10):811-817 (May 2001). This 2A peptide is significantly smaller than an IRES, making it well suited for use when space is a limiting factor. More often, when the transgene is large, consists of multi-subunits, or two transgenes are co-delivered, rAAV carrying the desired transgene(s) or subunits are co-administered to allow them to concatamerize in vivo to form a single vector genome. In such an embodiment, a first AAV may carry an expression cassette which expresses a single transgene and a second AAV may carry an expression cassette which expresses a different transgene for co-expression in the host cell. However, the selected transgene may encode any biologically active product or other product, e.g., a product desirable for study.

Suitable transgenes may be readily selected by one of skill in the art. The selection of the transgene is not considered to be a limitation of this invention.

In some embodiments, the transgene is a heterologous protein, and this heterologous protein is a therapeutic protein. Exemplary therapeutic proteins include, but are not limited to, blood factors, such as β-globin, hemoglobin, tissue plasminogen activator, and coagulation factors; colony stimulating factors (CSF); interleukins, such as IL-1, IL-2, IL-3, IL-4, IL-5, IL-6, IL-7, IL-8, IL-9, etc.; growth factors, such as keratinocyte growth factor (KGF), stem cell factor (SCF), fibroblast growth factor (FGF, such as basic FGF and acidic FGF), hepatocyte growth factor (HGF), insulin-like growth factors (IGFs), bone morphogenetic protein (BMP), epidermal growth factor (EGF), growth differentiation factor-9 (GDF-9), hepatoma derived growth factor (HDGF), myostatin (GDF-8), nerve growth factor (NGF), neurotrophins, platelet-derived growth factor (PDGF), thrombopoietin (TPO), transforming growth factor alpha (TGF-α.), transforming growth factor beta (TGF-β.), and the like; soluble receptors, such as soluble TNF-α. receptors, soluble VEGF receptors, soluble interleukin receptors (e.g., soluble IL-1 receptors and soluble type II IL-1 receptors), soluble.γ/δ T cell receptors, ligand-binding fragments of a soluble receptor, and the like; enzymes, such as α-glucosidase, imiglucarase, β-glucocerebrosidase, and alglucerase; enzyme activators, such as tissue plasminogen activator; chemokines, such as 1P-10, monokine induced by interferon-gamma (Mig), Groα/IL-8, RANTES, MIP-1α, MIP-1β., MCP-1, PF-4, and the like; angiogenic agents, such as vascular endothelial growth factors (VEGFs, e.g., VEGF121, VEGF165, VEGF-C, VEGF-2), glioma-derived growth factor, angiogenin, angiogenin-2; and the like; anti-angiogenic agents, such as a soluble VEGF receptor; protein vaccine; neuroactive peptides, such as nerve growth factor (NGF), bradykinin, cholecystokinin, gastin, secretin, oxytocin, gonadotropin-releasing hormone, beta-endorphin, enkephalin, substance P, somatostatin, prolactin, galanin, growth hormone-releasing hormone, bombesin, dynorphin, warfarin, neurotensin, motilin, thyrotropin, neuropeptide Y, luteinizing hormone, calcitonin, insulin, glucagons, vasopressin, angiotensin II, thyrotropin-releasing hormone, vasoactive intestinal peptide, a sleep peptide, and the like; thrombolytic agents; atrial natriuretic peptide; relaxin; glial fibrillary acidic protein; follicle stimulating hormone (FSH); human alpha-1 antitrypsin; leukemia inhibitory factor (LIF); tissue factors, luteinizing hormone; macrophage activating factors; tumor necrosis factor (TNF); neutrophil chemotactic factor (NCF); tissue inhibitors of metalloproteinases; vasoactive intestinal peptide; angiogenin; angiotropin; fibrin; hirudin; IL-1 receptor antagonists; and the like. Some other non-limiting examples of protein of interest include ciliary neurotrophic factor (CNTF); brain-derived neurotrophic factor (BDNF); neurotrophins 3 and 4/5 (NT-3 and 4/5); glial cell derived neurotrophic factor (GDNF); aromatic amino acid decarboxylase (AADC); hemophilia related clotting proteins, such as Factor VIII, Factor IX, Factor X; dystrophin, mini-dystrophin, or microdystrophin; lysosomal acid lipase; phenylalanine hydroxylase (PAH); glycogen storage disease-related enzymes, such as glucose-6-phosphatase, acid maltase, glycogen debranching enzyme, muscle glycogen phosphorylase, liver glycogen phosphorylase, muscle phosphofructokinase, phosphorylase kinase (e.g., PHKA2), glucose transporter (e.g., GLUT2), aldolase A, β-enolase, and glycogen synthase; lysosomal enzymes (e.g., beta-N-acetylhexosaminidase A); and any variants thereof.

Regulatory Control Elements

The AAV vector also includes conventional control elements or sequences which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) (see, e.g., Boshart et al, *Cell,* 41:521-530 (1985)), the SV40 promoter, the dihydrofolate reductase promoter, the β-actin promoter, the phosphoglycerol kinase (PGK) promoter, and the EF1 promoter [Invitrogen]. Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied compounds, include, the zinc-inducible sheep metallothionine (MT) promoter, the dexamethasone (Dex)-inducible mouse mammary tumor virus (MMTV) promoter, the T7 polymerase promoter system [WO 98/10088]; the ecdysone insect promoter [No et al, *Proc. Natl. Acad. Sci. USA,* 93:3346-3351 (1996)], the tetracycline-repressible system [Gossen et al, *Proc. Natl. Acad. Sci. USA,* 89:5547-5551 (1992)], the tetracycline-inducible system [Gossen et al, *Science,* 268:1766-1769 (1995), see also Harvey et al, *Curr. Opin. Chem. Biol.,* 2:512-518 (1998)], the RU486-inducible system [Wang et al, *Nat. Biotech.,* 15:239-243 (1997) and Wang et al, *Gene Ther.,* 4:432-441 (1997)] and the rapamycin-inducible system [Magari et al, *J. Clin. Invest.,* 100:2865-2872 (1997)]. Other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the transgene includes a gene operably linked to a tissue-specific promoter. For instance, if expression in skeletal muscle is desired, a promoter active in muscle should be used. These include the promoters from genes encoding skeletal β-actin, myosin light chain 2A, dystrophin, muscle creatine kinase, as well as synthetic muscle promoters with activities higher than naturally-occurring promoters (see Li et al., *Nat. Biotech.*, 17:241-245 (1999)). Examples of promoters that are tissue-specific are known for liver (albumin, Miyatake et al., *J. Virol.*, 71:5124-32 (1997); hepatitis B virus core promoter, Sandig et al., *Gene Ther.*, 3:1002-9 (1996); alpha-fetoprotein (AFP), Arbuthnot et al., *Hum. Gene Ther.*, 7:1503-14 (1996)), bone osteocalcin (Stein et al., *Mol. Biol. Rep.*, 24:185-96 (1997)); bone sialoprotein (Chen et al., *J. Bone Miner. Res.*, 11:654-64 (1996)), lymphocytes (CD2, Hansal et al., *J. Immunol.*, 161:1063-8 (1998); immunoglobulin heavy chain; T cell receptor chain), neuronal such as neuron-specific enolase (NSE) promoter (Andersen et al., *Cell. Mol. Neurobiol.*, 13:503-15 (1993)), neurofilament light-chain gene (Piccioli et al., *Proc. Natl. Acad. Sci. USA,* 88:5611-5 (1991)), and the neuron-specific vgf gene (Piccioli et al., *Neuron,* 15:373-84 (1995)), among others.

Optionally, plasmids carrying therapeutically useful transgenes may also include selectable markers or reporter genes may include sequences encoding geneticin, hygromicin or purimycin resistance, among others. Such selectable reporters or marker genes (preferably located outside the viral genome to be rescued by the method of the invention) can be used to signal the presence of the plasmids in bacterial cells, such as ampicillin resistance. Other components of the plasmid may include an origin of replication. Selection of these and other promoters and vector elements are conventional and many such sequences are available [see, e.g., Sambrook et al, and references cited therein].

Methods for Producing Recombinant AAVs

The present disclosure provides materials and methods for producing recombinant AAVs in insect or mammalian cells. In some embodiments, the viral construct further comprises a promoter and a restriction site downstream of the promoter to allow insertion of a polynucleotide encoding one or more proteins of interest, wherein the promoter and the restriction site are located downstream of the 5' AAV ITR and upstream of the 3' AAV ITR. In some embodiments, the viral construct further comprises a posttranscriptional regulatory element downstream of the restriction site and upstream of the 3' AAV ITR. In some embodiments, the viral construct further comprises a polynucleotide inserted at the restriction site and operably linked with the promoter, where the polynucleotide comprises the coding region of a protein of interest. As a skilled artisan will appreciate, any one of the AAV vector disclosed in the present application can be used in the method as the viral construct to produce the recombinant AAV.

In some embodiments, the helper functions are provided by one or more helper plasmids or helper viruses comprising adenoviral or baculoviral helper genes. Non-limiting examples of the adenoviral or baculoviral helper genes include, but are not limited to, E1A, E1B, E2A, E4 and VA, which can provide helper functions to AAV packaging.

Helper viruses of AAV are known in the art and include, for example, viruses from the family Adenoviridae and the family Herpesviridae. Examples of helper viruses of AAV include, but are not limited to, SAdV-13 helper virus and SAdV-13-like helper virus described in US Publication No. 20110201088 (the disclosure of which is incorporated herein by reference), helper vectors pHELP (Applied Viromics). A skilled artisan will appreciate that any helper virus or helper plasmid of AAV that can provide adequate helper function to AAV can be used herein.

In some embodiments, the AAV cap genes are present in a plasmid. The plasmid can further comprise an AAV rep gene. The cap genes and/or rep gene from any AAV serotype (including, but not limited to, AAV1, AAV2, AAV4, AAV5, AAV6, AAV7, AAV8, AAV9, AAV10, AAV11, AAV12, AAV13 and any variants thereof) can be used herein to produce the recombinant AAV. In some embodiments, the AAV cap genes encode a capsid from serotype 1, serotype 2, serotype 4, serotype 5, serotype 6, serotype 7, serotype 8, serotype 9, serotype 10, serotype 11, serotype 12, serotype 13 or a variant thereof.

In some embodiments, the insect or mammalian cell can be transfected with the helper plasmid or helper virus, the viral construct and the plasmid encoding the AAV cap genes; and the recombinant AAV virus can be collected at various time points after co-transfection. For example, the recombinant AAV virus can be collected at about 12 hours, about 24 hours, about 36 hours, about 48 hours, about 72 hours, about 96 hours, about 120 hours, or a time between any of these two time points after the co-transfection.

Recombinant AAV can also be produced using any conventional methods known in the art suitable for producing infectious recombinant AAV. In some instances, a recombinant AAV can be produced by using an insect or mammalian cell that stably expresses some of the necessary components for AAV particle production. For example, a plasmid (or multiple plasmids) comprising AAV rep and cap genes, and a selectable marker, such as a neomycin resistance gene, can be integrated into the genome of the cell. The insect or mammalian cell can then be co-infected with a helper virus (e.g., adenovirus or baculovirus providing the helper functions) and the viral vector comprising the 5' and 3' AAV ITR (and the nucleotide sequence encoding the heterologous protein, if desired). The advantages of this method are that the cells are selectable and are suitable for large-scale production of the recombinant AAV. As another non-limiting example, adenovirus or baculovirus rather than plasmids can be used to introduce rep and cap genes into packaging cells. As yet another non-limiting example, both the viral vector containing the 5' and 3' AAV LTRs and the rep-cap genes can be stably integrated into the DNA of producer cells, and the helper functions can be provided by a wild-type adenovirus to produce the recombinant AAV.

Cell Types Used in AAV Production

The viral particles comprising the AAV vectors of the invention may be produced using any invertebrate cell type which allows for production of AAV or biologic products and which can be maintained in culture. For example, the insect cell line used can be from *Spodoptera frugiperda*, such as Sf9, SF21, SF900+, drosophila cell lines, mosquito cell lines, e.g., *Aedes albopictus* derived cell lines, domestic silkworm cell lines, e.g. Bombyxmori cell lines, *Trichoplusia ni* cell lines such as High Five cells or Lepidoptera cell lines such as *Ascalapha odorata* cell lines. Preferred insect cells are cells from the insect species which are susceptible to baculovirus infection, including High Five, Sf9, Se301, SeIZD2109, SeUCR1, SP900+, Sf21, BTI-TN-5B1-4, MG-1, Tn368, HzAm1, BM-N, Ha2302, Hz2E5 and Ao38.

Baculoviruses are enveloped DNA viruses of arthropods, two members of which are well known expression vectors for producing recombinant proteins in cell cultures. Baculoviruses have circular double-stranded genomes (80-200 kbp) which can be engineered to allow the delivery of large genomic content to specific cells. The viruses used as a vector are generally *Autographa californica* multicapsid nucleopolyhedrovirus (AcMNPV) or *Bombyx mori* (Bm-NPV) (Kato et al., 2010).

Baculoviruses are commonly used for the infection of insect cells for the expression of recombinant proteins. In particular, expression of heterologous genes in insects can be accomplished as described in for instance U.S. Pat. No. 4,745,051; Friesen et al (1986); EP 127,839; EP 155,476; Vlak et al. (1988); Miller et al. (1988); Carbonell et al. (1988); Maeda et al. (1985); Lebacq-Verheyden et al. (1988); Smith et al. (1985); Miyajima et al. (1987); and Martin et al. (1988). Numerous baculovirus strains and variants and corresponding permissive insect host cells that can be used for protein production are described in Luckow et al (1988), Miller et al. (1986); Maeda et al. (1985) and McKenna (1989).

In another aspect of the invention, the methods of the invention are also carried out with any mammalian cell type which allows for replication of AAV or production of biologic products, and which can be maintained in culture. Preferred mammalian cells used can be HEK293, HeLa, CHO, NS0, SP2/0, PER.C6, Vero, RD, BHK, HT 1080, A549, Cos-7, ARPE-19 and MRC-5 cells.

Production of Heterologous Proteins In Vitro

As a non-limiting example, the recombinant AAV disclosed herein can be used to produce a protein of interest in vitro, for example, in a cell culture. As one non-limiting example, in some embodiments, a method for producing a protein of interest in vitro, where the method includes providing a recombinant AAV comprising a nucleotide sequence encoding the heterologous protein; and contacting the recombinant AAV with a cell in a cell culture, whereby the recombinant AAV expresses the protein of interest in the cell. The size of the nucleotide sequence encoding the protein of interest can vary. For example, the nucleotide sequence can be at least about 1.4 kb, at least about 1.5 kb, at least about 1.6 kb, at least about 1.7 kb, at least about 1.8 kb, at least about 2.0 kb, at least about 2.2 kb, at least about 2.4 kb, at least about 2.6 kb, at least about 2.8 kb, at least about 3.0 kb, at least about 3.2 kb, at least about 3.4 kb, at least about 3.5 kb in length, at least about 4.0 kb in length, at least about 5.0 kb in length, at least about 6.0 kb in length, at least about 7.0 kb in length, at least about 8.0 kb in length, at least about 9.0 kb in length, or at least about 10.0 kb in length. In some embodiments, the nucleotide is at least about 1.4 kb in length.

Production of Heterologous Proteins In Vivo

The recombinant AAV disclosed herein can be used to produce a protein of interest in vivo, for example in an animal such as a mammal. Some embodiments provide a method for producing a protein of interest in vivo, where the method includes providing a recombinant AAV comprising a nucleotide sequence encoding the protein of interest; and administering the recombinant AAV to the subject, whereby the recombinant AAV expresses the protein of interest in the subject. The subject can be, in some embodiments, a non-human mammal, for example, a monkey, a dog, a cat, a mouse, or a cow. The size of the nucleotide sequence encoding the protein of interest can vary. For example, the nucleotide sequence can be at least about 1.4 kb, at least about 1.5 kb, at least about 1.6 kb, at least about 1.7 kb, at least about 1.8 kb, at least about 2.0 kb, at least about 2.2 kb, at least about 2.4 kb, at least about 2.6 kb, at least about 2.8 kb, at least about 3.0 kb, at least about 3.2 kb, at least about 3.4 kb, at least about 3.5 kb in length, at least about 4.0 kb in length, at least about 5.0 kb in length, at least about 6.0 kb in length, at least about 7.0 kb in length, at least about 8.0 kb in length, at least about 9.0 kb in length, or at least about 10.0 kb in length. In some embodiments, the nucleotide is at least about 1.4 kb in length.

Therapeutic Uses

The recombinant AAV produced by the methods described can be used to express one or more therapeutic proteins to treat various diseases or disorders. Non-limiting examples of the diseases include cancer such as carcinoma, sarcoma, leukemia, lymphoma; and autoimmune diseases such as multiple sclerosis. Non-limiting examples of carcinomas include esophageal carcinoma; hepatocellular carcinoma; basal cell carcinoma, squamous cell carcinoma (various tissues); bladder carcinoma, including transitional cell carcinoma; bronchogenic carcinoma; colon carcinoma; colorectal carcinoma; gastric carcinoma; lung carcinoma, including small cell carcinoma and non-small cell carcinoma of the lung; adrenocortical carcinoma; thyroid carcinoma; pancreatic carcinoma; breast carcinoma; ovarian carcinoma; prostate carcinoma; adenocarcinoma; sweat gland carcinoma; sebaceous gland carcinoma; papillary carcinoma; papillary adenocarcinoma; cystadenocarcinoma; medullary carcinoma; renal cell carcinoma; ductal carcinoma in situ or bile duct carcinoma; choriocarcinoma; seminoma; embryonal carcinoma; Wilm's tumor; cervical carcinoma; uterine carcinoma; testicular carcinoma; osteogenic carcinoma; epithelieal carcinoma; and nasopharyngeal carcinoma. Non-limiting examples of sarcomas include fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas. Non-limiting examples of solid tumors include glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma. Non-limiting examples of leukemias include chronic myeloproliferative syndromes; acute myelogenous leukemias; chronic lymphocytic leukemias, including B-cell CLL, T-cell CLL prolymphocytic leukemia, and hairy cell leukemia; and acute lymphoblastic leukemias. Examples of lymphomas include, but are not limited to, B-cell lymphomas, such as Burkitt's lymphoma; Hodgkin's lymphoma; and the like. Other non-liming examples of the diseases that can be treated using the AAV vectors, recombinant viruses and methods disclosed herein include genetic disorders including sickle cell anemia, cystic fibrosis, lysosomal acid lipase (LAL) deficiency 1, Tay-Sachs disease, Phenylketonuria, Mucopolysaccharidoses, Glycogen storage diseases (GSD, e.g., GSD types I, II, III, IV, V, VI, VII, VIII, IX, X, XI, XII, XIII, and XIV), Galactosemia, muscular dystrophy (e.g., Duchenne muscular dystrophy), and hemophilia such as hemophilia A (classic hemophilia) and hemophilia B (Christmas Disease), Wilson's disease, Fabry Disease, Gaucher Disease hereditary angioedema (HAE), and alpha 1 antitrypsin deficiency. In addition, the AAV vectors, recombinant viruses and methods disclosed herein can be used to other disorders that can be treated by local expression of a transgene in the liver or by expression of a secreted protein from the liver or a hepatocyte.

The amount of the heterologous protein expressed in the subject (e.g., the serum of the subject) can vary. For example, in some embodiments the protein can be expressed in the serum of the subject in the amount of at least about 9 µg/ml, at least about 10 µg/ml, at least about 50 µg/ml, at least about 100 µg/ml, at least about 200 µg/ml, at least about 300 µg/ml, at least about 400 µg/ml, at least about 500 µg/ml, at least about 600 µg/ml, at least about 700 µg/ml, at least about 800 µg/ml, at least about 900 µg/ml, or at least about 1000 µg/ml. In some embodiments, the protein of interest is expressed in the serum of the subject in the amount of about 9 µg/ml, about 10 µg/ml, about 50 µg/ml, about 100 µg/ml, about 200 µg/ml, about 300 µg/ml, about 400 µg/ml, about 500 µg/ml, about 600 µg/ml, about 700 µg/ml, about 800 µg/ml, about 900 µg/ml, about 1000 µg/ml, about 1500 µg/ml, about 2000 µg/ml, about 2500 µg/ml, or a range between any two of these values. A skilled artisan will understand that the expression level in which a protein of interest is needed for the method to be effective can vary depending on non-limiting factors such as the particular protein of interest and the subject receiving the treatment, and an effective amount of the protein can be readily determined by a skilled artisan using conventional methods known in the art without undue experimentation.

EXAMPLES

Example 1

Isolation of Novel Naturally-Occurring Capsid Proteins

Novel naturally-occurring capsid proteins were isolated from baboon liver. Frozen liver tissue was obtained from Texas Biomedical or the New England Primate Research Center. Genomic DNA was prepared from liver tissue using the DNeasy Blood & Tissue kit (Qiagen catalog #69504).

Polymerase chain reaction (PCR) was carried out on the genomic DNA using the following primers: primer rep-1397-F (5'-GTGCCCTTTTACGGCTGCGT-GAACTGGACCAATGAAAACTTTCC-3' SEQ ID NO:21) and primer cap-2872-R (5'-CCGACG-GAGTGGGCAATGCCTCAGGAAATTGGCATTG CGATTCC-3' SEQ ID NO:22) under the following conditions: initial incubation: 97° C., 120 sec, denaturation step: 97° C., 15 sec, annealing step: 58° C., 60° C., or 62° C., 15 sec, extension step: 72° C., 240 sec. The denaturation, annealing, and extension steps were performed for 35 cycles. Then the reaction was incubated at 72° C., 7 min and stored at 4° C. until analyzed. The PCR products were separated by electrophoresis on 1% agarose gels, isolated using the Gel Extraction Kit (Qiagen catalog #28704), and cloned into pCR4-TOPO-TA (Invitrogen catalog #450030) according to the manufacturer's instructions. After transformation of E. coli, NEB5α cells, DNA was prepared from ampicillin resistant colonies and sequenced from both ends to determine if the insert encoded an AAV-related sequence.

If the inserts in pCR4-TOPO TA were related to AAV sequences, sequence-specific primers were designed to the rep portion of the sequence to perform "around the episome PCR" (hereinafter "ATE PCR") to obtain a complete capsid gene. ATE PCR is based on the notion that persistent AAV genomes forms circular episomes in animal tissues. Accordingly, one can use a "divergent" set of primers corresponding to a sequence in the rep gene to perform polymerase chain reactions to isolate most or all of any AAV sequence that may exist in that episome but in particular one could isolate a complete contiguous capsid gene. Multimers of episomes can form, for example by homologous recombination, and in that case it is possible to isolate more than one capsid gene (which usually are not the same) from a single ATE PCR reaction.

An ATE PCR was carried-out in a standard polymerase chain reaction instrument using a 2-step program as follows: initial incubation: 95° C., 240 sec, denaturation step: 95° C., 30 sec annealing/extension step: 72° C., 300 sec. The denaturation and combined annealing/extension steps were performed for 40 cycles. The reaction was then incubated at 72° C., 7 min and stored at 4° C. until analyzed. The PCR products were electrophoresed on 1% agarose gels. PCR products that were the length of multimers of an AAV genome (~4.5 kilobases) were excised from the gel, purified using the QIAquick Gel Extraction Kit (Qiagen catalog #28704), and cloned into pCR4-TOPO-TA (Invitrogen catalog #450030) according to the manufacturer's instructions. After transformation of E. coli, NEB5a cells, DNA was prepared from ampicillin resistant colonies and the entire sequence of the insert was determined.

If the 2-step program described above did not produce PCR products of the correct size the following 3-step program was used: Initial incubation: 95° C., 240 sec, Denaturation step: 95° C., 30 sec Annealing step: 62° C., 64° C., 66° C., or 68° C., 30 sec, Extension step: 72° C., 300 sec. The denaturation, annealing, and extension steps were performed for 40 cycles. Then the reaction was incubated at 72° C., 7 min and stored at 4° C. until analyzed as above.

Once complete insert sequences in pCR4-TOPO TA were determined they were identified as being AAV capsid genes using the BLAST algorithm (available at the NCBI website). Their relationship to known AAVs was determined using various nucleotide or amino acid sequence alignment programs such as Clustal Omega (available at the EBI web site) or Vector NTI (Invitrogen, Inc.).

To produce AAV, the unique AAV capsid genes were subcloned into an expression plasmid (pAAV-RC; Agilent, Inc.), then transfected into 293 cells along with a vector (pAAV luciferase) and adenovirus helper plasmid (pHELPER; Agilent, Inc.). AAV production was allowed to occur for 3 days and then crude lysates were made by freeze-thawing the cells three times. Debris was pelleted and the supernatant (crude AAV) was titered by Q-PCR to determine a genomic titer (which confirms the capsid is capable of assembly and DNA packaging) and then used to assess transduction by the AAVs on various cells.

The VP1 amino acid sequences of the novel mammalian tissue-derived AAV capsid proteins identified are herein described as SEQ ID NOS:1-7. The locations of the associated VP2 and VP3 regions are also herein described. The present invention is directed to (i) isolated AAV capsid proteins having at least 95%, 96%, 97%, 98% or 99% sequence identity to any of the VP1 capsid sequences of SEQ ID NOS:1-7, or the VP2 or VP3 regions of any of the capsid sequences of SEQ ID NOS:1-7, or (ii) isolated AAV capsid proteins comprising or consisting of any of the VP1 capsid sequences of SEQ ID NOS:1-7, or the VP2 or VP3 regions of any of the capsid sequences of SEQ ID NOS:1-7. The invention is also directed to an AAV particle that comprises any of the above described AAV capsid proteins, wherein the AAV particle further comprises either (i) a nucleic acid having AAV inverted terminal repeats and a transgene comprising a heterologous gene operably linked to regulatory sequences that direct expression of the heterologous gene in a host cell, or (ii) a nucleic acid comprising a heterologous gene operably linked to regulatory sequences that control expression of the heterologous gene in a host cell.

Neutralization of the novel AAV particles of the present invention by antibodies in human serum was also investigated. HEK293T cells were seeded in density $5 \times 10^4$ cells/well and incubated overnight. Purified rAAVs were diluted to final titer of $2 \times 10^6$ vg/uL and mixed with serial dilutions (0-10 mg/mL) of IVIG for 1 hour. Recombinant AAVs were added onto HEK293T cells using MOI of 1000 and incubated in 37° C. Seventy-two hours post-infection, IVIG neutralization was analyzed based on relative luciferase unit (RLU) reading. No etoposide was used in this study. The results are provided in Table 3. As expected, AAV2 transduction (positive control) was abolished by the addition of human IVIG (not shown). In contrast, certain of the novel AAVs tested exhibited IVIG resistant properties.

animal as well as individual organs to quantify the total flux (TF) (photons/second) being released by luciferase activity. Total flux activity is a proxy for AAV infectivity of each organ system and is shown for each AAV capsid in FIG. 1. The data demonstrate that the novel capsids produce recombinant AAV that have a high degree of specificity for liver cells.

Figure 3:
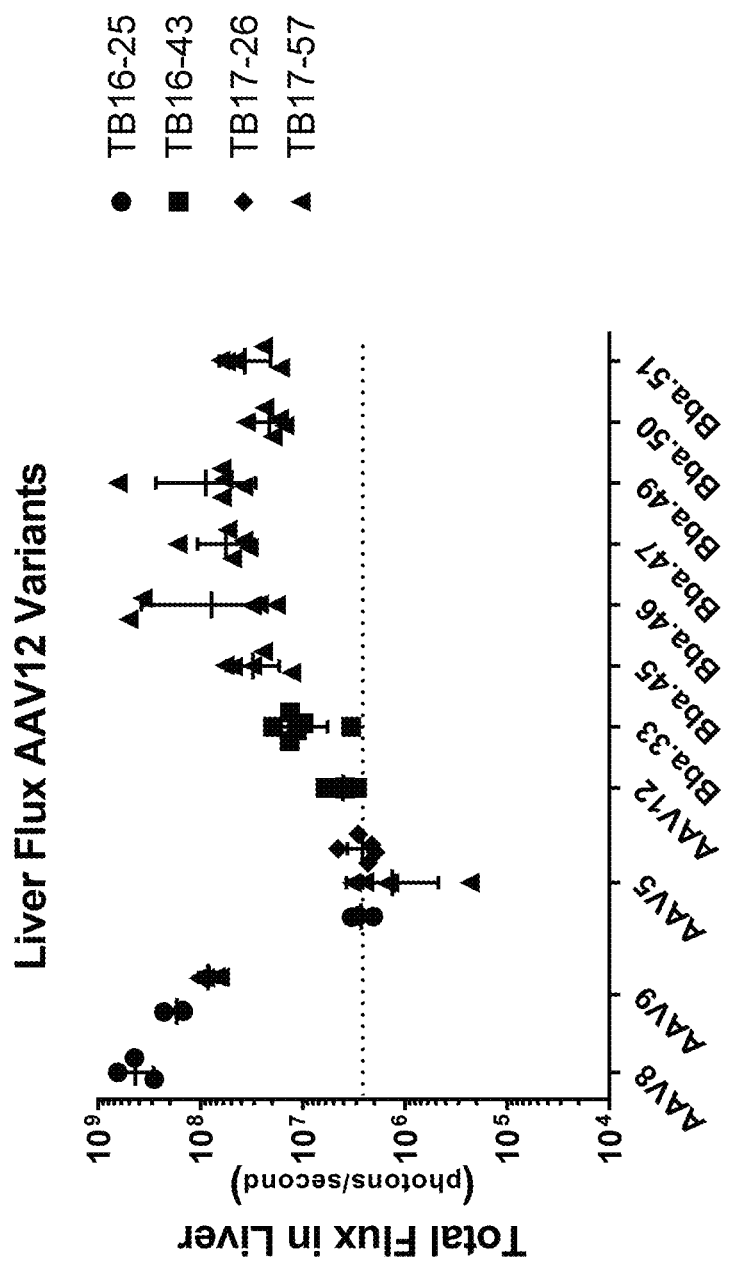
FIG. 3 provides transduction data for the novel capsids: Bba-33, Bba-45, Bba-46, Bba-47, Bba-49, Bba-50 and Bba-51 and control capsids: AAV5, AAV8 and AAV9. The data is shown as total flux activity, which is a proxy for AAV infectivity of each organ system.

Additional experiments were carried out as described above using AAV having the following capsids disclosed herein (Bba.45, Bba.46, Bba.47, Bba.49, Bba.50 and Bba.51), and the transduction was compared with that AAV having the following control capsids: AAV5, AAV8, AAV9 and AAV12. As shown in FIG. 3, the AAV having the novel capsids exhibit an increase in transduction efficiency compared to AAV having the capsids from AAV5 or AAV12. For example, the novel capsids have a 10-40 fold increase in transduction efficiency compared to AAV having the AAV5 capsid. This data was generated in multiple experiments and the multiple data points for each capsid represents different

TABLE 3

IVIG Neutralization Data:

| IVIG (mg/ml) | 10 | 5 | 2.5 | 1.25 | 0.625 | 0.312 | 0.156 | 0.0781 | 0.039 |
|---|---|---|---|---|---|---|---|---|---|
| Bba.45 | 268.0035 | 2460.32 | 25398.7 | 62037.8 | 120120.5 | 128270 | 163621.5 | 156841 | 174272 |
| Bba.46 | 143.001 | 1030.049 | 6323.76 | 36465.35 | 92936.55 | 102423.15 | 179724 | 124453 | 156407.5 |
| Bba.47 | 471.01665 | 1366.085 | 9060.61 | 42023.6 | 90104.35 | 123976.5 | 169643.5 | 152828.5 | 186058.5 |
| Bba.49 | 271.004 | 1100.063 | 15301.9 | 65175.15 | 148917 | 159579.5 | 222658.5 | 337455.5 | 309530.5 |
| Bba.50 | 188.0021 | 660.027 | 1574.105 | 6904.1 | 14449.3 | 19913.45 | 21366.1 | 26117.05 | 28455.65 |
| Bba.51 | 1223.0695 | 1508.1235 | 10817.1 | 55625 | 103595.5 | 151814 | 153542 | 178776 | 255409 |

In addition, the IVIG neutralization assay was repeated to compare neutralization of the recombinant AAV particles having the capsids listed in Table 3 (denoted as "novel capsids", with the neutralization of recombinant AAV particles having the control capsids: AAV5, AAV8 and AAV9. As shown in FIG. 2, the AAV having the capsids disclosed herein exhibited IVIG resistant properties.

In order to determine the tissue specific infectivity of the AAV capsids disclosed herein, AAV comprising each of the capsids and expressing the luciferase transgene were generated (AAV-RSV-egfp-T2A-Fluc2). Male Balb/C mice were purchased from Charles River Breeding Laboratories. A dose of $2 \times 10^{13}$ vg/kg of AAV-RSV-egfp-T2A-Fluc2 vector was injected into the tail vein of 8 week old mice. At 3 and 5 weeks post injection, in vivo bioluminescent imaging was performed using an in vivo imagining device (IVIS Lumina LT obtained from PerkinElmer Inc., Waltham, Mass.). In brief, the mice were anesthetized with 2% isofluorane and oxygen. 150 µl of 30 mg/ml of RediJect D-Luciferin Bioluminescent Substrate was injected intraperitoneally. Ten minutes after substrate injection, the animals were imaged with the in vivo imaging device using its cooled charge-coupled device (CCD) camera. Images were takes in the dorsal positions of the animals. Anesthesia was maintained throughout the entire imaging session by isofluorane-oxygen delivery in the light-tight imaging chamber.

Figure 4:
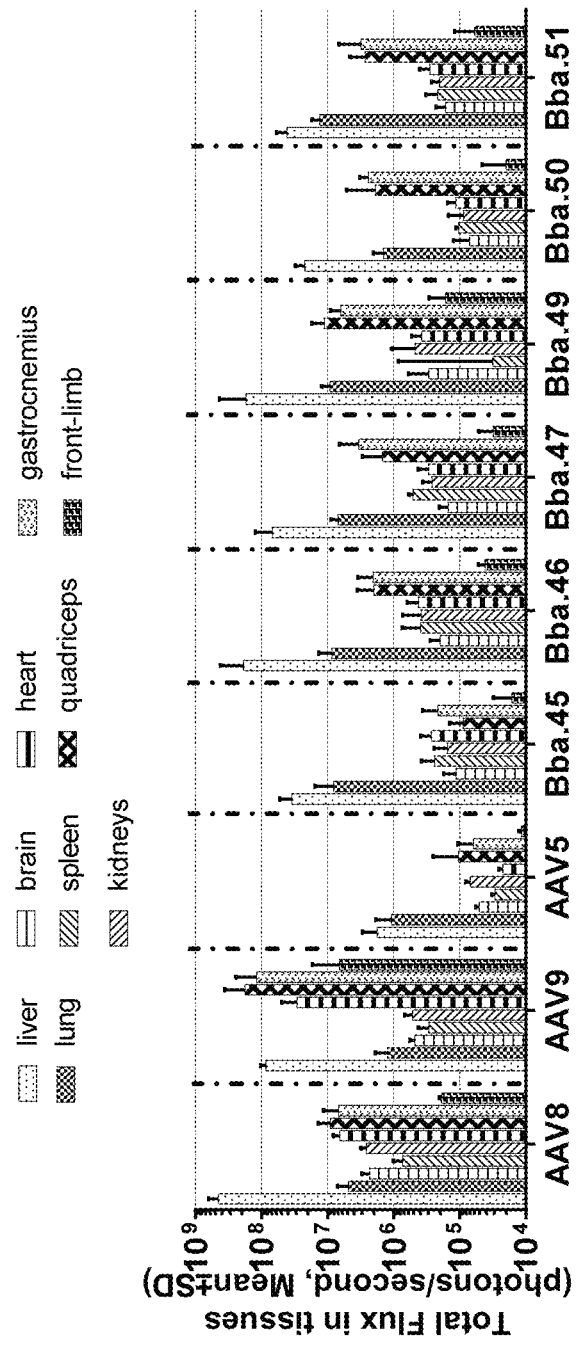
FIG. 4 provides transduction data in multiple tissues for the novel capsids: Bba-45, Bba-46, Bba-47, Bba-49, Bba-50 and Bba-51 and control capsids: AAV5, AAV8 and AAV9. This data demonstrates that the AAV having the novel capsids have a high degree of specificity for liver cells.

The mice were sacrificed after the imaging sessions at 5 weeks post AAV injection. Various organs were harvested and imaged using the imaging device. The measurement conditions were the same as those used for in vivo imaging. For imaging, a gray-scale photograph of the animals was acquired, followed by bioluminescence image acquisition. Image data was processed and analyzed using living image software version 4.5.2 (PerkinsElmer Waltham, Mass.). Regions of interest (ROIs) were traced surrounding each experiments. Furthermore, FIG. 4 demonstrates that the AAV having the novel capsids have a significantly higher degree of specificity for liver cells compared to AAV5. In addition, the AAV having the novel capsids exhibited transduction of liver cells similar to that observed with AAV having AAV8 or AAV9 capsids.

Example 2

Evaluation of Evaluate Bio-Distribution and Activity of Novel Naturally-Occurring Capsid Proteins To evaluate bio-distribution and activity of the AAV capsids disclosed herein, AAV comprising the capsids, the choriogonadotropin subunit beta (cyno-CG-Beta) transgene under the ApoE-hAAT promoter were generated (AAV-ApoE-hAAT-Cyno-CG-Beta). Male C57BL/6J mice were purchased from Jackson Laboratories. A dose of $2 \times 10^{13}$ vg/kg of AAV-ApoE-hAAT-Cyno-CG-Beta was injected into the tail vein of 8 week old mice. This study was carried out with AAV having the following capsid proteins: Bba-45, Bba-46, Bba-47, Bba-49, Bba-50 (denoted collectively as "novel capsids") and AAV5, AAV8, AAV-Rh10 and AAV-anc80L65 (denoted collectively as "control capsids"). The vehicle control was administration without an AAV vector.

Figure 5:
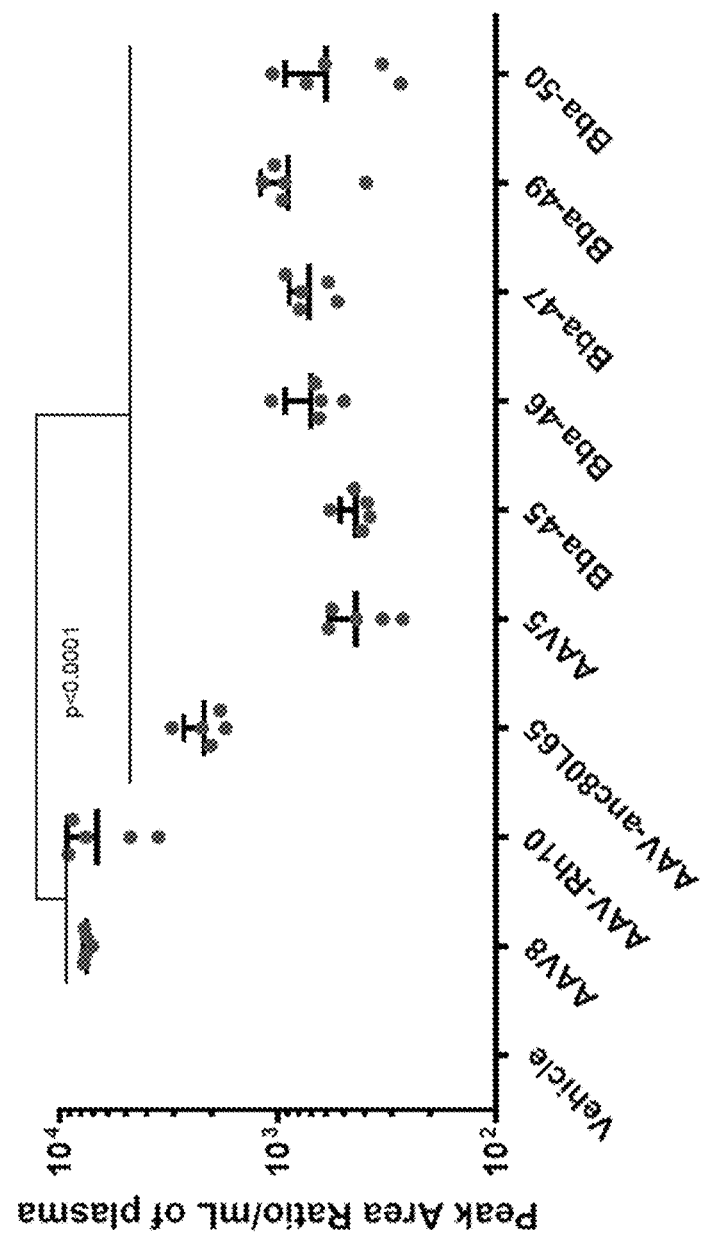
FIG. 5 provides the plasma bCG protein levels after injection of the novel capsids: Bba-45, Bba-46, Bba-47, Bba-49 and Bba-50 and control capsids: AAV8, AAV-rh10, AAV-anc80L65 and AAV5.
Figure 6:
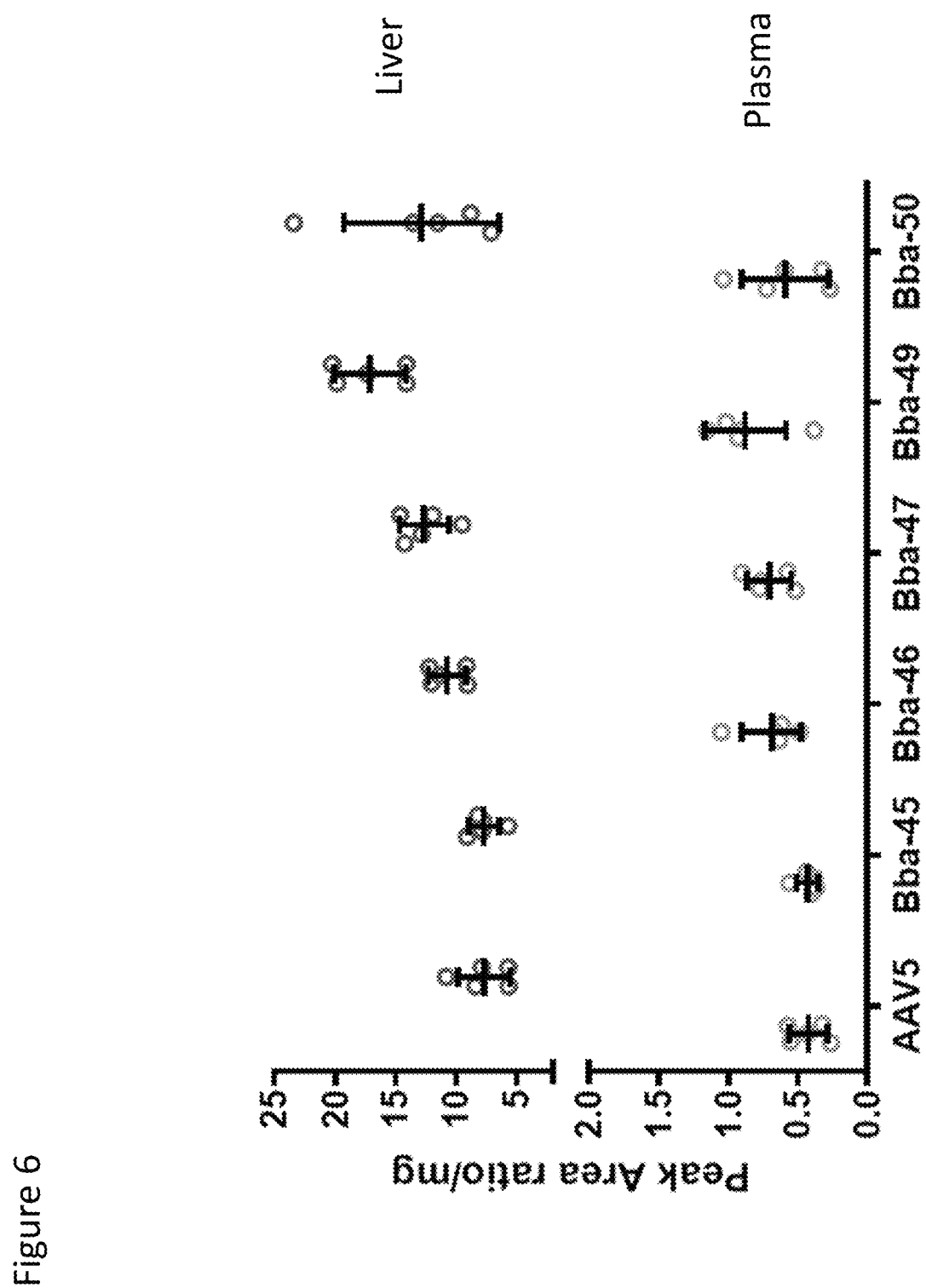
FIG. 6 provides the level of bCG protein levels in the liver (top) and plasma (bottom) after injection of the novel capsids: Bba-45, Bba-46, Bba-47, Bba-49 and Bba-50 and control capsids: AAV5.
Figure 7B:
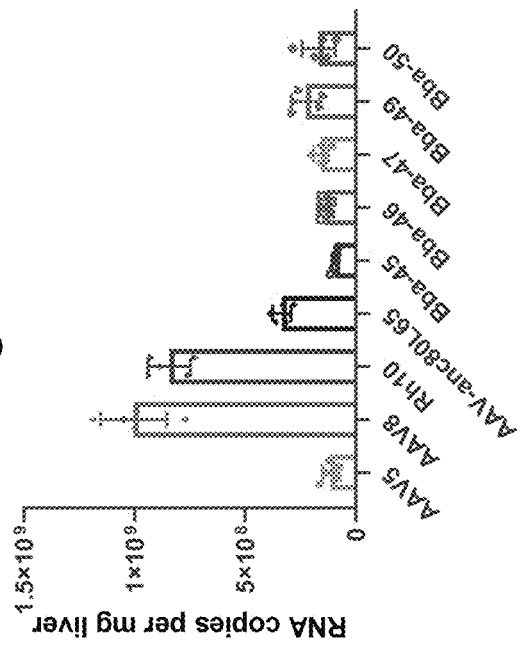
FIGS. 7A-7C provide the level of bCG DNA (Panel A), bCG RNA (Panel B) and bCG protein (Panel C) in the liver after injection of the novel capsids: Bba-45, Bba-46, Bba-47, Bba-49 and Bba-50 and control capsids: AAV8, AAV-rh10 and AAV-anc80L65.
Figure 7C:
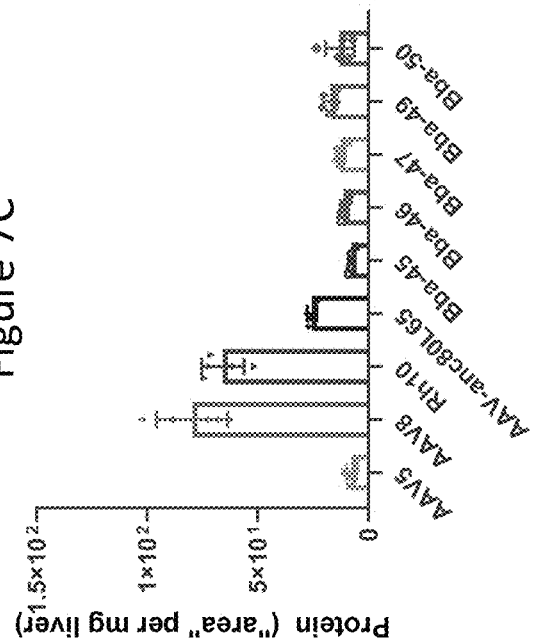
Figure 7A:
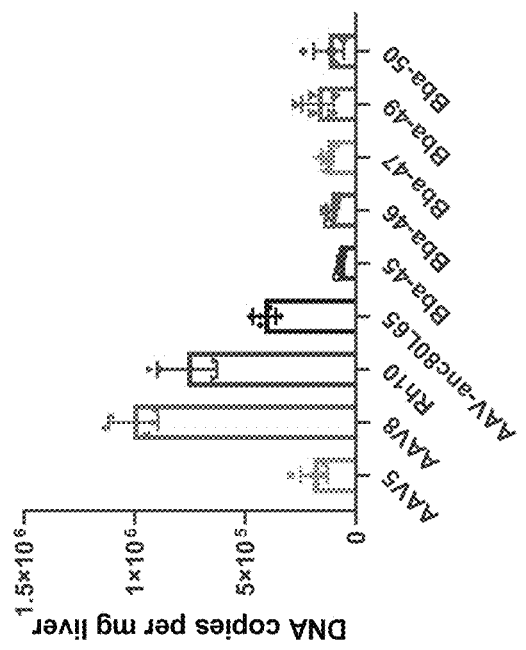
Figure 8B:
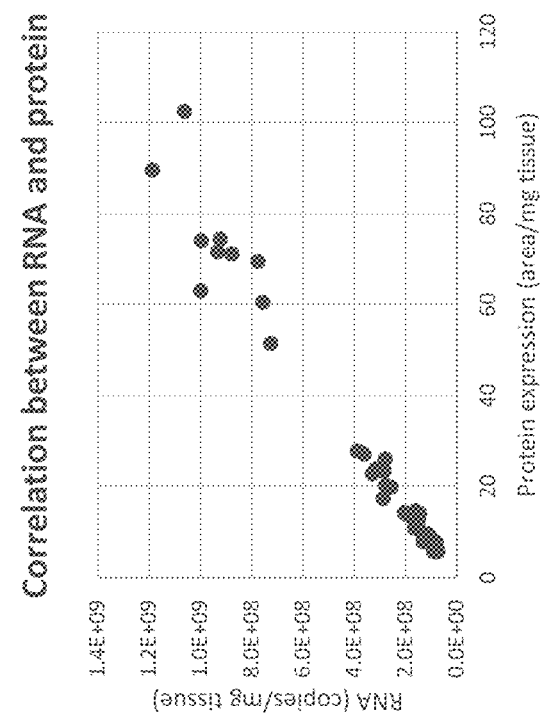
FIG. 8A-8B demonstrates a correlation between the bCG DNA and bCG RNA levels (A) and a correlation between the bCG RNA and bCG protein levels (B) in the liver after injection of the novel capsids: Bba-45, Bba-46, Bba-47, Bba-49 and Bba-50 and control capsids: AAV8, AAV-rh10 and AAV-anc80L65.
Figure 8A:
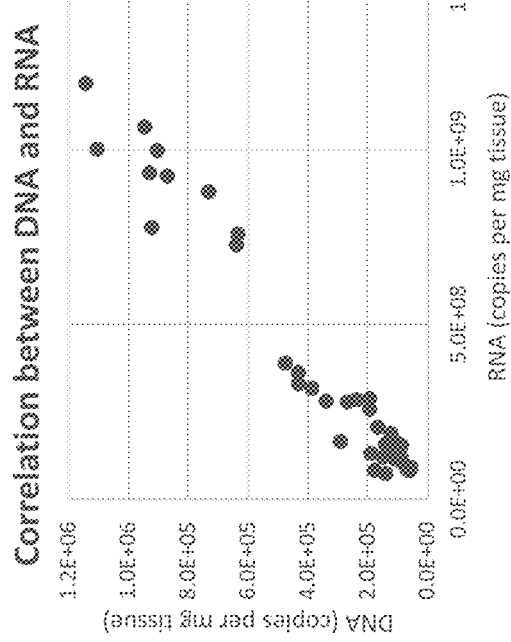

At 5 weeks post injection, expression of the cyno-CG transgene was evaluated by measuring the plasma level of the bCG protein using mass spectrometry. As shown in FIG. 5, the AAV having the novel capsids expressed the transgene at a level that is similar to the expression in AAV having the AAV5 capsid. However, the expression of bCG protein in the liver was increased in mice injected with AAV having the novel capsids compared to mice injected with AAV having the AAV5 capsid (FIG. 6). The number of DNA and RNA copies of the cyno-CG transgene in the liver of mice injected with AAV having the novel capsids were not significantly different than mice injected AAV having the AAV5 capsid (FIG. 7A-7B). The DNA and RNA data correlated well to the bCG protein data (see FIG. 8A-8B).

Novel capsids Bba-45 to Bba-50 did not lead to significantly higher transduction or transcript levels compared to the control capsids (AAV5, AAV8, AAV-Rh10 and AAV-anc80L65). However, when comparing all of the novel capsids, Bba-49 achieved the highest transcript and transduction levels. The Bba-49 capsid achieved about a 2-fold higher transcript levels (RNA) compared to the AAV5 capsid, but this difference is not significant (FIG. 7B). The ratio of Bba-49 to AAV5 are set out in Table 4:

TABLE 4

| Ratio between Bba49 and AAV5 | |
|---|---|
| Protein | 2.23 |
| RNA | 1.98 |
| DNA | 0.90 |

Figure 9:
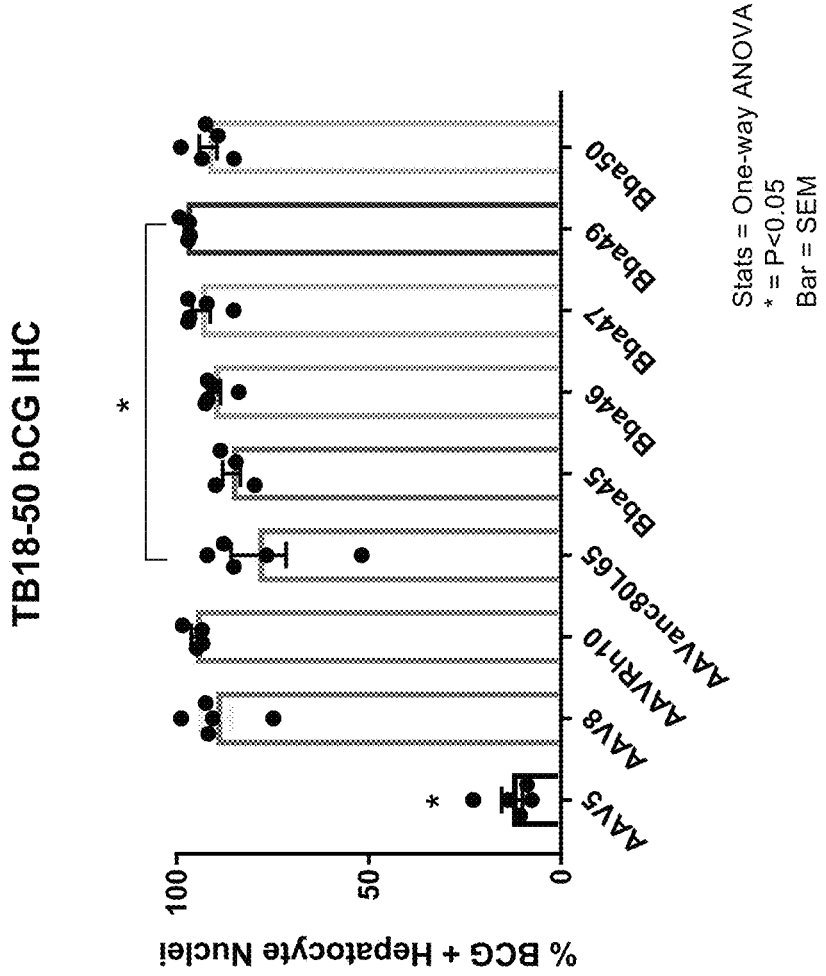
FIG. 9 provides the percentage of hepatocytes transduced by AAV after injection of the novel capsids: Bba-45, Bba-46, Bba-47, Bba-49 and Bba-50 and control capsids: AAV5, AAV8, AAV-rh10 and AAV-anc80L65 as determined by immunohistochemistry.
Figure 10:
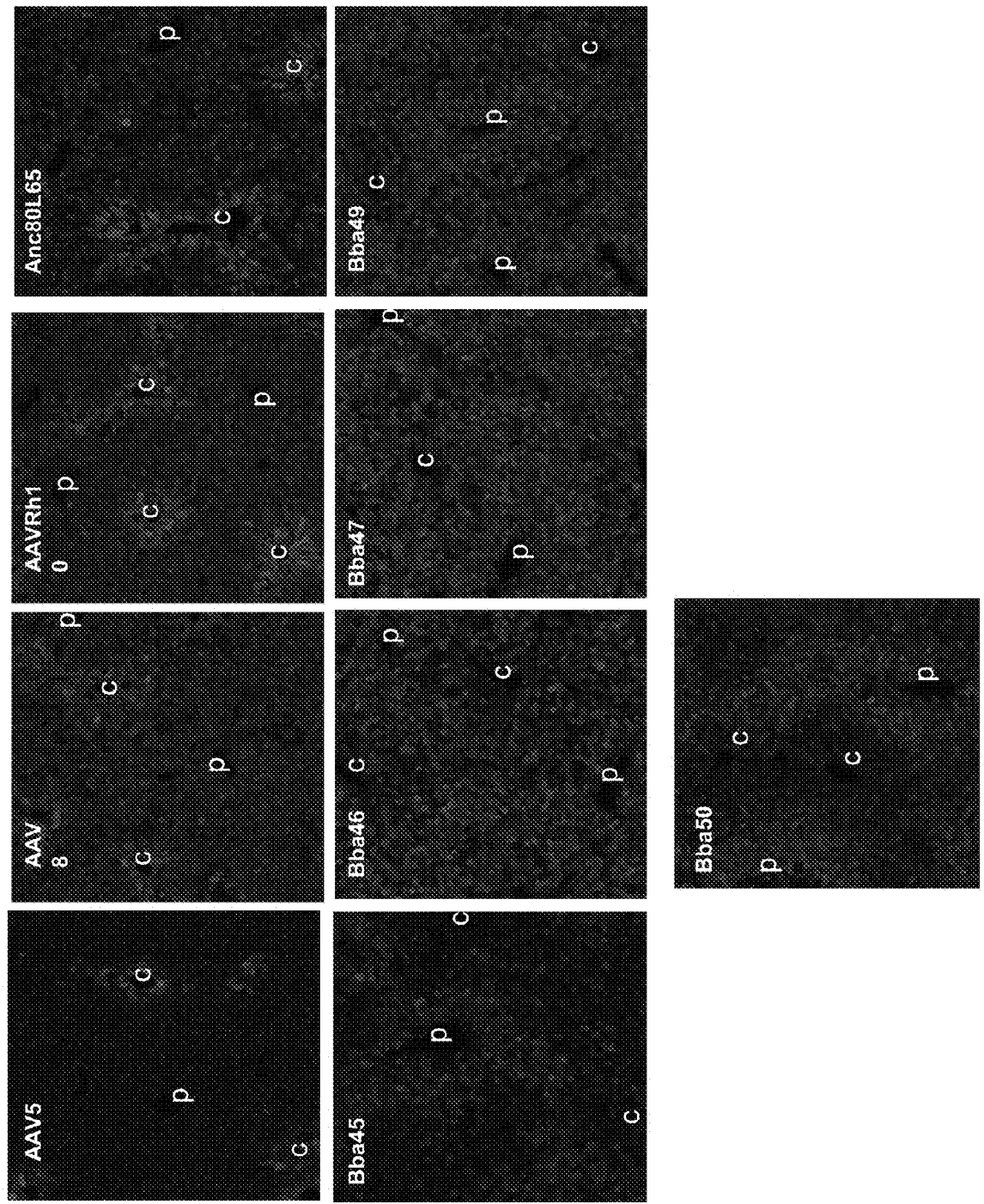
FIG. 10 provides exemplary photos showing immunohistochemistry staining of hepatocytes after injection of the novel capsids: Bba-45, Bba-46, Bba-47, Bba-49 and Bba-50 and control capsids: AAV5, AAV8, AAV-rh10 and AAV-anc80L65.

The expression of transgene bCG in hepatocytes was evaluated using immunohistochemistry. All of the novel capsids resulted in a higher percent of hepatocytes expressing bCG than AAV5 capsid. In addition, the transduction of hepatocytes by the AAV having the novel capsids were similar to the control capsids, AAV8 and AAV-Rh10. However, AAV comprising the Bba-49 capsid has a significantly greater level of transduced hepatocytes compared to AAV comprising the AAV-anc80L65 capsid (FIGS. 9 and 10).

Figure 11:
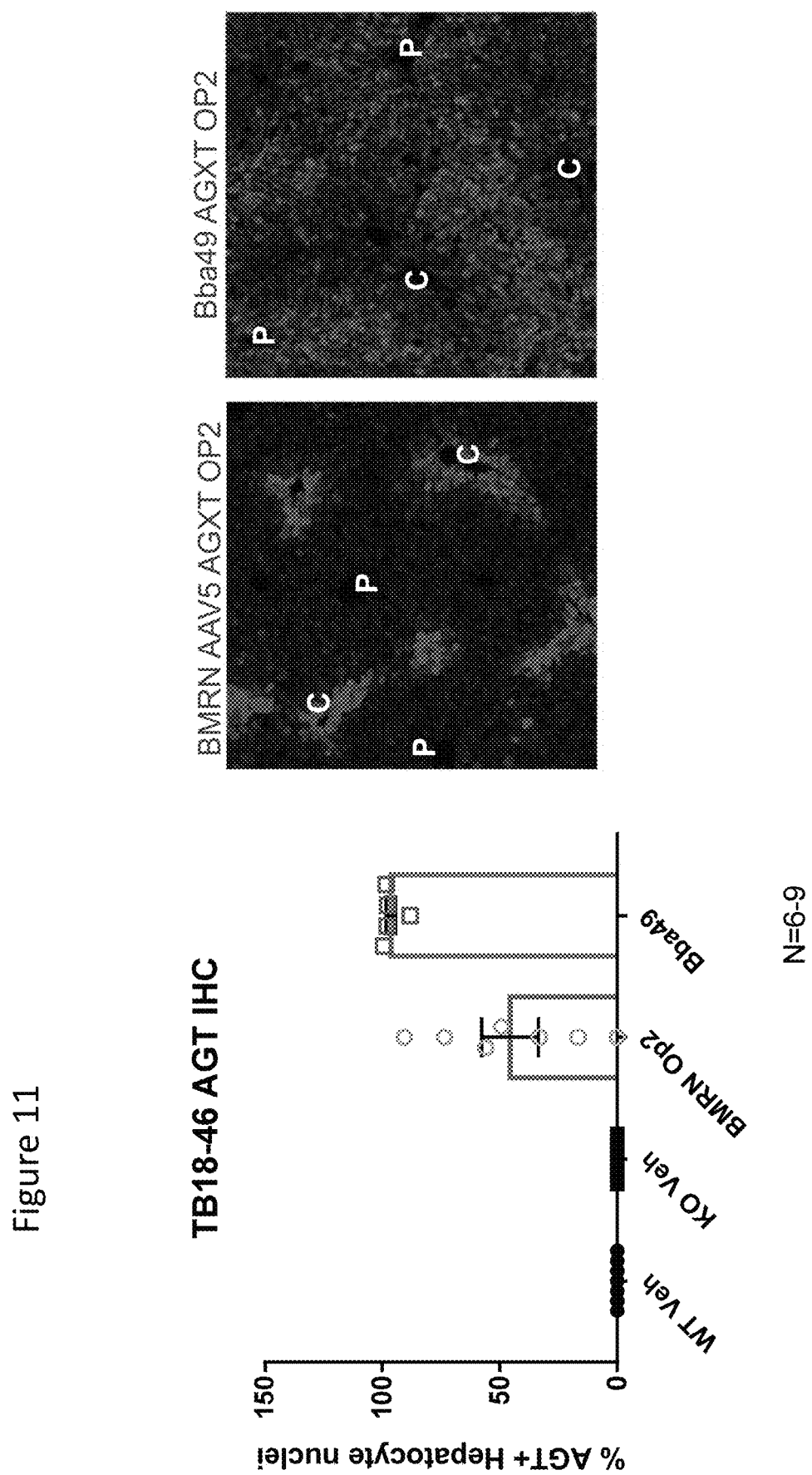
FIG. 11 provides the percentage of hepatocytes transduced by AAV having either the novel capsid Bba-49 or the AAV5 capsid carrying the—AGXT transgene. Quantitative analysis confirmed that AAV-Bba49-AGXT transduced about 96% of the hepatocytes.

AAV comprising the Bba-49 capsid, ApoE-hAAT promoter, the alanine glyoxalate amino transferase (AGXT) transgene were generated. A dose of 1E14 vg/kg of AAV-AGXT was injected into the tail vein of 3 to 4 week old ⁻AGXT/⁻/⁻C57BL/6J male mice. The transduction of the hepatocytes was compared to the same vector genome packaged into AAV particles having the AAV5 capsid. The expression of transgene AGXT in hepatocytes was evaluated using immunohistochemistry. As shown in FIG. 11, the Bba-49 capsid resulted in a higher percent of hepatocytes expressing AGXT the AAV5 capsid tested. The AAV.Bba-49. AGXT transduced about 96% of the hepatocytes.

What is claimed:

1. A recombinant adeno-associated virus (rAAV) comprising:
   (a) a capsid protein comprising an amino acid sequence that is at least 98% identical to: (i) a VP1 region of any one of SEQ ID NOS: 2 and 4-6, (ii) a VP2 region of any one of SEQ ID NOS: 2 and 4-6, or (iii) a VP3 region of any one of SEQ ID NOS: 2 and 4-6, wherein the capsid protein comprises variable regions (VRs) IV to VII of any one of SEQ ID NOS: 2 and 4-6, and constant regions in between; and
   (b) a transgene comprising a heterologous gene operably linked to a regulatory sequence that controls expression of the heterologous gene in a host cell.

2. The rAAV of claim 1, wherein the capsid protein comprises an amino acid sequence that is at least 99% identical to: (i) the VP1 region of any one of SEQ ID NOS: 2 and 4-6, (ii) the VP2 region of any one of SEQ ID NOS: 2 and 4-6, or (iii) the VP3 region of any one of SEQ ID NOS: 2 and 4-6.

3. A composition comprising the rAAV of claim 1, and a physiologically compatible carrier.

4. A method of delivering a transgene to a cell comprising contacting the cell with the rAAV of claim 1.

5. The method of claim 4, wherein the cell is a liver cell.

6. A method of treating a subject suffering from a disorder or disease associated with abnormal activity of an endogenous protein comprising administering to the subject an effective amount of the rAAV of claim 1.

7. The method of claim 6, wherein the disorder or disease is associated with abnormal activity of an endogenous gene expressed in a liver cell.

8. The method of claim 6, wherein the disorder or disease is selected from the group consisting of hemophilia A, hemophilia B, Wilson's disease, hereditary angioedema (HAE), alpha 1 antitrypsin deficiency, and galactosemia.

9. The rAAV of claim 1, wherein the capsid protein comprises an amino acid sequence that is at least 98% identical to: (i) the VP1 region of SEQ ID NO:5, (ii) the VP2 region of SEQ ID NO:5, or (iii) the VP3 region of SEQ ID NO:5.

10. The rAAV of claim 1, wherein the capsid protein comprises an amino acid sequence that is at least 99% identical to: (i) the VP1 region of SEQ ID NO:5, (ii) the VP2 region of SEQ ID NO:5, or (iii) the VP3 region of SEQ ID NO:5.

11. A recombinant adeno-associated virus (rAAV) comprising:

(a) a capsid protein comprising an amino acid sequence that is at least 98% identical to: (i) a VP1 region of any one of SEQ ID NOS: 1-7, (ii) a VP2 region of any one of SEQ ID NOS:1-7, or (iii) a VP3 region of any one of SEQ ID NOS:1-7, wherein the capsid protein comprises a GH loop that is identical to the GH loop of any one of SEQ ID NOS: 1-7, wherein the GH loop comprises variable regions (VRs) IV to VIII; and (b) a transgene comprising a heterologous gene operably linked to a regulatory sequence that controls expression of the heterologous gene in a host cell.

12. The rAAV of claim 11, wherein the capsid protein comprises an amino acid sequence that is at least 99% identical to: (i) the VP1 region of any one of SEQ ID NOS:1-7, (ii) the VP2 region of any one of SEQ ID NOS:1-7, or (iii) the VP3 region of any one of SEQ ID NOS:1-7.

13. The rAAV of claim 11, wherein the capsid protein comprises an amino acid sequence that is at least 98% identical to: (i) the VP1 region of SEQ ID NO:5, (ii) the VP2 region of SEQ ID NO:5, or (iii) the VP3 region of SEQ ID NO:5.

14. A composition comprising the rAAV of claim 11, and a physiologically compatible carrier.

15. A method of delivering a transgene to a cell comprising contacting the cell with the rAAV of claim 3.

16. The method of claim 15, wherein the cell is a liver cell.

17. A method of treating a subject suffering from a disorder or disease associated with abnormal activity of an endogenous protein comprising administering to the subject an effective amount of the rAAV of claim 11.

18. The method of claim 17, wherein the disorder or disease is associated with abnormal activity of an endogenous gene expressed in a liver cell.

19. The method of claim 17, wherein the disorder or disease is selected from the group consisting of hemophilia A, hemophilia B, Wilson's disease, hereditary angioedema (HAE), alpha 1 antitrypsin deficiency, and galactosemia.

20. A recombinant adeno-associated virus (rAAV) comprising:
(a) a capsid protein comprising the amino acid sequence of: (i) a VP1 region of any one of SEQ ID NOS: 1-7, (ii) a VP2 region of any one of SEQ ID NOS:1-7, or (iii) a VP3 region of any one of SEQ ID NOS:1-7; and
(b) a transgene comprising a heterologous gene operably linked to a regulatory sequence that controls expression of the heterologous gene in a host cell.

21. The rAAV of claim 20, wherein the capsid protein comprises an amino acid sequence encoded by a nucleotide sequence of any one of SEQ ID NOS: 8-14.

22. A vector comprising a nucleic acid sequence encoding an adeno-associated virus (AAV) capsid protein comprising an amino acid sequence that is at least 98% identical to: (i) a VP1 region of any one of SEQ ID NOS:1-7, (ii) a VP2 region of any one of SEQ ID NOS:1-7, or (iii) a VP3 region of any one of SEQ ID NOS:1-7, wherein the capsid protein comprises a GH loop that is identical to the GH loop of any one of SEQ ID NOS:1-7, wherein the GH loop comprises variable regions (VRs) IV to VIII, and wherein the nucleic acid sequence is operably linked to a heterologous regulatory element that controls expression of the capsid protein in a host cell.

23. The vector of claim 22, wherein the capsid protein comprises the amino acid sequence of: (i) the VP1 region of any one of SEQ ID NOS:1-7, (ii) the VP2 region of any one of SEQ ID NOS:1-7, or (iii) the VP3 region of any one of SEQ ID NOS:1-7.

24. An in vitro cell comprising the vector of claim 22.

25. The vector of claim 22, wherein the capsid protein comprises an amino acid sequence that is at least 99% identical to: (i) the VP1 region of any one of SEQ ID NOS:1-7, (ii) the VP2 region of any one of SEQ ID NOS:1-7, or (iii) the VP3 region of any one of SEQ ID NOS:1-7.

26. A vector comprising: a nucleic acid sequence encoding an adeno-associated virus (AAV) capsid protein comprising an amino acid sequence that is at least 98% identical to: (i) a VP1 region of any one of SEQ ID NOS: 2 and 4-6, (ii) a VP2 region of any one of SEQ ID NOS: 2 and 4-6, or (iii) a VP3 region of any one of SEQ ID NOS: 2 and 4-6, wherein the capsid protein comprises variable regions (VRs) IV to VII of any one of SEQ ID NOS:2 and 4-6, and constant regions in between, and wherein the nucleic acid sequence is operably linked to a heterologous regulatory element that controls expression of the capsid protein in a host cell.

27. An in vitro cell comprising the vector of claim 26.

28. The vector of claim 26, wherein the capsid protein comprises an amino acid sequence that is at least 99% identical to (i) the VP1 region of any one of SEQ ID NOS: 2 and 4-6, (ii) the VP2 region of any one of SEQ ID NOS: 2 and 4-6, or (iii) the VP3 region of any one of SEQ ID NOS: 2 and 4-6.

29. The vector of claim 26, wherein the capsid protein comprises an amino acid sequence that is identical to (i) the VP1 region of any one of SEQ ID NOS: 2 and 4-6, (ii) the VP2 region of any one of SEQ ID NOS: 2 and 4-6, or (iii) the VP3 region of any one of SEQ ID NOS: 2 and 4-6.

30. A method of producing a recombinant adeno-associated virus (rAAV) comprising:
(a) culturing in a cell culture a cell comprising an AAV vector comprising one or more AAV inverted terminal repeat sequences flanking a transgene comprising a heterologous gene operably linked to a regulatory sequence that controls expression of the heterologous gene in a host cell, wherein the cell expresses AAV rep and a capsid protein, wherein the capsid protein is at least 98% identical to: (i) a VP1 region of any one of SEQ ID NOS:1-7, (ii) a VP2 region of any one of SEQ ID NOS:1-7, or (iii) a VP3 region of any one of SEQ ID NOS:1-7, wherein the capsid protein comprises a GH loop that is identical to the GH loop of any one of SEQ ID NOS:1-7, and wherein the GH loop comprises variable regions (VRs) IV to VIII; and
(b) collecting the rAAV from the supernatant of the cell culture.

31. The method of claim 30, wherein the cell is a mammalian cell, invertebrate cell, or an insect cell.

32. The method of claim 31,
(a) wherein the mammalian cell is selected from the group consisting of HEK293, Hela, CHO, NS0, SP2/0, Vero, RD, BHK, HT 1080, A549, Cos-7, ARPE-19, and MRC-5 cells; or
(b) wherein the insect cell is selected from the group consisting of Sf9, Se301, SeIZD2109, SeUCR1, Sf21, BTI-TN-5B1-4, MG-1, Tn368, HzAm1, BM-N, Ha2302, Hz2E5, and Ao38 cells.

33. The method of claim 30, wherein the mammalian cell is a HEK293 cell.

34. A rAAV produced by the method of claim 30.

35. The method of claim 30, wherein the capsid protein is at least 99% identical to: (i) the VP1 region of any one of SEQ ID NOS:1-7, (ii) the VP2 region of any one of SEQ ID NOS:1-7, or (iii) the VP3 region of any one of SEQ ID NOS:1-7.

36. The method of claim 30, wherein the capsid protein is identical to: (i) the VP1 region of any one of SEQ ID NOS:1-7, (ii) the VP2 region of any one of SEQ ID NOS:1-7, or (iii) the VP3 region of any one of SEQ ID NOS:1-7.

37. A method of producing a recombinant adeno-associated virus (rAAV) comprising:
 (a) culturing in a cell culture a cell comprising an AAV vector comprising one or more AAV inverted terminal repeat sequences flanking a transgene comprising a heterologous gene operably linked to a regulatory sequence that controls expression of the heterologous gene in a host cell, wherein the cell expresses AAV rep and a capsid protein, wherein the capsid protein is at least 98% identical to: (i) a VP1 region of any one of SEQ ID NOS:2 and 4-6, (ii) a VP2 region of any one of SEQ ID NOS:2 and 4-6, or (iii) a VP3 region of any one of SEQ ID NOS:2 and 4-6, wherein the capsid protein comprises variable regions (VRs) IV to VII of any one of SEQ ID NOS: 2 and 4-6, and constant regions in between; and
 (b) collecting the rAAV from the supernatant of the cell culture.

38. The method of claim 37, wherein the capsid protein is at least 99% identical to: (i) the VP1 region of any one of SEQ ID NOS:2 and 4-6, (ii) the VP2 region of any one of SEQ ID NOS:2 and 4-6, or (iii) the VP3 region of any one of SEQ ID NOS:2 and 4-6.

39. The method of claim 37, wherein the capsid protein is identical to: (i) the VP1 region of any one of SEQ ID NOS: 2 and 4-6, (ii) the VP2 region of any one of SEQ ID NOS:2 and 4-6, or (iii) the VP3 region of any one of SEQ ID NOS:2 and 4-6.

40. A rAAV produced by the method of claim 37.

* * * * *

UNITED STATES PATENT AND TRADEMARK OFFICE
CERTIFICATE OF CORRECTION

PATENT NO. : 11,821,008 B2
APPLICATION NO. : 16/411848
DATED : November 21, 2023
INVENTOR(S) : Peter Cameron Colosi et al.

It is certified that error appears in the above-identified patent and that said Letters Patent is hereby corrected as shown below:

In the Claims

Claim 15:
Column 87, Line 26, "claim 3" should read -- claim 11 --.

Claim 33:
Column 88, Line 63, "claim 30" should read -- claim 32 --.

Signed and Sealed this
Twelfth Day of March, 2024

Katherine Kelly Vidal
*Director of the United States Patent and Trademark Office*